United States Patent
Tan et al.

(10) Patent No.: US 9,603,869 B2
(45) Date of Patent: Mar. 28, 2017

(54) LITHIUM CO-CRYSTALS AND AN ADDITIONAL NEUROPSYCHIATRIC AGENT FOR TREATMENT OF NEUROPSYCHIATRIC DISORDERS

(71) Applicants: Jun Tan, Tampa, FL (US); Adam John Smith, Tampa, FL (US); Roland Douglas Shytle, Largo, FL (US)

(72) Inventors: Jun Tan, Tampa, FL (US); Adam John Smith, Tampa, FL (US); Roland Douglas Shytle, Largo, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/161,202

(22) Filed: May 21, 2016

(65) Prior Publication Data

US 2016/0339055 A1 Nov. 24, 2016

Related U.S. Application Data

(60) Provisional application No. 62/165,238, filed on May 22, 2015.

(51) Int. Cl.
| | | |
|---|---|---|
| *A61K 38/00* | (2006.01) | |
| *A61K 33/00* | (2006.01) | |
| *A61K 47/48* | (2006.01) | |
| *A61K 45/06* | (2006.01) | |

(52) U.S. Cl.
CPC .............. *A61K 33/00* (2013.01); *A61K 38/00* (2013.01); *A61K 45/06* (2013.01); *A61K 47/48038* (2013.01); *A61K 47/48061* (2013.01)

(58) Field of Classification Search
CPC ...................................................... A61K 38/00
See application file for complete search history.

(56) References Cited

U.S. PATENT DOCUMENTS

| | | |
|---|---|---|
| 4,753,964 A | 6/1988 | Horrobin |
| 5,603,959 A | 2/1997 | Horrobin et al. |
| 6,160,018 A | 12/2000 | Wechter et al. |
| 2010/0068308 A1 | 3/2010 | Phiel et al. |
| 2012/0301551 A1 | 11/2012 | Gwag et al. |
| 2013/0156869 A1 | 6/2013 | Nunes et al. |
| 2014/0242193 A1 | 8/2014 | Zaworotko et al. |
| 2014/0271911 A1 | 9/2014 | Wallace |

FOREIGN PATENT DOCUMENTS

| | | |
|---|---|---|
| WO | WO 2012/007387 | 1/2012 |
| WO | WO 2014/106050 | 7/2014 |

(Continued)

OTHER PUBLICATIONS

Almarsson, Ö. et al. "The A to Z of pharmaceutical cocrystals: a decade of fast-moving new science and patents," *Pharmaceutical Patent Analyst*, 2012, 1(3):313-327.

(Continued)

*Primary Examiner* — Carlos Azpuru
(74) *Attorney, Agent, or Firm* — Saliwanchik, Lloyd & Eisenschenk

(57) ABSTRACT

The invention concerns methods and compositions for treating a neuropsychiatric disorder, wherein the method comprises administering an effective amount of a co-crystal of lithium to a subject in need thereof, wherein the co-crystal comprises lithium, or a pharmaceutically acceptable salt thereof, and an amino acid.

13 Claims, 22 Drawing Sheets

(56) References Cited

FOREIGN PATENT DOCUMENTS

| WO | WO 2014/172650 | 10/2014 |
| WO | WO 2012/170657 | 12/2014 |

OTHER PUBLICATIONS

Almarsson, Ö. et al. "Crystal engineering of the composition of pharmaceutical phases. Do pharmaceutical co-crystals represent a new path to improved medicines?", *Chemical Communications*, 2004, 17:1889-1896.

Aprahamian, I. et al. "Long-term, low-dose lithium treatment does not impair renal function in the elderly: a 2-year randomized, placebo-controlled trial followed by single-blind extension," *Journal of Clinical Psychiatry*, 2014, 75(7):e672-e678.

Basselin, M. et al. "Lithium modifies brain arachidonic and docosahexaenoic metabolism in rat lipopolysaccharide model of neuroinflammation," *Journal of Lipid Research*, 2010, 51(5):1049-1056.

Basselin, M. et al. "Chronic lithium administration attenuates up-regulated brain arachidonic acid metabolism in a rat model of neuroinflammation," *Journal of Neurochemistry*, 2007, 102(3):761-772.

Ciftci, K. et al. "Formulation and in vitro-in vivo evaluation of sustained-release lithium carbonate tablets," *Pharmaceutical Research*, 1990, 7(4):359-363.

Cooper, T.B. et al. "Evaluation of a slow-release lithium carbonate formulation," *American Journal of Psychiatry*, 1978, 135(8):917-922.

Davenport, V.D. "Distribution of parenterally administered lithium in plasma, brain and muscle of rats," *American Journal of Physiology*, 1950, 163(3):633-641.

Desiraju, G.R. "Supramolecular Synthons in Crystal Engineering—A New Organic Synthesis," *Angewandte Chemie*, 1995, 34(21):2311-2327.

Ebadi, M.S. et al. "Pharmacokinetics of lithium and its regional distribution in rat brain," *European Journal of Pharmacology*, 1974, 27(3):324-329.

Emami, J. et al. "Formulation of sustained—release lithium carbonate matrix tablets: influence of hydrophilic materials on the release rate and in vitro-in vivo evaluation," *Journal of Pharmacy & Pharmaceutical Sciences*, 2004, 7(3):338-344.

Food and Drug Administration. "Guidance for Industry: Regulatory Classification of Pharmaceutical Co-Crystals," Center for Drug Evaluation and Research (CDER), Apr. 2013.

Forlenza, O.V. et al. "Neuroprotective Effects of Lithium: Implications for the Treatment of Alzheimer's Disease and Related Neurodegenerative Disorders," *ACS Chemical Neuroscience*, 2014, 5:443-450.

Forlenza, O.V. et al. "Disease-modifying properties of long-term lithium treatment for amnestic mild cognitive impairment: randomised controlled trial," *British Journal of Psychiatry*, 2011. 198(5):351-356.

Frick, L.R. et al. "Microglial dysregulation in psychiatric disease," *Clinical and Developmental Immunology*, 2013, 608-654.

Fukumoto, T. et al. "Chronic lithium treatment increases the expression of brain-derived neurotrophic factor in the rat brain," *Psychopharmacology*, 2001, 158(1):100-106.

Goodwin, F.K. et al. (2003). "Suicide risk in bipolar disorder during treatment with lithium and divalproex," *Journal of the American Medical Association*, 2003, 290(11):1467-1473.

Hernandez, F. et al. "GSK3 and tau: two convergence points in Alzheimer's disease," *Journal of Alzheimer's Disease*, 2013, 33 Suppl 1:S141-4.

Kim, J.S. et al. "Lithium selectively increases neuronal differentiation of hippocampal neural progenitor cells both in vitro and in vivo," *Journal of Neurochemistry*, 2004, 89(2):324-336.

Klein, P.S. et al. "A molecular mechanism for the effect of lithium on development," *Proceedings of the National Academy of Sciences USA*, 1996, 93(16):8455-8459.

Leyhe, T. et al. "Increase of BDNF serum concentration in lithium treated patients with early Alzheimer's disease," *Journal of Alzheimer's Disease*, 2009, 16(3):649-656.

Lippmann, S. et al. "A comparison of three types of lithium release preparations," *Hospital & Community Psychiatry*, 1983, 34(2):113-114.

Livingstone, C. et al. "Lithium: a review of its metabolic adverse effects," *Journal of Psychopharmacology*, 2006, 20(3):347-55.

Mines, M.A. et al. "Regulation of cell survival mechanisms in Alzheimer's disease by glycogen synthase kinase-3," *International Journal of Alzheimer's Disease*, 2011, 2011:861072.

Moulton, B. et al. "From molecules to crystal engineering: supramolecular isomerism and polymorphism in network solids," *Chemical Reviews*, 2001, 101(6):1629-1658.

Musik, I. et al. "The investigation of the possible protective influence of selenium on antioxidant barrier in heart of rats exposed to lithium," *Life Sciences*, 2015, 132:1-5.

Nunes, M.A. et al. "Microdose lithium treatment stabilized cognitive impairment in patients with Alzheimer's disease," *Current Alzheimer Research*, 2013, 10(1):104-107.

Oddo, S. et al. "Triple-transgenic model of Alzheimer's disease with plaques and tangles: intracellular Abeta and synaptic dysfunction," *Neuron*, 2003, 39(3):409-21.

O'Donnell, K.C. et al. "The behavioral actions of lithium in rodent models: leads to develop novel therapeutics," *Neuroscience and Biobehavioral Reviews*, 2007, 31(6):932-62.

Phiel, C.J. etal. Molecular targets of lithium action. *Annual Review of Pharmacology and Toxicology*, 2001, 41:789-813.

Phiel, C.J. et al. "GSK-3α regulates production of Alzheimer's disease amyloid-β peptides," *Nature*, 2003, 423(6938):435-439.

Rao, J.S. et al. "Increased excitotoxicity and neuroinflanunatory markers in postmortem frontal cortex from bipolar disorder patients," *Molecular Psychiatry*, 2010, 15(4):384-392.

Rezai-Zadeh, K. et al. "Apigenin and luteolin modulate microglial activation via inhibition of STAT1-induced CD40 expression," *Journal of Neuroinflammation*, 2008, 5:41.

Ryves, W.J. et al. "Lithium inhibits glycogen synthase kinase-3 by competition for magnesium," *Biochemical and Biophysical Research Communications*, 2001, 280(3):720-725.

Schou, M. et al. "Pharmacological and clinical problems of lithium prophylaxis," *British Journal of Psychiatry*, 1970, 116(535):615-619.

Serhan, C.N. et al. "Resolvins: a family of bioactive products of omega-3 fatty acid transformation circuits initiated by aspirin treatment that counter proinflammation signals," *The Journal of Experimental Medicine*, 2002, 196(8):1025-1037.

Sheldrick, G.M. et al. "SADABS. Program for Empirical Absorption Correction," University of Göttingen, Göttingen, Germany, 1996.

Shorter, E. "The history of lithium therapy," *Bipolar Disorders*, 2009, 11 Suppl 2:4-9.

Smith, A.J. et al. "Improving Lithium Therapeutics by Crystal Engineering of Novel Ionic Cocrystals," *Molecular Pharmaceutics*, 2013, 10(12):4728-4738.

Smith, A. et al. "Nanolipidic particles improve the bioavailability and α-secretase inducing ability of epigallocatechin-3-gallate (EGCG) for the treatment of Alzheimer's disease," *International Journal of Pharmaceutics*, 2010, 389(1-2):207-212.

Stolk, P. et al. "Is aspirin useful in patients on lithium? A pharmacoepidemiological study related to bipolar disorder," *Prostaglandins, Leukotrienes, and Essential Fatty Acids*, 2010, 82(1):9-14.

Tan, J. et al. "Interferon-gamma-inducing factor elicits antitumor immunity in association with interferon-gamma production," *Journal of Immunotherapy*, 1998, 21(1):48-55.

Thies-Flechtner, K. et al. "Effect of prophylactic treatment on suicide risk in patients with major affective disorders. Data from a randomized prospective trial," *Pharmacopsychiatry*, 1996, 29(3):103-107.

(56) References Cited

OTHER PUBLICATIONS

Townsend, K.P. et al. "CD40 signaling regulates innate and adaptive activation of microglia in response to amyloid β-peptide," *European Journal of Immunology*, 2005, 35(3):901-910.

Vassar, R. et al. "β-secretase cleavage of Alzheimer's amyloid precursor protein by the transmembrane aspartic protease BACE," *Science*, 1999, 286(5440):735-741.

Wang, J. et al. "Anti-Inflammatory Drugs and Risk of Alzheimer's Disease: An Updated Systematic Review and Meta-Analysis," *Journal of Alzheimer's Disease*, 2015, 44(2):385-396.

Ye, S.M. et al. "An age-related decline in interleukin-10 may contribute to the increased expression of interleukin-6 in brain of aged mice," *Neuroimmunomodulation*, 2001, 9(4):183-192.

Yu, F. et al. "Lithium ameliorates neurodegeneration, suppresses neuroinflammation, and improves behavioral performance in a mouse model of traumatic brain injury," *Journal of Neurotrauma*, 2012, 29(2):362-374.

Yuskaitis, C.J. et al. "Glycogen synthase kinase-3 regulates microglial migration, inflammation, and inflammation-induced neurotoxicity," *Cell Signal*, 2009, 21(2):264-273.

Zhu, Y. et al. "CD45 deficiency drives amyloid-β peptide oligomers and neuronal loss in Alzheimer's disease mice," *Journal of Neuroscience*, 2011, 31(4):1355-1365.

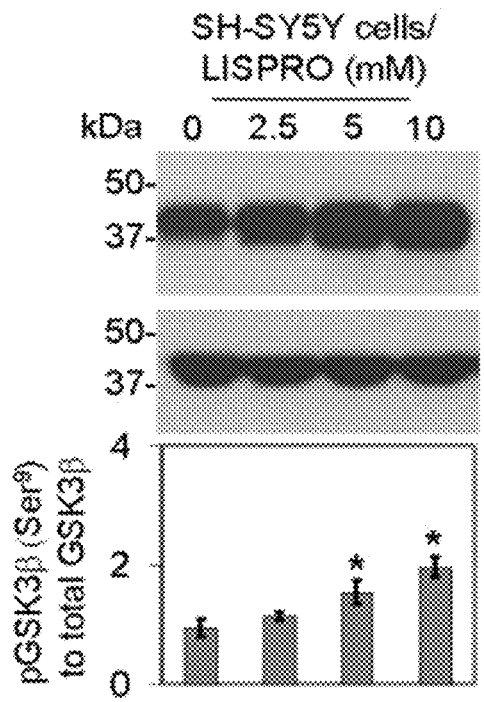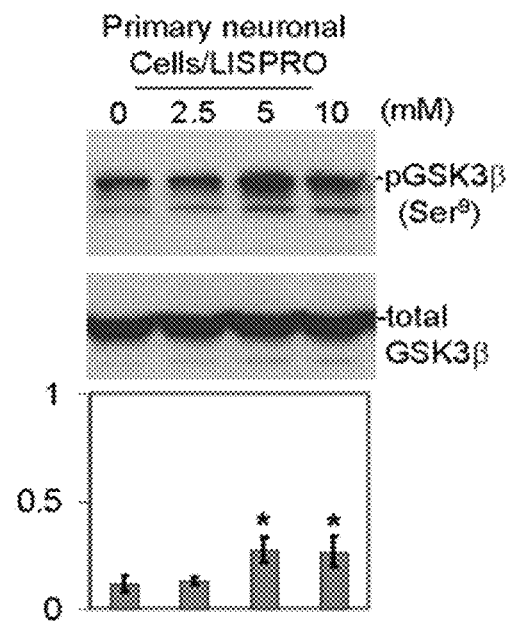
FIG. 2A  FIG. 2B
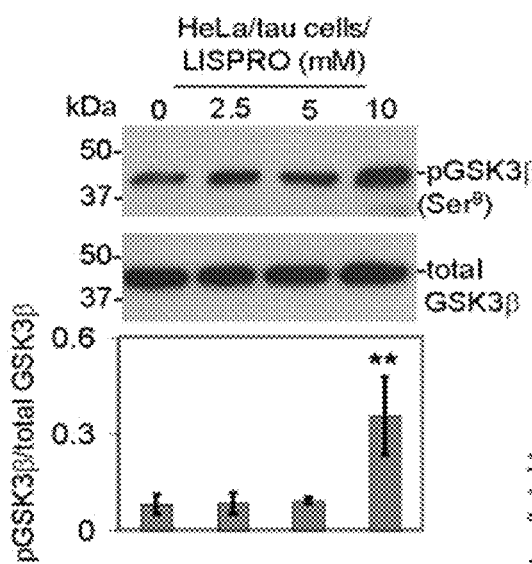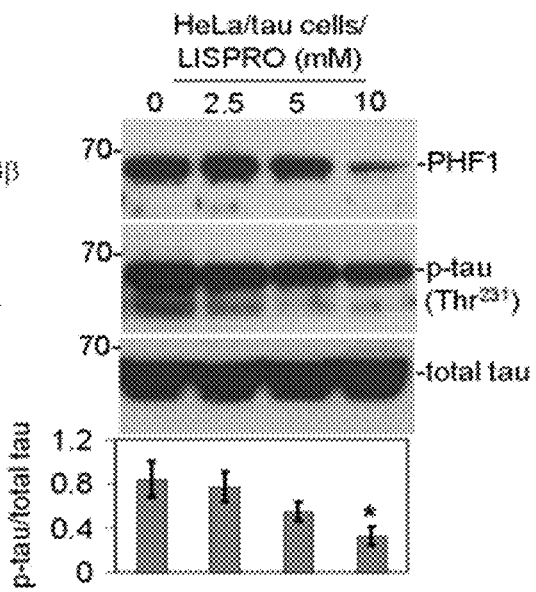
FIG. 3A  FIG. 3B

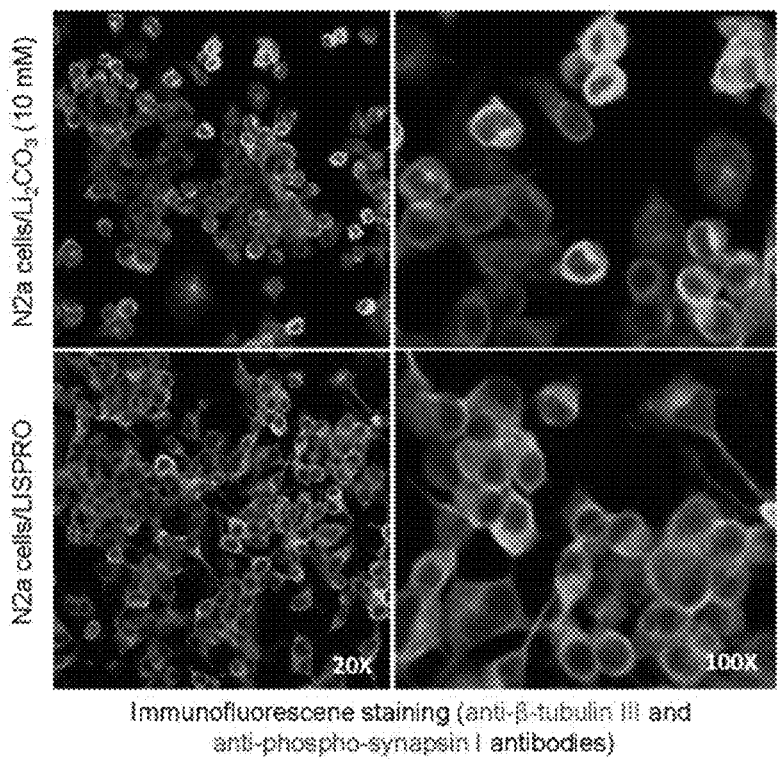
FIG. 5A
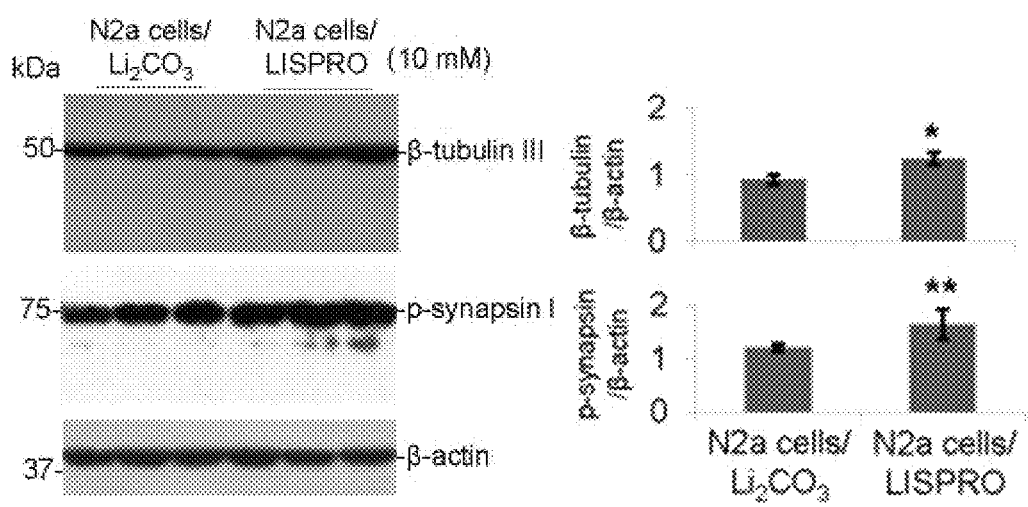
FIG. 5B
FIG. 5C

FIG. 6A
FIG. 6B
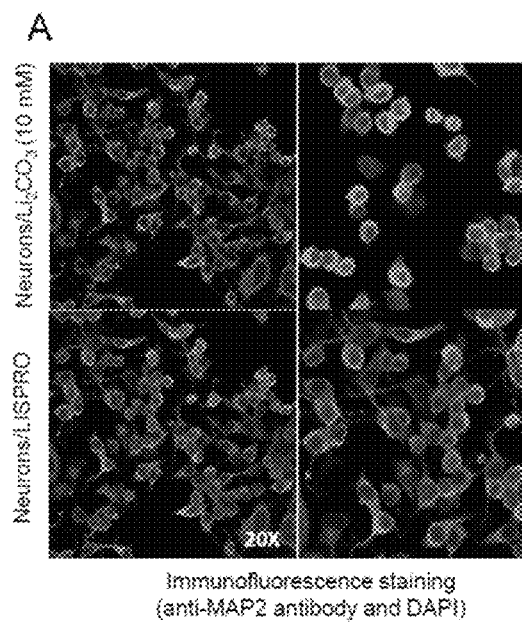
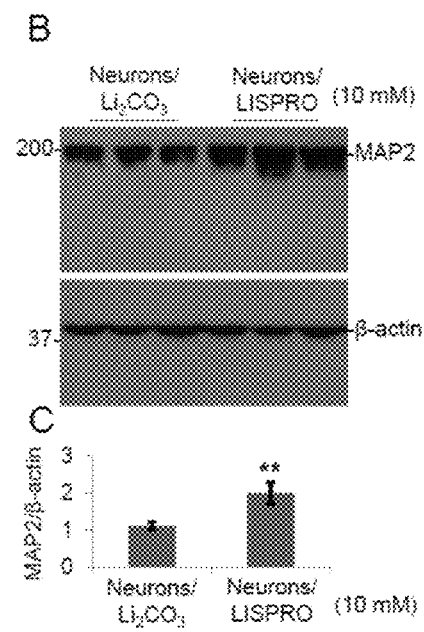
FIG. 6C
FIG. 6D
FIG. 6E
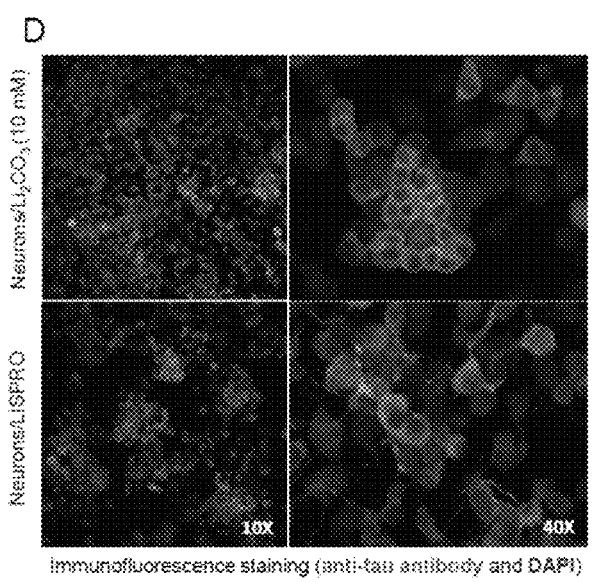
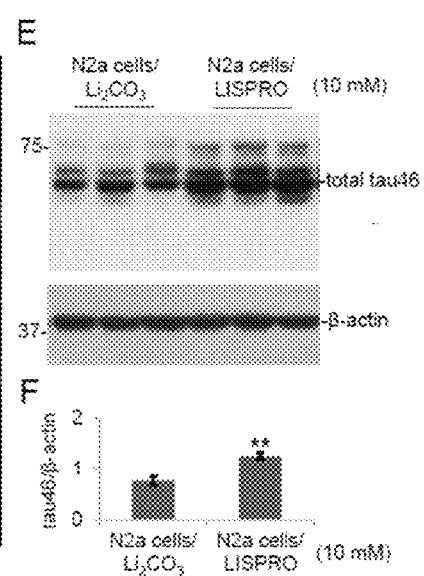
FIG. 6F

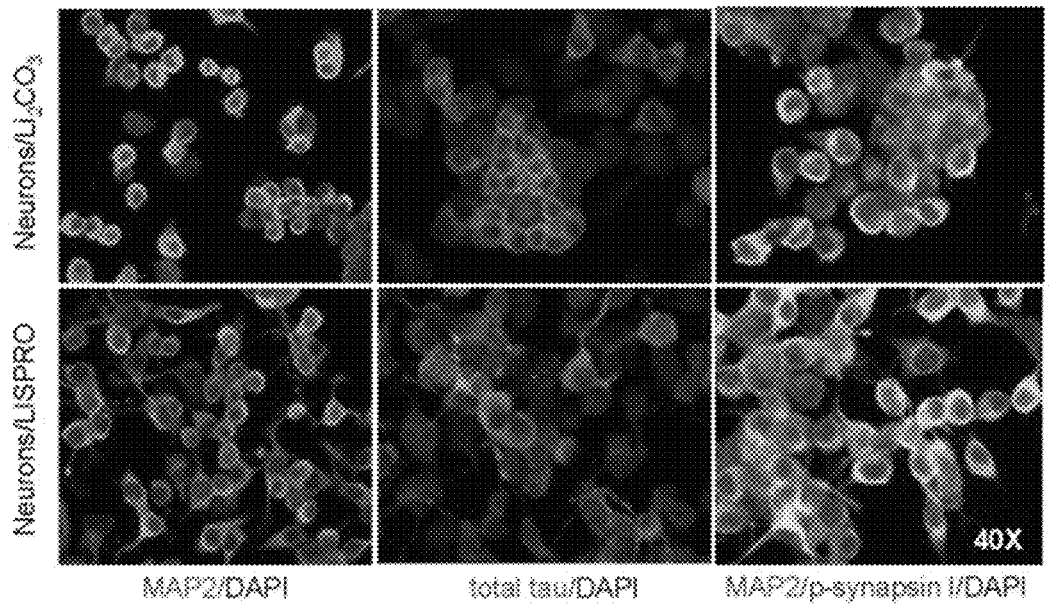
FIG. 17A
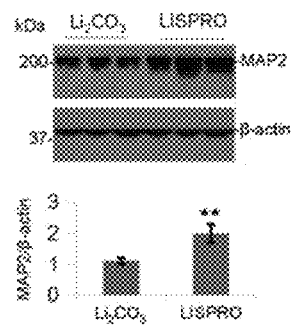    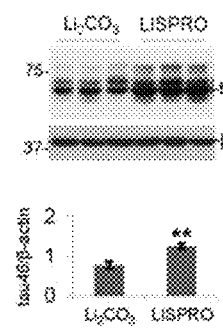    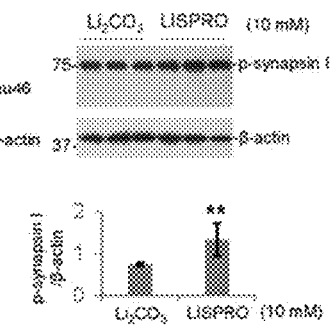
FIG. 17B-1    FIG. 17B-2    FIG. 17B-3

FIG. 24A-1
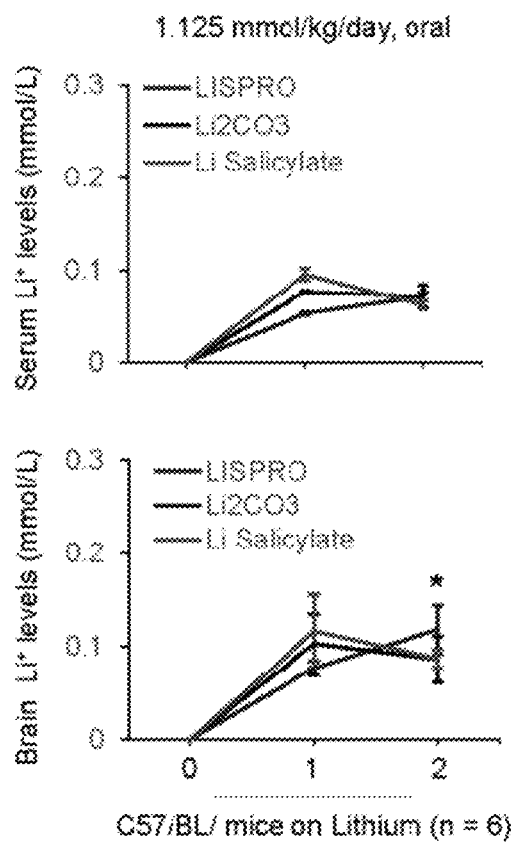
FIG. 24A-2
FIG. 24B-1
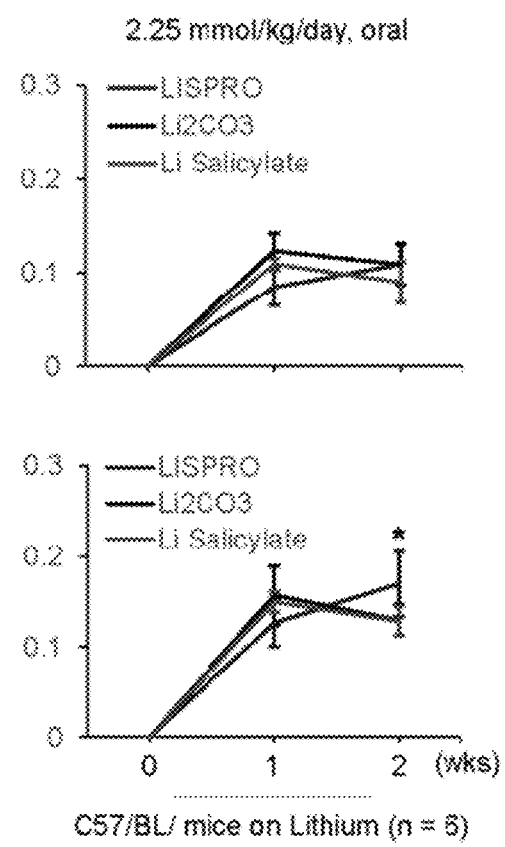
FIG. 24B-2

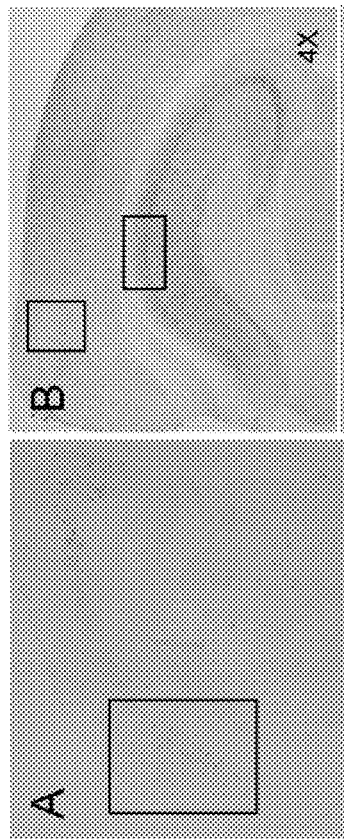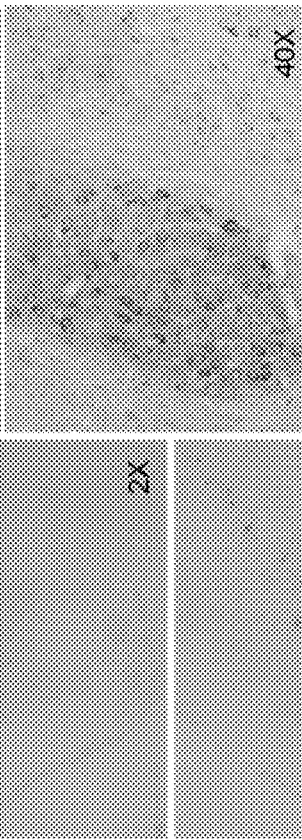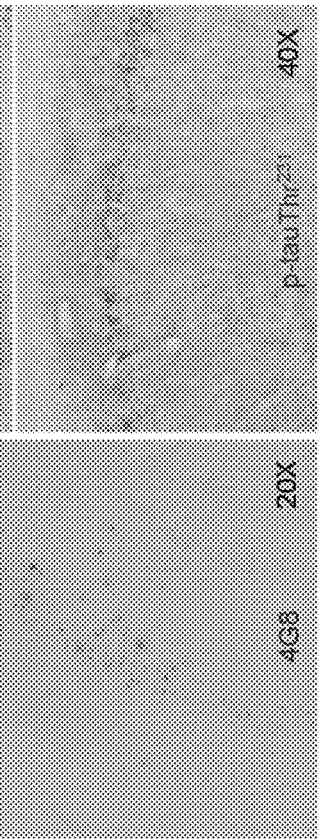
FIG. 26A-1  FIG. 26A-2  FIG. 26B-1  FIG. 26B-2  FIG. 26B-3

LITHIUM CO-CRYSTALS AND AN ADDITIONAL NEUROPSYCHIATRIC AGENT FOR TREATMENT OF NEUROPSYCHIATRIC DISORDERS

CROSS-REFERENCE TO RELATED APPLICATION

The present application claims the benefit of U.S. Provisional Application Ser. No. 62/165,238, filed May 22, 2015, which is hereby incorporated by reference herein in its entirety, including any figures, tables, nucleic acid sequences, amino acid sequences, or drawings.

BACKGROUND OF THE INVENTION

Lithium salts have a long history of human consumption beginning in the 1800s. In psychiatry, they have been used to treat mania and as a prophylactic for depression since the mid-20$^{th}$ century (Shorter, 2009). Today, lithium salts are used as a mood stabilizer for the treatment of bipolar disorder, as well as for other psychiatric indications off-label. For example, lithium is the only drug that consistently reduces suicidality in patients with neuropsychiatric disorders (Thies-Flechtner et al., 1996; Goodwin et al., 2003). Despite these effective medicinal uses, current FDA-approved lithium pharmaceutics (lithium carbonate and lithium citrate) are plagued with a narrow therapeutic window that requires regular blood monitoring of plasma lithium levels and blood chemistry by a clinician to mitigate adverse events. Because conventional lithium salts (carbonate and citrate) are eliminated relatively quickly, multiple administrations throughout the day are required to safely reach therapeutic plasma concentrations.

Evidence suggests that lithium may be efficacious for the treatment of Alzheimer's disease. As depicted in FIG. 12, several mechanisms may underlie lithium's potential efficacy for Alzheimer's disease (O'Donnell and Gould, *Neurosci Biobehav Rev.*, 2007; 31(6): 932-962). First, it exerts neuroprotective effects, in part, by increasing brain-derived neurotrophic factor (BDNF). Indeed, chronic lithium treatment has been shown to increase the expression of BDNF in rats (Fukumoto et al., 2001) and humans (Leyhe et al., 2009). This increase in BDNF activity can lead to restoration of learning and memory through promotion of neurogenesis and long-term potentiation (LTP). Another neuroprotective mechanism of lithium is attenuation of the production of inflammatory cytokines like IL-6 and nitric oxide (NO) in activated microglia (Yuskaitis and Jope, 2009). This is particularly important since aberrant microglial function is a common finding in AD (Frick et al., 2013). Lithium has also been found to inhibit certain enzymes in a noncompetitive manner by displacing the required divalent cation, magnesium (Phiel and Klein, 2001). One of these enzymes, glycogen synthase kinase-3 beta (GSK3β), has important implications in Alzheimer's disease. GSK3β was first identified as the molecular target of lithium by Klein and Melton (Klein and Melton, 1996). It is a ubiquitously expressed serine/threonine kinase that is key in the pathogenesis of Alzheimer's disease. The enzyme phosphorylates tau in most serine and threonine residues hyperphosphorylated in the paired helical filaments. Moreover, GSK3 activity contributes both to amyloid-β (Aβ) production and AP-mediated neuronal cell death (Mines et al., *J Biol Chem.* 2011 Jun. 10; 286 (23):20797-811. Aβ is derived from amyloid precursor protein (APP) by sequential proteolysis, catalyzed by the aspartyl protease BACE followed by presenilin-dependent γ-secretase proteolysis (Vasser et al., *Science,* 1999 Oct. 22; 286(5440):735-41).

It has been demonstrated that therapeutic concentrations of lithium blocked the production of Aβ peptides by interfering with APP cleavage at the γ-secretase step, without inhibition of Notch processing (Phiel C J et al., *Nature,* 2003 May 22; 423(6938):435-9). Lithium also blocked the accumulation of Aβ in the brains of mice overexpressing APP by inhibition of GSK3α, implicating its requirement for maximal processing of APP (Forlenza O V et al., *ACS Chem. Neurosci.,* 2014, 5 (6), pp 443-450). Since GSK3α also phosphorylates tau protein, inhibition of GSK3α offers a new approach to reduce the formation of both amyloid plaques and neurofibrillary tangles (Phiel C J et al., 2003). In further support, mice with conditional overexpression of GSK3 in forebrain neurons recapitulate aspects of Alzheimer's disease neuropathology such as tau hyperphosphorylation, apoptotic neuronal death, reactive astrocytosis, and spatial learning deficits (Hernandez F et al., *J Alzheimers Dis.* 2013; 33 Suppl 1:S141-4). Further transgene shutdown in that animal model leads to normal GSK3 activity, normal phospho-tau levels, diminished neuronal death, and amelioration of cognitive deficits, thus further supporting the potential of the GSK3 inhibitor, lithium, for Alzheimer's disease therapeutics. In addition, combined transgenic mice overexpressing GSK3β with transgenic mice expressing tau with a triple FTDP-17 mutation develop prefibrillar tau-aggregates (Hernandez F. et al., 2013), which was averted by lithium as well.

BRIEF SUMMARY OF THE INVENTION

The present invention concerns use of a co-crystal of lithium (lithium co-crystal) for treatment of a neuropsychiatric disorder. In one aspect, the treatment method comprises administering an effective amount of a co-crystal of lithium to a subject in need thereof, wherein the co-crystal comprises lithium, or a pharmaceutically acceptable salt thereof, and an amino acid. In some embodiments, the salt is lithium salicylate or lithium hydroxide. In some embodiments, the amino acid is L-proline. In one embodiment, the co-crystal comprises lithium salicylate and L-proline.

In some embodiments, the neuropsychiatric disorder is a neurodegenerative disorder, such as Alzheimer's disease (AD), Parkinson's disease (PD), or amyotrophic laterals sclerosis (ALS). In some embodiments, the neuropsychiatric disorder is a mood disorder (e.g., bipolar disorder, depressive disorder), schizoaffective disorder, tic disorder (e.g., Tourette's syndrome), or suicidality.

A co-crystal of lithium salicylate and L-proline (LISPRO) exhibited plateau-like pharmacokinetics compared to the problematic peak and trough pharmacokinetics of other lithium forms (Smith A J et al., *Mol. Pharmaceutics* 2013, 10, 4728-4738). Empirical evidence suggests that the salicylate anion in LISPRO might be therapeutically synergistic with lithium for the treatment of bipolar disorder. For example, a recent pharmacoepide miological study suggests that low doses of acetylsalicylic acid (aspirin) might be beneficial as an adjunct treatment with lithium salts for the treatment of bipolar disorder (Stolk et al., 2010).

The anion in lithium salicylate, salicylic acid, is the primary bioactive metabolite of aspirin. Stolk et al. reported that low-dose aspirin produced significant reduction in the relative risk of clinical deterioration in subjects on lithium and that this was not the case with other NSAIDs and glucocorticoids (Stolk et al., 2010). Without being limited by theory, the inventors propose that this is due to synergistic anti-inflammatory actions of lithium and acetylsalicylic acid by increasing the brain concentrations of 17-OH-DHA, an anti-inflammatory brain DHA metabolite. This hypothesis is supported by previous studies that indicated neuroinflammation in BD (Rao et al., 2010), that aspirin increases 17-OH-DHA (Serhan et al., 2002), and that lithium reduces neuroinflammation (Basselin et al., 2007; Basselin et al., 2010; Yu et al., 2012).

In view of the potential for synergistic effects due to the biologically non-inert anion, salicylic acid, efficacy testing of LISPRO was conducted, and is described herein.

BRIEF DESCRIPTION OF THE DRAWINGS

(FIG. 1A) N2a/APPwt cells were treated with LISPRO at 0, 2.5, 5 and 10 mM as indicated for 12 h followed by analysis of $A\beta_{40, 42}$ peptides secreted in the cell culture media by AO ELISA. The AO ELISA results are represented as the mean±SD of $A\beta_{40}$ or $A\beta_{42}$ (ng/ml) in cell culture media after LISPRO treatment. These results are representative of three independent experiments with n=3 for each condition (*p<0.05). To examine whether LISPRO can affect Notch processing, the inventors co-transfected N2a cells expressing wild-type human APP (N2a/APPwt) with Notch-4E vector. N2a/APPwt/Notch-4E cells were plated at $8\times10^5$/well in 6-well dishes and treated with LISPRO or DFK-167 (positive control for Notch cleavage) at different doses as indicated for 5 hours. The cell lysates were routinely prepared from these cells for Western blot (WB) analysis. (FIG. 1B) WB with both c-myc antibody (9E10, ABCAM®) and cleaved Notch antibody (Val1744, CELL SIGNALING TECHNOLOGY®) showed that LISPRO treatment did not inhibit Notch cleavage compared to DFK-167. FIGS. 1A and 1B are described further in Example 2.

FIGS. 2A and 2B. Treatment with LISPRO dose-dependently increases inhibitory GSK3β (Ser9) phosphorylation in SH-SY5Y cells and primary neuronal cells. Human neuroblastoma (SH-SY5Y) cells (FIG. 2A) and primary neuronal cells (FIG. 2B) were treated with LISPRO at the indicated concentrations for 12 hours. Cell lysates were prepared and subjected to WB analysis with specific anti-phospho-GSK3β (Ser9) and total GSK3β antibodies. As shown, phosphorylated GSK3β (Ser9) [pGSK3β (Ser9)] was notably elevated following LISPRO treatment in both SH-SY5Y and primary neuronal cells. Below each figure panel, densitometry analysis shows the band density ratio of pGSK3β (Ser9) to total GSK3β. WB results are representative of three independent experiments. A t-test revealed a significant difference in the ratio of pGSK3β (Ser9) to total GSK3β for both SH-SY5Y cells and differentiated neuronal cells treated with either 2.5, 5 or 10 mM LISPRO compared to control (0 mM) (*p<0.05).

FIGS. 3A and 3B. Treatment with LISPRO increases inhibitory GSK3β (Ser9) phosphorylation and decreases tau phosphorylation in HeLa/tau cells. Human tau stably transfected HeLa cells (HeLa/tau cells) were treated with LISPRO at the indicated concentrations for 12 hours. Cell lysates were prepared for WB analysis of both total and phosphorylated levels of GSK3β and tau. (FIG. 3A) Phosphorylation status of GSK3β [pGSK3β (Ser9)] was detected by anti-phosphoGSK3β (Ser9) antibody. (FIG. 3B) Phosphorylation status of tau was detected by anti-phospho-tau [p-tau (Thr231)] and PHF1 antibodies (kindly provided by Dr. Peter Davies). Total tau (phosphorylated and non-phosphorylated) was detected by tau-46. WB results are representative of two independent experiments for pGSK3β (Ser9) and total GSK3β, and three experiments respectively for PHF1, p-tau (Thr231) and total tau. Densitometry analysis shows the band density ratio of pGSK3β (Ser9) to total GSK3β as well as p-tau (Thr231) to total tau shown below each figure panel. A t-test revealed a significant increase in the ratio of pGSK3β (Ser9) to total GSK3β and decrease in p-tau to total tau for HeLa/tau cells treated with either 2.5, 5 or 10 mM LISPRO compared to control (0 mM) (*p<0.05; **p<0.01). $A\beta_{40, 42}$ peptides were undetectable by AO ELISA of the conditioned media from HeLa/tau cells with or without LISPRO (data not shown). FIGS. 3A and 3B are described further in Example 3.

FIGS. 4A-C are described further in Example 11.

FIGS. 5A-5C. LISPRO markedly promotes neuronal cell differentiation. (FIG. 5A) Wild-type mouse neuroblastoma (N2a cells) were plated in 8-well slide chambers ($10^6$/well), incubated overnight, and treated with LISPRO or appropriate controls (including $Li_2CO_3$, LiCl and L-proline, Sigma) at 10 mM (as optimized by pilot studies) for 24 hours. This concentration was optimized in the pilot study. These cells were then permeabilized with 0.05% Triton X-100 for 5 minutes, washed and stained with mouse anti-β-tubulin III monoclonal antibody (STEMCELL™) and rabbit anti-phospho-Synapsin I ($Ser^{62}$, $Ser^{67}$) polyclonal antibody (EMD Millipore) overnight at 4° C. ALEXA FLUOR® 488 Goat anti-mouse IgG (green) and ALEXA FLUOR® 594 Donkey anti-rabbit IgG (red, Life Technologies) were used to detect β-tubulin III and phospho-synapsin I signals, respectively. Confocal images were taken by Olympus fluoview FV1000 laser scanning confocal microscope (Tokyo, Japan). (FIG. 5B) In parallel, additional N2a cells were cultured in 6-well plates ($3\times10^6$/well), treated with LISPRO, $Li_2CO_3$, LiCl or L-proline at 10 mM, lysed with cell lysis buffer and then subjected to western blot (WB) analysis of β-tubulin III, p-synapsin I or β-actin. (FIG. 5C) The band density ratios of β-tubulin and phospho-synapsin I to β-actin are presented as mean±S.D. These data are representative of three independent experiments with similar results (*P<0.05; **P<0.005). There was no notable or significant difference in β-tubulin III and phospho-synapsin I immunofluorescence and WB analysis between $Li_2CO_3$, LiCl or L-proline (P>0.05). FIGS. 5A-C are described further in Example 8.

FIGS. 6A-6F. LISPRO notably enhances neuronal stem cell differentiation. (FIGS. 6A and 6D) Murine neuronal stem cells (ATCC) were plated in 8-well slide chambers ($10^6$/well), incubated overnight and treated with LISPRO, $Li_2CO_3$, LiCl or L-proline at 10 mM for 48 hours. These cells were then permeabilized, washed and stained with mouse anti-MAP2 monoclonal antibody (EMD Millipore) or mouse anti-total tau (tau46) antibody overnight at 4° C. ALEXA FLUOR® 488 Goat anti-mouse IgG (green) was used to detect MAP2 and total tau and DAPI (Life Technologies) was used to detect nuclear DNA. Confocal images were taken by Olympus fluoview FV1000 laser scanning confocal microscope. (FIGS. 6B and 6E) In parallel, additional neuronal stem cells were cultured in 6-well plates ($3 \times 10^6$/well), treated with LISPRO, $Li_2CO_3$, LiCl or L-proline, lysed with cell lysis buffer and analyzed by WB. (FIGS. 6C and 6F) The band density ratios of MAP2 to β-actin and total tau to β-actin are presented as mean±S.D. These data are representative of two independent experiments with similar results (**P<0.005). Note that there was no significance difference in MAP2 and total tau immunofluorescence and WB analysis between $Li_2CO_3$, LiCl or L-proline (P>0.05).

FIGS. 17A and B-1 to B-3 show that LISPRO enhances murine neuronal stem cell differentiation (described in Example 9).

FIGS. 22A, 22B-1, and 22B-2 show that LISPRO does not increase COX2 expression in Tg2576 mice following 8-week-treatment (described in Example 15).

FIGS. 24A-1, A-2, B-1, and B-2 show long-term serum and brain pharmacokinetics of LISPRO, lithium salicylate, and lithium carbonate (described in Example 17).

FIGS. 26A-1, A-2, and B-1 to B-3 show 3XTg-AD mouse brain tumor sections stained with anti-Aβ antibody (4G8), shown in FIGS. 26A-1 (2× magnification) and 26A-2 (20× magnification) or anti-phospho-tau ($Thr^{231}$) antibody [p-tau ($Thr^{231}$), shown in FIGS. 26B-1 (4× magnification, 26B-2 (40× magnification), and 26B-3 (40× magnification).

DETAILED DESCRIPTION OF THE INVENTION

Figure 1A:
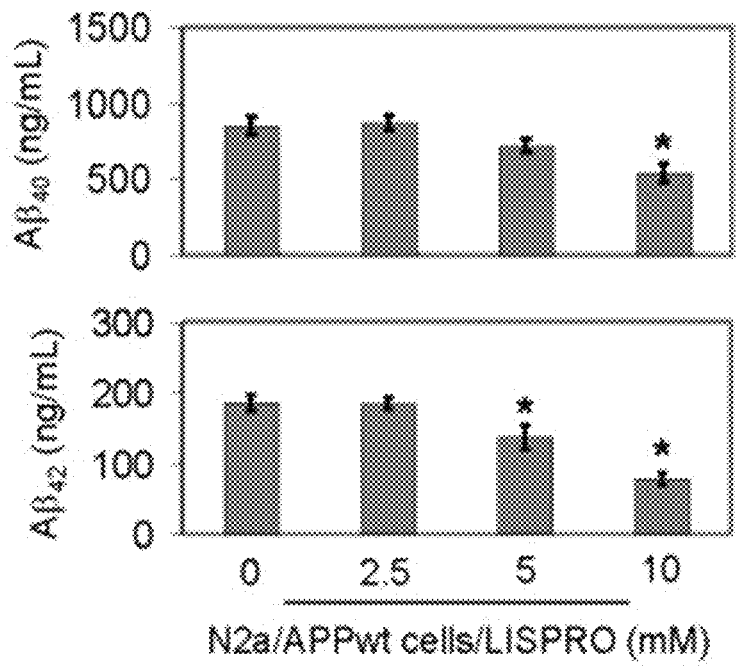
FIGS. 1A and 1B. The co-crystal of lithium salicylate and L-proline (LISPRO) does not inhibit Notch processing, but reduces Aβ generation.

The present invention concerns a method for treating a neuropsychiatric disorder, comprising administering an effective amount of a co-crystal of lithium to a subject in need thereof, wherein the co-crystal comprises: lithium, or a pharmaceutically acceptable salt thereof, as a molecular or ionic active pharmaceutical ingredient (API), and an amino acid as a co-crystal former that is a solid under ambient conditions.

Various amino acids may be used as co-crystal formers for the lithium co-crystals, as long as they are not toxic to the subject as an administered lithium co-crystal. The amino acid may be an essential amino acid (histidine, isoleucine, leucine, lysine, methionine, phenylalanine, threonine, tryptophan, or valine) or a non-essential amino acid (alanine, arginine, asparagine, aspartic acid, cysteine, glutamic acid, glutamine, glycine, pyrrolysine, proline, selenocysteine, serine, or tyrosine). The amino acid may be cyclic (such as proline), aliphatic (glycine, alanine, valine, leucine, isoleucine), hydroxyl or sulfur/selenium-containing (serine, cysteine, selenocysteine, threonine, methionine), aromatic (phenylalanine, tyrosine, tryptophan), basic (histidine, lysine, arginine), or acidic or their amide (aspartate, glutamate, asparagine, glutamine). The amino acid may be a non-standard amino acid or non-proteinogenic (non-coded) amino acid, such as L-DOPA, GABA, 2-aminobutyric acid, dehydralanine, δ-carboxyglutamic acid, formylmethionine, selenocysteine, and pyrrolyseine. Any organic compound with an amine (—NH$_2$) and a carboxylic acid (—COOH) functional group can be considered an amino acid, and may potentially be used for the lithium co-crystal. The proteinogenic amino acids are small subset of this group that possess central carbon atom (α- or 2-) bearing an amino group, a carboxyl group, a side chain and an α-hydrogen levo conformation, with the exception of glycine, which is achiral, and proline, whose amine group is a secondary amine. The amino acid may be a non-coded amino acid that is nonetheless found in proteins, such as carboxyglutamic acid, hydroxyproline, hypusine, or pyroglutamic acid. In some embodiments, the amino acid is a zwitterionic co-former. Zwitterionic co-formers are characterized by the presence of strong charge-assisted hydrogen bonds. Each co-crystal may have a single amino acid or multiple (two or more) different amino acid.

The amino acids may be in levorotatory form (l-amino acid) or dextrorotatory form (d-amino acid).

Various salts of lithium may be used as APIs for the lithium co-crystals. Each co-crystal may have a single salt form, or multiple (two or more) salt forms of lithium. Salicylic acid and derivatives such as acetylsalicylic acid (aspirin) are particularly useful, both for the pharmacokinetic advantage and the "co-drug" synergistic effects for the treatment of Alzheimer's disease and (AD) other neuropsychiatric disorders.

In some embodiments, the salt is a derivative of salicyclic acid. In some embodiments the salt is an ester derivative such as acetylsalicylic acid or methyl salicylate. Other examples of salicylic acid derivatives that may be used are disclosed in Weizmann C H et al., "Derivatives of Salicylic Acid", *J. Org. Chem.*, 13(6):796-799; and Clissold S P, "Aspirin and related derivatives of salicylic acid", Drugs, 1986, 32 Suppl 4: 8-26, which are each incorporated herein by reference in their entirety.

In some embodiments, the salt is lithium salicylate, lithium hydroxide, lithium nicotinate, lithium citrate, lithium sulfate, lithium oxybutyrate, lithium orotate, or lithium carbonate. The lithium salt may be one described in Frost R E and Messiha F S, *Brain Res Bull*, 1983, August, 11(2) 219-31, which is incorporated herein by reference in its entirety.

In some embodiments, the amino acid is proline. In some embodiments, the amino acid is L-proline. In one embodiment, the co-crystal comprises lithium salicylate and proline (l-proline or d-proline). In one embodiment, the co-crystal comprises lithium salicylate and l-proline, and the neuropsychiatric disorder is Alzheimer's disease (early-onset, late-onset, or familial Alzheimer's disease (FAD)) or a mild-cognitive impairment (MCI).

In some embodiments, the neuropsychiatric disorder is a neurodegenerative disorder, such as Alzheimer's disease (AD), Parkinson's disease (PD), Huntington's disease (HD), or amyotrophic laterals sclerosis (ALS). In some embodiments, the neuropsychiatric disorder is mood disorder (e.g., bipolar disorder, depressive disorder), schizoaffective disorder, tic disorder (e.g., Tourette's syndrome), or suicidality (e.g., suicidal ideation or suicidal behavior). Subjects may have one or a combination of two or more neurodegenerative disorders, mood disorders, or other neuropsychiatric disorders.

The psychiatric disorders that may be treated with lithium co-crystals may be acute or chronic, early-stage, or late-stage. For example, in the case of Alzheimer's disease (AD), the disorder may be early-onset, late-onset, or familial Alzheimer's disease (FAD). The neurodegenerative disorder may be a mild-cognitive impairment (MCI), which is the stage between normal forgetfulness due to aging, and the development of Alzheimer's disease.

Optionally, the methods may further comprise identifying the subject as having a neuropsychiatric disorder prior to administration of the lithium co-crystal (e.g., through diagnosis by a clinician or appropriately licensed health care professional) and/or conducting one or more tests on the subject one or more times after administration to determine whether there has been improvement in the condition. The tests may be behavioral diagnostics and/or assays for biomarkers, or other tests known and used by those of ordinary skill in the art.

Aspects of the invention include methods for delivery of lithium and/or achieving one or more of the following in a subject by administering an effective amount of a lithium co-crystal of the invention or composition comprising the co-crystal through any route of delivery, including those disclosed herein: increasing brain-derived neurotrophic factor (BDNF) activity, attenuating of interleukin-6 and/or nitric oxide in microglia, reducing amyloid beta (Aβ) generation, increasing inhibitory GSK3β (Ser9) phosphorylation (e.g., in neuronal cells), decreasing tau phosphorylation (e.g., in neuronal cells), increasing brain 17-hydroxydocosahexaenoic acid (17-OH-DHA), inhibiting microglial activation-induced by IFNγ and CD40 signaling, enhancing microglial phagocytosis of Aβ, promoting or enhancing neuronal stem cell differentiation, or promoting autophagy.

As used herein, the term "subject" refers to a human or non-human mammal. The subject may be any age or gender. Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

As used herein, a "pharmaceutical composition" refers to a preparation of one or more of the active ingredients described herein (e.g., lithium co-crystal) with other components such as physiologically suitable carriers and excipients. The purpose of a pharmaceutical composition is to facilitate administration of an agent to the subject.

As used herein, the term "active ingredient" refers to the lithium co-crystal accountable for the intended biological effect.

As used herein, the phrases "physiologically acceptable carrier" and "pharmaceutically acceptable carrier," which may be used interchangeably, refer to a carrier or a diluent that does not cause significant irritation to the subject and does not abrogate the biological activity and properties of the administered agent.

As used herein, the term "excipient" refers to an inert substance that may be included in a pharmaceutical composition to further facilitate administration of an active ingredient. Examples of excipients include, but are not limited to, calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration for the lithium co-crystals, and pharmaceutical compositions comprising them, may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, topical, transdermal, or intraocular injections.

Alternately, one may administer the lithium co-crystals or pharmaceutical composition in a local rather than systemic manner, for example, via delivery of the pharmaceutical composition directly into a tissue region of a subject (e.g., intracranially).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. Co-crystals of lithium may be produced using the methods described in Smith A J et al. (*Mol. Pharmaceutics* 2013, 10, 4728-4738), which is incorporated herein by reference in its entirety. Characterization of the structure and properties of embodiments of lithium co-crystals that may be used in the invention are described in Smith A J et al. and in FIGS. 9A-B, 10, and 11 herein.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated may be used in the formulation. Such penetrants are generally known in the art.

For oral administration, the pharmaceutical composition can be formulated readily by combining the active ingredient(s) (e.g., lithium co-crystal) with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added. The pharmaceutical composition may be an edible or drinkable composition intended for ingestion.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, an "effective amount" means an amount of active ingredients (e.g., lithium co-crystal) effective to prevent, delay onset of, alleviate, or ameliorate one or more symptoms of a neuropsychiatric disorder (e.g., a neurodegenerative disorder such as Alzheimer's disease), e.g., by increasing brain-derived neurotrophic factor (BDNF) activity, attenuating of interleukin-6 and/or nitric oxide in microglia, reducing Aβ generation, increasing inhibitory GSK3β (Ser9) phosphorylation, decreasing tau phosphorylation, increasing brain 17-hydroxy-docosahexaenoic acid (17-OH-DHA), inhibiting microglial activation-induced by IFNγ and CD40 signaling, enhancing microglial phagocytosis of Aβ, promoting or enhancing neuronal stem cell differentiation, promoting autophagy, or by a different mechanism.

Determination of an effective amount is well within the capability of those skilled in the art, especially in light of the detailed disclosure provided herein. For administration, the lithium co-crystals may, in one embodiment, be administered in a formulation containing 0.001% to 70% per weight of the co-crystal, preferably between 0.01% to 70% per weight of the co-crystal, even more preferred between 0.1% and 70% per weight of the co-crystal. In one embodiment, a suitable amount of co-crystal administered is in the range of 0.01 mg/kg body weight to 1 g/kg body weight.

Lithium co-crystal-containing pharmaceutical compositions may be in the form of a sustained release system. Suitable examples of sustained release systems include semipermeable matrices of solid hydrophobic polymers containing the compound of the invention, which matrices may be in form of shaped articles, e.g., films or microcapsules.

For any preparation used in the methods of the invention, the dosage or the effective amount can be estimated initially from in vitro and cell culture assays (e.g., proliferation assay as further described herein below). For example, a dose can be formulated in animal models to achieve a desired concentration or titer. Such information can be used to more accurately determine useful doses in humans.

The methods of the invention may further comprise administering an additional agent for treating the neuropsychiatric disorder before, during, or after the administration of the lithium co-crystal. The additional agent may be administered to the subject in the same composition as the lithium co-crystal or in separate compositions administered by the same or different anatomical routes. Accordingly, the compositions of the invention may include one or more additional agents as well.

In some embodiments, the additional agent is an anti-depressant, anti-convulsant, or mood stabilizer, or a combination of two or more of the foregoing.

In some embodiments, the additional agent is a selective serotonin reuptake inhibitor (SSRI), serotonin-noroepinephrine reuptake inhibitor (SNRI), serotonin antagonist and reuptake inhibitor (SARI), monamine oxidase inhibitor (MAOI), carboxamide, fructose derivative, triazine, or a combination of two or more of the foregoing.

In some embodiments, the disorder is a neurodegenerative disease such as Alzheimer's disease, and the additional agent is selected from the group consisting of a cholinesterase inhibitor (e.g., donepezil, rivastigmine, galantamine), N-methyl D-aspartate antagonist (e.g., memantine), or vitamin E.

Lithium co-crystals of the subject invention can be formulated according to known methods for preparing physiologically acceptable and/or pharmaceutically acceptable compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention may comprise between about 0.1% and 99%, and especially, 1 and 15% by weight of the total of one or more of the subject inflammatory mediator based on the weight of the total composition including carrier or diluent.

Lithium co-crystals, and compositions comprising them, can be delivered to a cell either through direct contact with the cell or via a carrier means. Carrier means for delivering lithium co-crystals and compositions to cells are known in the art and include, for example, encapsulating the composition in a liposome moiety. Another means for delivery of lithium co-crystals and compositions of the invention to a cell comprises attaching the lithium co-crystal to a protein, nucleic acid, or other moiety that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Lithium co-crystals can also be incorporated into polymers, examples of which include poly (D-L lactide-co-glycolide) polymer for intracranial delivery; poly[bis(p-carboxyphenoxy) propane:sebacic acid] in a 20:80 molar ratio (as used in GLIADEL); chondroitin; chitin; and chitosan.

While lithium co-crystals of the invention can be administered by themselves, they can also be administered as part of a pharmaceutical composition. The subject invention thus further provides compositions comprising one or more one or more lithium co-crystals in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

Other formulations of lithium co-crystals suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Lithium co-crystals of the invention, and compositions thereof, may be locally administered at one or more anatomical sites, optionally in combination with a pharmaceutically acceptable carrier such as an inert diluent. Lithium co-crystals of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the lithium co-crystals may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Lithium co-crystals, and compositions of the invention can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions can be prepared by incorporating a lithium co-crystal of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, lithium co-crystals of the invention may be applied in as a liquid or solid. However, it will generally be desirable to administer them topically to the skin as compositions, in combination with a dermatologically acceptable carrier, which may be a solid or a liquid. Lithium co-crystals can be applied in a formulation such as an ointment, cream, lotion, solution, tincture, or the like. Drug delivery systems for delivery of pharmacological substances to dermal sites can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver an inflammatory mediator to the skin are disclosed in U.S. Pat. No. 4,608,392; U.S. Pat. No. 4,992,478; U.S. Pat. No. 4,559,157; and U.S. Pat. No. 4,820,508.

Useful dosages of the lithium co-crystals, and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The subject invention also concerns kits comprising a lithium co-crystal of the invention, or a composition comprising a lithium co-crystal of the invention, in one or more containers, for treatment of a neuropsychiatric disorder. Kits of the invention can optionally include pharmaceutically acceptable carriers and/or diluents. A kit of the invention can comprise one or more additional agents for treatment of neuropsychiatric disorders. In one embodiment, a kit of the invention includes one or more other components, adjuncts, or adjuvants as described herein. In one embodiment, a kit of the invention includes instructions or packaging materials that describe how to administer a lithium co-crystal or composition of the kit. Containers of the kit can be of any suitable material, e.g., glass, plastic, metal, etc., and of any suitable size, shape, or configuration. In one embodiment, lithium co-crystal of the invention is provided in the kit as a solid, such as a tablet, pill, or powder form. In another embodiment, lithium co-crystal of the invention is provided in the kit as a liquid or solution. In one embodiment, the kit comprises an ampoule or syringe containing a lithium co-crystal of the invention in liquid or solution form.

The following terms are intended to have the meanings presented therewith below and are useful in understanding the description of the present invention and are not meant to limit the scope of the invention.

The term "amyloid beta peptide" means amyloid beta peptides processed from the amyloid beta precursor protein (APP). The most common peptides include amyloid beta peptides 1-40, 1-42, 11-40 and 11-42. Other species of less prevalent amyloid beta peptides are described as y-42, whereby y ranges from 2-17, and 1-x whereby x ranges from 24-39 and 41.

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as TWEEN, polyethylene glycol (PEG), and PLURONICS.

The term "contact" or "contacting" means bringing at least two moieties together, whether in an in vitro system or an in vivo system.

The term "condition" or "disease" means the overt presentation of symptoms (i.e., illness) or the manifestation of abnormal clinical indicators (e.g., biochemical indicators), or a genetic or environmental risk of or propensity for developing such symptoms or abnormal clinical indicators.

The term "inhibit" or "inhibiting" or "suppress" or "suppressing" or "suppressive," in relationship to the term "response" means that a response is decreased or prevented in the presence of a compound as opposed to in the absence of the compound.

The term "pharmaceutically acceptable prodrugs" as used herein means the prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as pro-drugs. A thorough discussion is provided in Bundgaard (1985), Widder et al. (1985), Krogsgaard-Larsen and Bandaged (1991), Bundgard (1992), Nielsenw and Bundgaard (1988), Nakeya et al. (1984), Higuchi and Stella (1987), which are incorporated herein by reference. An example of the prodrugs is an ester prodrug. "Ester prodrug" means a compound that is convertible in vivo by metabolic means (e.g., by hydrolysis) to an inhibitor compound according to the present invention. For example an ester prodrug of a compound containing a carboxy group may be convertible by hydrolysis in vivo to the corresponding carboxy group.

The term "pharmaceutically acceptable salts" refers to the non-toxic, inorganic and organic acid addition salts, and base addition salts, of compounds of the present invention. These salts can be prepared in situ during the final isolation and purification of compounds useful in the present invention.

The term "pharmaceutical excipients" refers to non-toxic adjuvants or compounds which can be added to the present invention which is capable of enhancing the biologically active effects of the peptide or its absorbancy in the body.

The term "solvate" means a physical association of a compound useful in this invention with one or more solvent molecules. This physical association can include hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "effective amount" or "therapeutically effective amount" means that amount of a compound or agent that will elicit the biological or medical response of a subject that is being sought by a medical doctor or other clinician. In particular, with regard to treating a neuropsychiatric disorder, the term "effective amount" is intended to mean that effective doses of medicament which can decrease one or more symptoms of the disorder in a subject such as cognitive impairment. The typical weight for an average mouse is approximately 0.025 kg with a metabolic rate of approximately 7.2 times that of a human. The typical weight for an average person is approximately 70 kg. With the standard weight and metabolic rate adjustments, it is within the scope of one of ordinary skill in the art to be able to derive effective doses for therapies of medicament of the invention as described herein. For example, effective amounts within the scope of the invention are equivalent mouse doses which is within about 5 mcg/day for a period as needed to achieve cognitive effects which is within about 2 mg/day for humans. Alternatively, effective doses for humans can also be within the range of about 50 mcg/day to about 2 mg/day, or alternatively 50 mcg/day, or 100 mcg/day, or 250 mcg/day, or 500 mcg/day, or 750 mcg/day or 1 mg/day or 1.25 mg/day, or 1.5 mg/day or 2 mg/day, or 2.25 mg/day, or 2.5 mg/day or adjusted as needed for the weight, metabolism and metabolic needs of the individual to at least achieve the effective cognitive effects of such individual.

The term "treating" means an intervention performed with the intention of reversing or preventing the development or altering the pathology of, and thereby alleviating a disorder, disease or condition, including one or more symptoms of such disorder, disease, or condition. Preventing refers to prophylactic or preventative measures, and includes delaying the onset of the disorder, disease or condition. The related term "treatment," as used herein, refers to the act of treating a disorder, symptom, disease or condition, as the term "treating" is defined above.

REFERENCES

Basselin, M., H. W. Kim, M. Chen, K. Ma, S. I. Rapoport, R. C. Murphy and S. E. Farias (2010). "Lithium modifies brain arachidonic and docosahexaenoic metabolism in rat lipopolysaccharide model of neuroinflammation." *Journal of lipid research* 51(5): 1049-1056.

Basselin, M., N. E. Villacreses, H. J. Lee, J. M. Bell and S. I. Rapoport (2007). "Chronic lithium administration attenuates up-regulated brain arachidonic acid metabolism in a rat model of neuroinflammation." *Journal of neurochemistry* 102(3): 761-772.

Dolomanov, O. V.; Bourhis, L. J.; Gildea, R. J.; Howard, J. A. K.; Puschmann, H. OLEX2: A complete structure solution, refinement and analysis program. *J. Appl. Crystallogr.* 2009, 42, 339-341.

Farrugia, L. J. WinGX suite for small-molecule single-crystal crystallography. *J. Appl. Cryst.* 1999, 32, 837-838.

Frick, L. R., K. Williams and C. Pittenger (2013). "Microglial dysregulation in psychiatric disease." *Clin Dev Immunol* 2013: 608-654.

Fukumoto, T., S. Morinobu, Y. Okamoto, A. Kagaya and S. Yamawaki (2001). "Chronic lithium treatment increases the expression of brain-derived neurotrophic factor in the rat brain." *Psychopharmacology (Berl)* 158(1): 100-106.

Goodwin, F. K., B. Fireman, G. E. Simon, E. M. Hunkeler, J. Lee and D. Revicki (2003). "Suicide risk in bipolar disorder during treatment with lithium and divalproex." *JAMA* 290(11): 1467-1473.

Klein, P. S. and D. A. Melton (1996). "A molecular mechanism for the effect of lithium on development." *Proceedings of the National Academy of Sciences of the United States of America* 93(16): 8455-8459.

Leyhe, T., G. W. Eschweiler, E. Stransky, T. Gasser, P. Annas, H. Basun and C. Laske (2009). "Increase of BDNF serum concentration in lithium treated patients with early Alzheimer's disease." *J Alzheimers Dis* 16(3): 649-656.

Phiel, C. J. and P. S. Klein (2001). "Molecular targets of lithium action." *Annual review of pharmacology and toxicology* 41: 789-813.

Rao, J. S., G. J. Harry, S. I. Rapoport and H. W. Kim (2010). "Increased excitotoxicity and neuroinflammatory markers in postmortem frontal cortex from bipolar disorder patients." *Molecular psychiatry* 15(4): 384-392.

Serhan, C. N., S. Hong, K. Gronert, S. P. Colgan, P. R. Devchand, G. Mirick and R. L. Moussignac (2002). "Resolvins: a family of bioactive products of omega-3 fatty acid transformation circuits initiated by aspirin treatment that counter proinflammation signals." The *Journal of Experimental Medicine* 196(8): 1025-1037.

Sheldrick, G. M. A short history of SHELX. *Acta Crystallogr.* 2008, A64, 112-122.

Sheldrick, G. M. Phase annealing in SHELX-90: Direct methods for larger structures. *Acta Crystallogr.* 1990, A46, 467-473.

Sheldrick, G. M. SADABS. Program for Empirical Absorption Correction; University of Göttingen: Göttingen, Germany, 1996.

Sheldrick, G. M. SHELXL-97. Program for the Refinement of Crystal; University of Göttingen: Göttingen, Germany, 1997.

Shorter, E. (2009). "The history of lithium therapy." *Bipolar disorders* 11 Suppl 2: 4-9.

Smith, A. J., S. H. Kim, N. K. Duggirala, J. Jin, L. Wojtas, J. Ehrhart, B. Giunta, J. Tan, M. J. Zaworotko and R. D. Shytle (2013). "Improving Lithium Therapeutics by Crystal Engineering of Novel Ionic Cocrystals." *Molecular Pharmaceutics*, 10(12):4728-38.

Stolk, P., P. C. Souverein, I. Wilting, H. G. Leufkens, D. F. Klein, S. I. Rapoport and E. R. Heerdink (2010). "Is aspirin useful in patients on lithium? A pharmacoepidemiological study related to bipolar disorder." *Prostaglandins, leukotrienes, and essential fatty acids* 82(1): 9-14.

Thies-Flechtner, K., B. Muller-Oerlinghausen, W. Seibert, A. Walther and W. Greil (1996). "Effect of prophylactic treatment on suicide risk in patients with major affective disorders. Data from a randomized prospective trial." *Pharmacopsychiatry* 29(3): 103-107.

Yu, F., Z. Wang, F. Tchantchou, C. T. Chiu, Y. Zhang and D. M. Chuang (2012). "Lithium ameliorates neurodegeneration, suppresses neuroinflammation, and improves behavioral performance in a mouse model of traumatic brain injury." *Journal of neurotrauma* 29(2): 362-374.

Yuskaitis, C. J. and R. S. Jope (2009). "Glycogen synthase kinase-3 regulates microglial migration, inflammation, and inflammation-induced neurotoxicity." *Cell Signal* 21(2): 264-273.

EXEMPLIFIED EMBODIMENTS

Exemplified embodiments of the invention include, but are not limited, to:

Embodiment 1

A method for treating a neuropsychiatric disorder, comprising administering an effective amount of a co-crystal of lithium to a subject in need thereof, wherein the co-crystal comprises lithium, or a pharmaceutically acceptable salt thereof, and an amino acid.

Embodiment 2

The method of embodiment 1, wherein the co-crystal comprises a pharmaceutically acceptable salt of lithium, and an amino acid.

Embodiment 3

The method of embodiment 1 or 2, wherein the pharmaceutically acceptable salt is lithium salicylate or lithium hydroxide.

Embodiment 4

The method of any preceding embodiment, wherein the amino acid is L-proline.

Embodiment 5

The method of any preceding embodiment, wherein the co-crystal comprises lithium salicylate and L-proline.

Embodiment 6

The method of any preceding embodiment, wherein the neuropsychiatric disorder is a neurodegenerative disorder.

Embodiment 7

The method of embodiment 6, wherein the neurodegenerative disorder is Alzheimer's disease, Parkinson's disease, or amyotrophic laterals sclerosis (ALS).

Embodiment 8

The method of any one of embodiments 1 to 5, wherein the neuropsychiatric disorder is a mood disorder, schizoaffective disorder, tic disorder, or suicidality.

Embodiment 9

The method of any preceding embodiment, further comprising administering an additional agent for treating the neuropsychiatric disorder before, during, or after the administration of the lithium co-crystal.

Embodiment 10

The method of embodiment 9, wherein the neuropsychiatric disorder is Alzheimer's disease or other dementia, and the additional agent is a cholinesterase inhibitor, N-methyl D-aspartate antagonist, vitamin E, or a combination of two or more of the foregoing.

Embodiment 11

The method of embodiment 10, wherein the additional agent is donepezil, rivastigmine, galantamine, memantine, or a combination of two or more of the foregoing.

Embodiment 12

The method of embodiment 9, wherein the additional agent is an anti-depressant, anti-convulsant, or mood stabilizer.

Embodiment 13

The method of embodiment 9, wherein the additional agent is a selective serotonin reuptake inhibitor (SSRI), serotonin-noroepinephrine reuptake inhibitor (SNRI), serotonin antagonist and reuptake inhibitor (SARI), monamine oxidase inhibitor (MAOI), carboxamide, fructose derivative, triazine, or a combination of two or more of the foregoing.

Embodiment 14

The method of any preceding embodiment, wherein the lithium co-crystal is administered to the subject in a composition comprising the lithium co-crystal and a pharmaceutically acceptable carrier.

Embodiment 15

The method of any preceding embodiment, wherein the subject has the neuropsychiatric disorder at the time of administration, and wherein said method further comprises identifying the subject as having the neuropsychiatric disorder prior to administration.

Embodiment 16

The method of any one of embodiments 1 to 14, wherein the subject does not have the neuropsychiatric disorder at the time of administration, and wherein the lithium co-crystal is administered as a prophylaxis to prevent or delay the onset of the neuropsychiatric disorder.

Embodiment 17

A pharmaceutical composition comprising a co-crystal of lithium comprising lithium, or a pharmaceutically acceptable salt thereof, and an amino acid; and an additional agent effective in treating a neuropsychiatric disorder.

Embodiment 18

The composition of embodiment 17, wherein the additional agent is a cholinesterase inhibitor, N-methyl D-aspartate antagonist, vitamin E, or a combination of two or more of the foregoing.

Embodiment 19

The composition of embodiment 17, wherein the additional agent is donepezil, rivastigmine, galantamine, memantine, or a combination of two or more of the foregoing.

Embodiment 20

The composition of embodiment 17, wherein the additional agent is an anti-depressant, anti-convulsant, or mood stabilizer.

Embodiment 21

The composition of embodiment 17, wherein the additional agent is a selective serotonin reuptake inhibitor (SSRI), serotonin-noroepinephrine reuptake inhibitor (SNRI), serotonin antagonist and reuptake inhibitor (SARI), monamine oxidase inhibitor (MAOI), carboxamide, fructose derivative, triazine, or a combination of two or more of the foregoing.

Embodiment 22

A method for delivery of lithium and/or achieving one or more of the following in a subject comprising administering an effective amount of a lithium co-crystal or pharmaceutical composition of any preceding embodiment through any route of delivery: increasing brain-derived neurotrophic factor (BDNF) activity, attenuating of interleukin-6 and/or nitric oxide in microglia, reducing Aβ generation, increasing inhibitory GSK3β (Ser9) phosphorylation (e.g., in neuronal cells), decreasing tau phosphorylation (e.g., in neuronal cells), increasing brain 17-hydroxy-docosahexaenoic acid (17-OH-DHA), inhibiting microglial activation-induced by IFNγ and CD40 signaling, enhancing microglial phagocytosis of Aβ, promoting or enhancing neuronal stem cell differentiation, or promoting autophagy.

Materials and Methods

Reagents and Materials.

Lithium salicylate (≥98% purity), lithium hydroxide (≥98% purity), nicotinic acid (≥98% purity), and proline (≥99% purity) were purchased from Sigma-Aldrich Corporation (St. Louis, Mo.) and used as such without further purification.

Lithium Cocrystal Syntheses.

LISPRO.

Lithium salicylate (≥98% pure, anhydrous, used as received from Sigma Aldrich, 1 mmol) and $_L$-proline (≥99% pure, used as received from Sigma Aldrich, 1 mmol) were dissolved in 2.0 mL of hot deionized water. The resulting solution was maintained on a hot plate (75-90° C.) to allow slow evaporation of solvent until crystals had formed. Colorless crystals of LISPRO were collected.

LNAPRO. Lithium hydroxide (≥98% pure, anhydrous, used as received from Sigma Aldrich, 1 mmol), nicotinic acid (≥98% pure, anhydrous, used as received from Sigma Aldrich, 1 mmol), and $_L$-proline (≥99% pure, used as received from Sigma Aldrich, 2 mmol) were dissolved in 3.0 mL of deionized water and left to stand on a hot plate until block shape colorless crystals had emerged from solution.

Single-Crystal X-Ray Data Collection and Structure Determinations.

The X-ray diffraction data were collected using a Bruker-AXS SMART-APEXII CCD diffractometer (Cu Kα, λ=1.54178 Å). Indexing was performed using APEX2 (Bruker APEX2, version 2008.1-0; Bruker AXS Inc.: Madison, Wis., 2008) (Difference Vectors method). Data integration and reduction were performed using SaintPlus 6.01 (SAINT, V6.28A; Data Reduction Software; Bruker AXS Inc.: Madison, Wis., 2001). Absorption correction was performed by multiscan method implemented in SA-DABS (Sheldrick, 1996). Space groups were determined using XPREP implemented in APEX2 (Bruker APEX2, version 2008.1-0; Bruker AXS Inc.: Madison, Wis., 2008). The structure was solved using SHELXS-97 (direct methods) and refined using SHELXL-97 (full-matrix least-squares on $F^2$) contained in OLEX2 (Dolomanov et al., 2009) and WinGX v1.70.01 (Farrugia, 1999; Sheldrick, 1997; Sheldrick, 2008; Sheldrick, 1990) programs.

LISPRO.

All non-hydrogen atoms, except disordered C29a and C29b, were refined anisotropically. Hydrogen atoms of —CH, —CH2, —NH2, and —OH groups were placed in geometrically calculated positions and included in the refinement process using riding model with isotropic thermal parameters: Uiso(H)=1.2Ueq (—CH, —CH2, —NH2), Uiso(H)=1.5Ueq(—OH). One of the $_L$-proline rings is disordered over two positions in a 1:1 ratio. SADI commands were used to restrain distances between disordered carbon atoms. The crystal was a twin, and refinement was conducted with an HKL5 type file generated using the [−1/0/0;0/−1/0;0.14/0/1] twin law. This corresponds to 180° rotation about the [001] reciprocal lattice direction. Crystallographic data is available in the Cambridge Structural Database (CCDC 962323). The structure with probability ellipsoids is available in FIG. 10.

LNAPRO.

All non-hydrogen atoms were refined anisotropically. Hydrogen atoms of the —CH and —CH$_2$ groups were placed in geometrically calculated positions and included in the refinement process using riding model with isotropic thermal parameters: Uiso(H)=1.2Ueq (—CH, —CH$_2$, —NH$_2$). Hydrogen atoms of the —NH$_2$ group were found from difference Fourier map inspection and were freely refined. Crystal data and refinement conditions are shown in Table 1. The $_L$-proline ring was found to be disordered over two positions with an approximate ratio of 0.7:0.3. Crystallographic data is available in the Cambridge Structural Database (CCDC 962324). The structure with probability ellipsoids is available in FIG. 11.

TABLE 1

Crystallographic Data and Structure Refinement Parameters

| | LISPRO | LNAPRO |
|---|---|---|
| Formula | $C_{12}H_{14}LiNO_5$ | $C_{11}H_{13}LiN_2O_4$ |
| MW | 259.18 | 244.17 |
| crystal system | monoclinic | orthorhombic |
| space group | $P2_1$ | $P2_12_12$ |
| a (Å) | 10.3601(19) | 10.2156(2) |
| b (Å) | 10.1556(16) | 10.4646(3) |
| c (Å) | 12.173(3) | 11.3811(3) |
| α (deg) | 90.00 | 90.00 |
| β (deg) | 93.415(11) | 90.00 |
| γ (deg) | 90.00 | 90.00 |
| V (Å$^3$) | 1278.5(4) | 1216.66(5) |
| $D_c$ (mg m$^{-3}$) | 1.347 | 1.333 |
| Z | 4 | 4 |
| 2θ range | 7.28-131.94° | 7.76-131.9° |
| $N_{ref}/N_{para}$ | 6896/352 | 2116/183 |
| T (K) | 228(2) | 228(2) |
| $R_1$ [I > 2σ(I)] | 0.0394 | 0.0394 |
| $wR_2$ | 0.0935 | 0.0935 |
| GOF | 0.988 | 0.988 |
| abs coef. | 0.872 | 0.843 |

Crystal Structure Description.

Lithium Salicylate Proline, LISPRO.

Figure 9A:
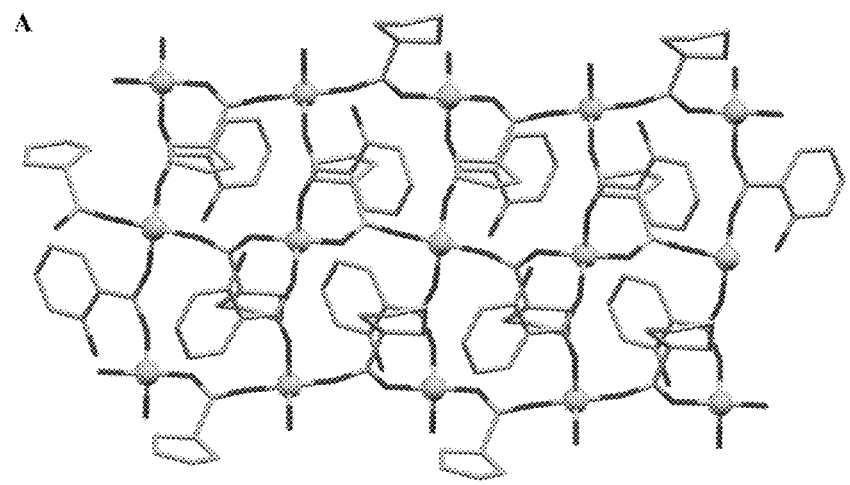
FIGS. 9A and 9B. Crystal packing in LISPRO and LNAPRO. Square grid network exhibited by LISPRO (FIG. 9A) and LNAPRO (FIG. 9B). Hydrogen atoms are removed for clarity.

Single crystal X-ray structural analysis reveals that LISPRO contains four lithium cations, four salicylate anions, and four $_L$-proline molecules in the unit cell. There are two formula units in the asymmetric unit. Each lithium cation is linked to adjacent lithium cations by four bridging carboxylate moieties, two from salicylate and two from $_L$-proline (Li—O distances: 1.916(1), 1.915(1) and 1.875(1), 1.905(1) Å). The overall network can be described as square grids and is illustrated in FIG. 9A. The hydroxyl group of salicylate and protonated nitrogen of $_L$-proline are involved in intramolecular and intermolecular hydrogen bonds (O—H . . . O$^-$: 2.558(1) and 2.641(1); N$^+$—H . . . O$^-$: 2.751(1), 2.745(1) and 2.874(1) Å) (Table 2). The single crystal X-ray diffraction parameters of this and the other crystal structures reported herein are tabulated in Table 1.

TABLE 2

LISPRO Hydrogen Bonds

| D | H | A | d(D-H)/Å | d(H-A)/Å | d(D-A)/Å | D-H-A/deg |
|---|---|---|---|---|---|---|
| N9 | H9B | O3 | 0.91 | 1.84 | 2.750(6) | 178.4 |
| N11 | H11A | O10$^a$ | 0.91 | 1.83 | 2.744(6) | 176.6 |
| N11 | H11B | O7 | 0.91 | 2.01 | 2.873(8) | 158.7 |

TABLE 2-continued

LISPRO Hydrogen Bonds

| D | H | A | d(D-H)/Å | d(H-A)/Å | d(D-A)/Å | D-H-A/deg |
|---|---|---|---|---|---|---|
| O26 | H26 | O4 | 0.83 | 1.92 | 2.640(9) | 144.1 |
| O28 | H28 | O5 | 0.83 | 1.82 | 2.557(7) | 146.9 |

$^a$1 + X, +Y, +Z.

TABLE 3

LNAPRO Hydrogen Bonds

| D | H | A | d(D-H)/Å | d(H-A)/Å | d(D-A)/Å | D-H-A/deg |
|---|---|---|---|---|---|---|
| N5 | H5A | O2 | 0.97(2) | 1.83(2) | 2.779(2) | 163(2) |
| N5 | H5B | O1$^a$ | 0.95(3) | 1.81(3) | 2.762(2) | 176(2) |

$^a$−½ − X, ½ + Y, −1 − Z.

Lithium Nicotinate Proline, LNAPRO.

Figure 9B:
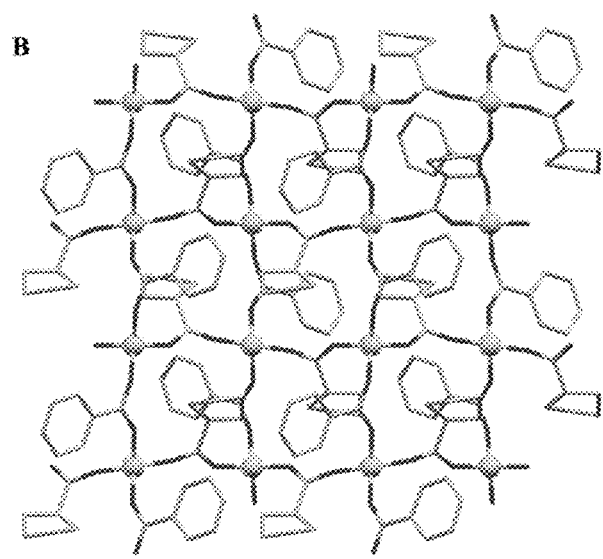
Figure 10:
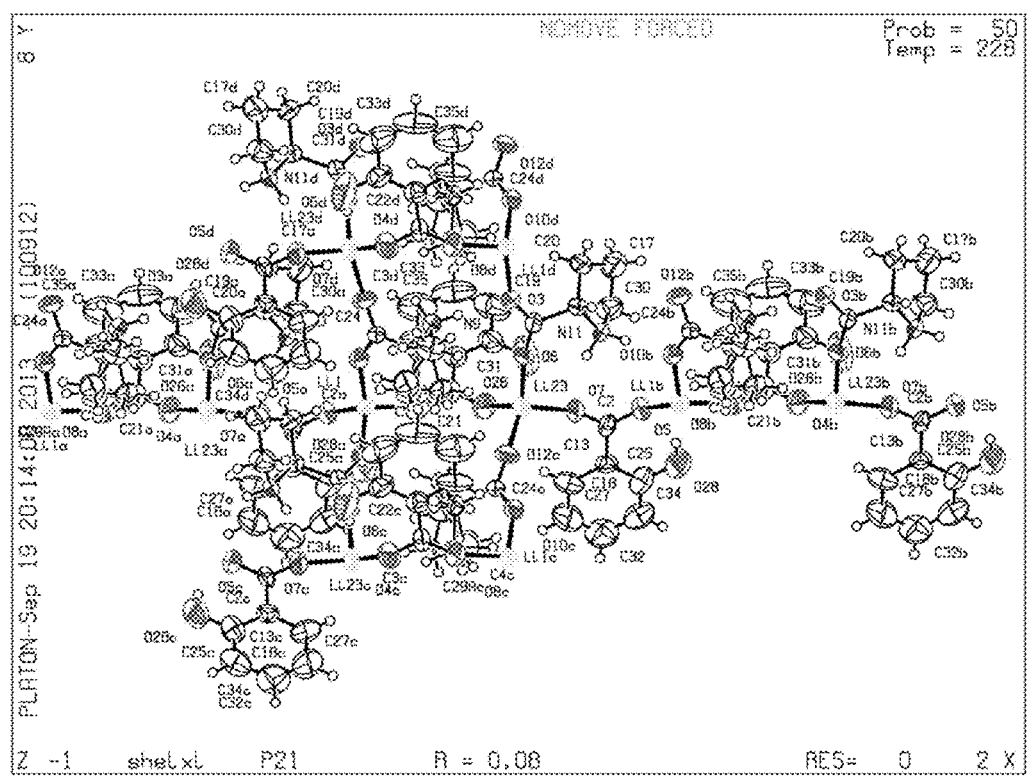
FIG. 10: LISPRO structure with probability ellipsoids.
Figure 11:
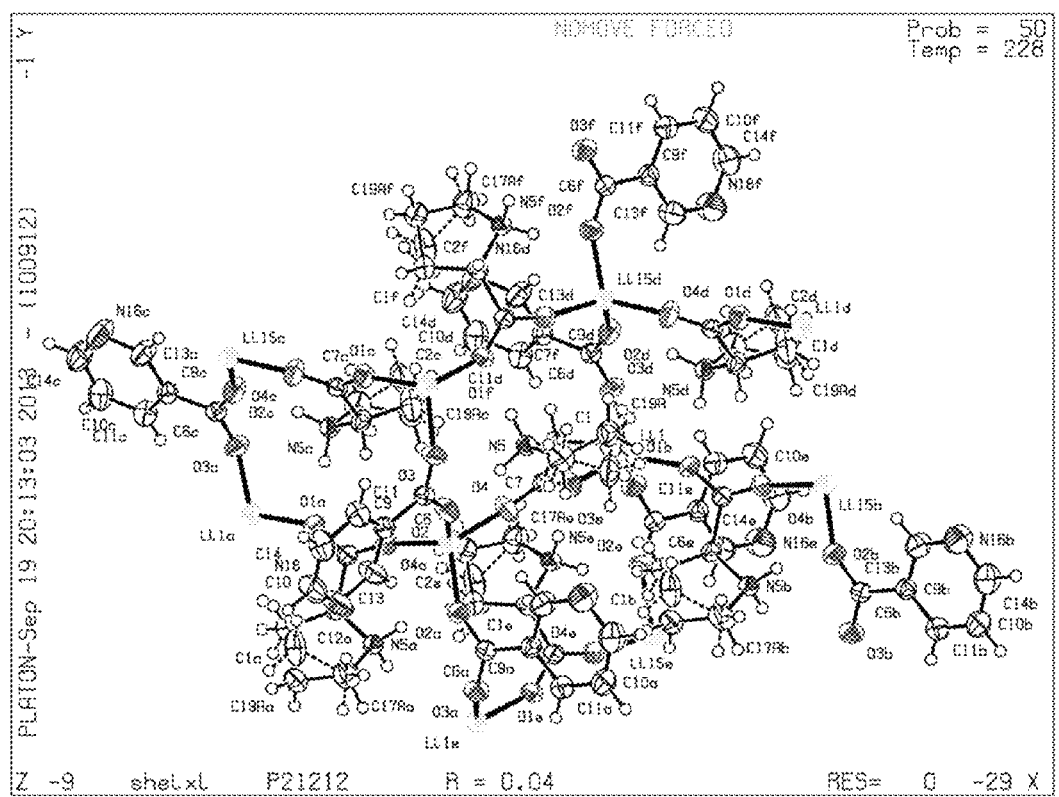
FIG. 11: LNAPRO structure with probability ellipsoids.
Figure 12:
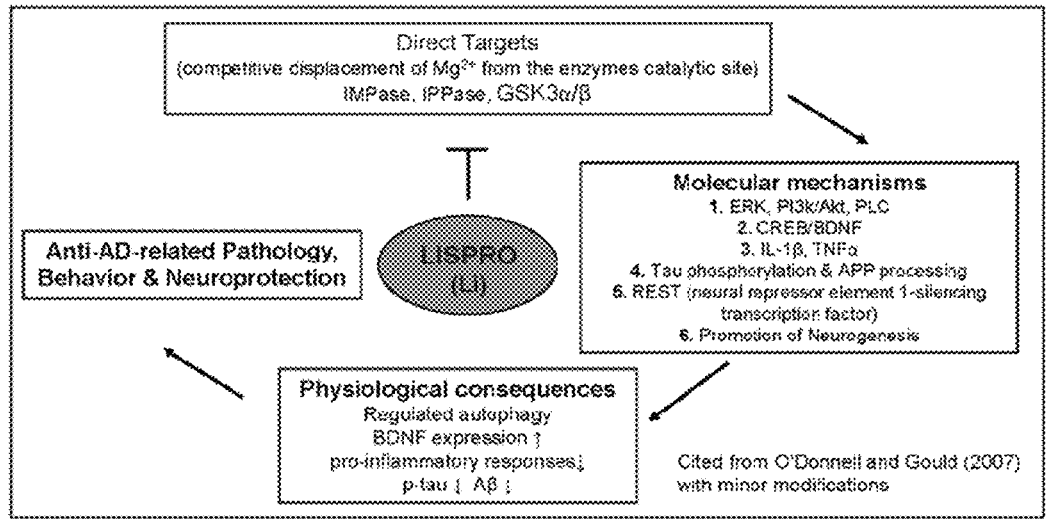
FIG. 12: Diagram showing mechanisms that may underlie lithium's (and LISPRO's) potential efficacy for Alzheimer's disease.

The crystal structure of LNAPRO reveals that the 1:1 ICC crystallized in space group $P2_12_12$ and that it contains four lithium cations, four nicotinate anions, and four $_L$-proline molecules in the unit cell. There is one formula unit in the asymmetric unit. Two carboxylate moieties of nicotinate and two carboxylate moieties of proline molecules bridge adjacent lithium cations (Li—O distances: 1.897(3), 1.897(3) and 1.920(3), 2.920(3) Å). Undulating square grid networks are thereby generated as shown in FIG. 9B. The protonated nitrogen atoms of proline form hydrogen bonds with carboxylate moieties (N$^+$—H . . . O$^-$: 2.779(2) and 2.762(2) Å) (Table 3).

All patents, patent applications, provisional applications, and publications referred to or cited herein are incorporated by reference in their entirety, including all figures and tables, to the extent they are not inconsistent with the explicit teachings of this specification.

All percentages are by weight and all solvent mixture proportions are by volume unless otherwise noted.

Example 1

Preparation and Characterization of Lithium Salicylate Proline (LISPRO, M.W. 258.18)

Lithium salicylate (≥98% pure, anhydrous, used as received from Sigma Aldrich, 1 mmol) and L-proline (≥99% pure, used as received from Sigma Aldrich, 1 mmol) were dissolved in 2.0 mL of hot deionized water. The resulting solution was maintained on a hot plate (75-90° C.) to allow slow evaporation of solvent until crystals had formed. Colorless crystals of LISPRO were collected. In addition, lithium hydroxide (≥98% pure, anhydrous, used as received from Sigma Aldrich, 1 mmol), nicotinic acid (≥98% pure, anhydrous, used as received from Sigma Aldrich, 1 mmol), and L-proline (≥99% pure, used as received from Sigma Aldrich, 2 mmol) were dissolved in 3.0 mL of deionized water and left to stand on a hot plate until block shape colorless crystals had emerged from solution. The purity of both co-crystal preparations were confirmed by powder X-ray diffraction, differential scanning (DSC) calorimetry and atomic absorption spectrometry (AAS) (20). Co-crystals of lithium may be produced using the methods described in Smith A J et al. (*Mol. Pharmaceutics* 2013, 10, 4728-4738), which is incorporated herein by reference in its entirety. Characterization of the structure and properties of embodiments of lithium co-crystals that may be used in the invention are described in Smith A J et al. and in FIGS. 9A-B, 10, and 11 herein.

Example 2

LISPRO Reduces Aβ Generation without Inhibiting Notch Processing

Figure 1B:
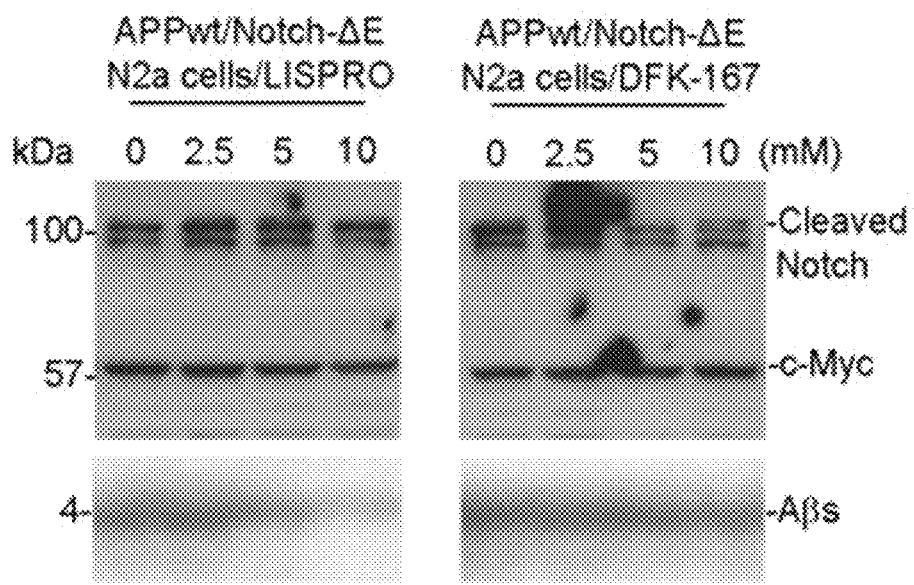

N2a cells expressing human wild-type APP (N2a/APPwt cells) were treated with LISPRO followed by analysis of Aβ$_{40,42}$ peptides secreted in the cell culture media by Aβ ELISA. The Aβ ELISA results are represented as the mean±SD of Aβ$_{40}$ or Aβ$_{42}$ (ng/mL) for 3 independent experiments for each condition (*P<0.05) (FIG. 1A). To examine whether LISPRO can affect Notch processing, N2a/APPwt cells were co-transfected with Notch-ΔE vector. N2a/APPwt/Notch-ΔE cells were treated with LISPRO or DFK-167 (positive control for Notch cleavage) at 0, 2.5, 5 and 10 mM for 5 hours followed by analysis of the cell lysates by Western blot (WB) (FIG. 1B). WB with both c-myc antibody (9E10, Abcam®) and cleaved Notch antibody (Val1744, Cell Signaling Technology®) showed that LISPRO treatment did not inhibit Notch cleavage compared to DFK-167.

Example 3

Treatment with LISPRO Decreases Tau Phosphorylation in HeLa/Tau Cells while Increasing Inhibitory GSK3β (Ser$^9$) Phosphorylation Human tau stably transfected HeLa cells (HeLa/tau cells) were treated with LISPRO at the indicated concentrations for 12 hours, followed by analysis of cell lysates by WB. Phosphorylation status of GSK3β [pGSK3β (Ser$^9$)] was detected by anti-phospho-GSK3β (Ser$^9$) and total GSK3β antibodies (FIG. 3A). Phosphorylation status of tau was detected by anti-phospho-tau [p-tau (Thr$^{231}$)] and PHF1 antibodies. Total tau (phosphorylated and non-phosphorylated) was detected by tau-46. WB results are representative of two independent experiments for pGSK3β (Ser$^9$) and total GSK3β, and three experiments respectively for PHF1, p-tau (Thr$^{231}$) and total tau (FIG. 3B). Densitometry analysis below each WB figure panel in FIGS. 3A and 3B shows the band density ratio of pGSK3β (Ser$^9$) to total GSK3β as well as p-tau (Thr$^{231}$) to total tau. A t-test revealed a significant increase in the ratio of pGSK3β (Ser$^9$) to total GSK3β and decrease in p-tau to total tau for HeLa/tau cells treated with 10 mM LISPRO compared to control (0 mM) (*P<0.05; **P<0.01). Aβ$_{40,42}$ peptides were undetectable by Aβ ELISA of the conditioned media from HeLa/tau cells with or without LISPRO (data not shown).

Example 4

Treatment with LISPRO Dose-Dependently Increases Inhibitory GSK3β (Ser$^9$) Phosphorylation in SH-SY5Y Cells and Primary Neuronal Cells Human neuroblastoma (SH-SY5Y) cells (FIG. 2A) and primary neuronal cells (FIG. 2B) were treated with LISPRO for 12 hours followed by analysis of cell lysates by WB. Below each figure panel, densitometry analysis shows the band density ratio of pGSK3β (Ser$^9$) to total GSK3β. WB results are representative of three independent experiments.

A t-test revealed significant difference in the ratio of pGSK3β (Ser$^9$) to total GSK3β for both SH-SY5Y cells and differentiated neuronal cells treated with either 5 or 10 mM LISPRO compared to control (0 mM) (*P<0.05).

Example 5

Oral LISPRO Reduces β-Amyloid Pathology in Tg2576 Mice

Figure 14A:
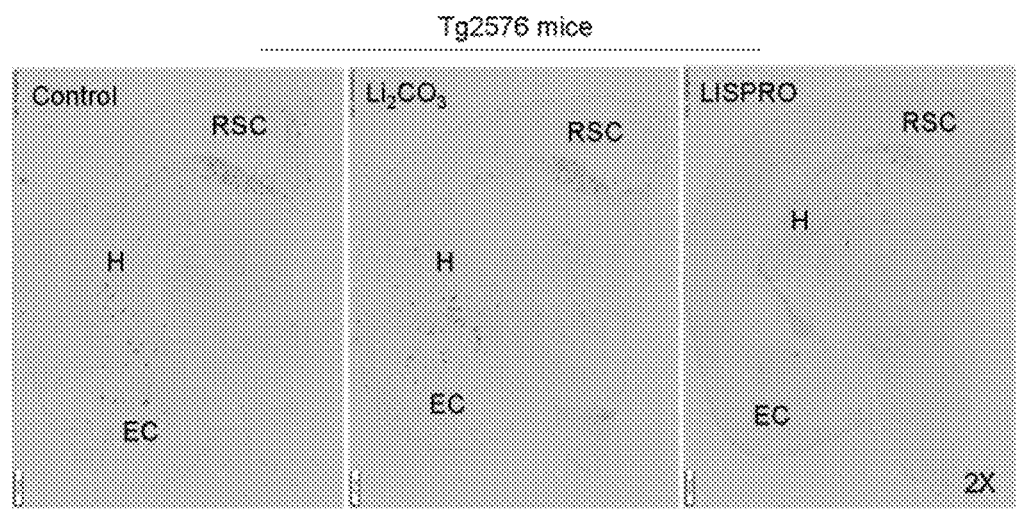
FIGS. 14A-C show that orally administered LISPRO reduces β-amyloid pathology in Tg2576 mice (described in Example 5).
Figure 14B:
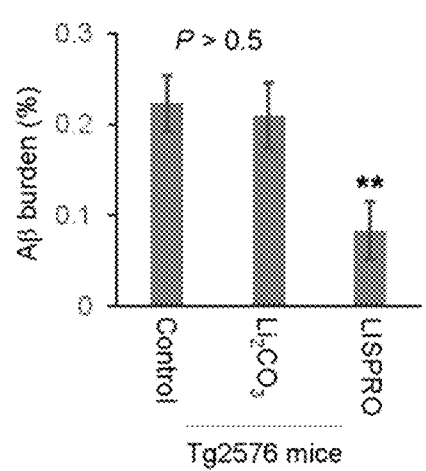
Figure 14C:
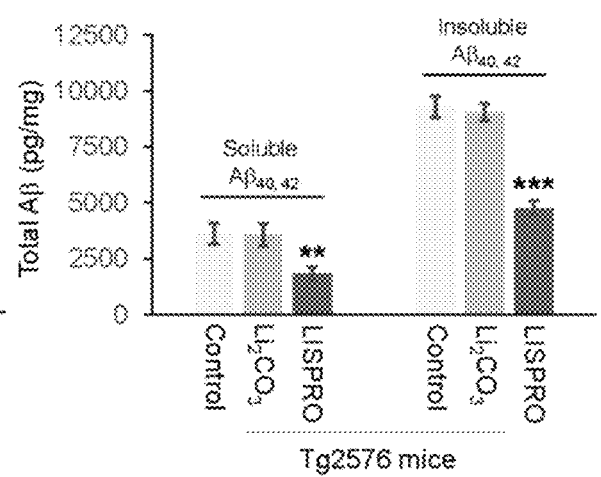

Tg2576 mice at 8 months of age (the Tg mouse line 2576) were divided into two groups (n=9; 5 male/4 female) and were fed for 8 weeks with 2 diets providing lithium at 2.25 mmol/kg/day as indicated. These diets consisted of a standard NIH31 chow supplemented with Li$_2$CO$_3$ (0.5 g/kg) or LISPRO (3.5 g/kg). The dosages were chosen to give brain lithium concentrations of 0.25-0.50 mmol/L, which fall in a range of clinical therapy for AD (2, 14, 27). All mice received normal drinking water ad libitum. In parallel, six additional Tg2576 mice (3 male/3 female) were fed a standard NIH31 chow for 8 weeks as a control group. Mouse brain tissue sections and homogenates were prepared from each mouse after treatment. Half-brain coronal sections were analyzed by Aβ antibody 4G8 staining (FIG. 14A). Percentage of 4G8 positive plaques (mean±SD) was quantified by image analysis (28, 29) (FIG. 14B). Total soluble and insoluble Aβ$_{40,42}$ peptides from homogenates were analyzed by ELISA, and represented as picograms of Aβ peptides per mg of total protein (FIG. 14C). LISPRO but not Li$_2$CO$_3$ treatment markedly reduced total soluble and insoluble Aβ$_{40,42}$ levels. A t-test for independent samples revealed significant differences (P<0.01, *P<0.005) between groups. There was no notable or significant difference in both 4G8 positive Aβ plaques and cerebral soluble/insoluble Aβ$_{40,42}$ levels in brain sections and homogenates between Li$_2$CO$_3$— and control NIH31 diet-fed Tg2576 mice (P>0.05).

Example 6

Figure 15A:
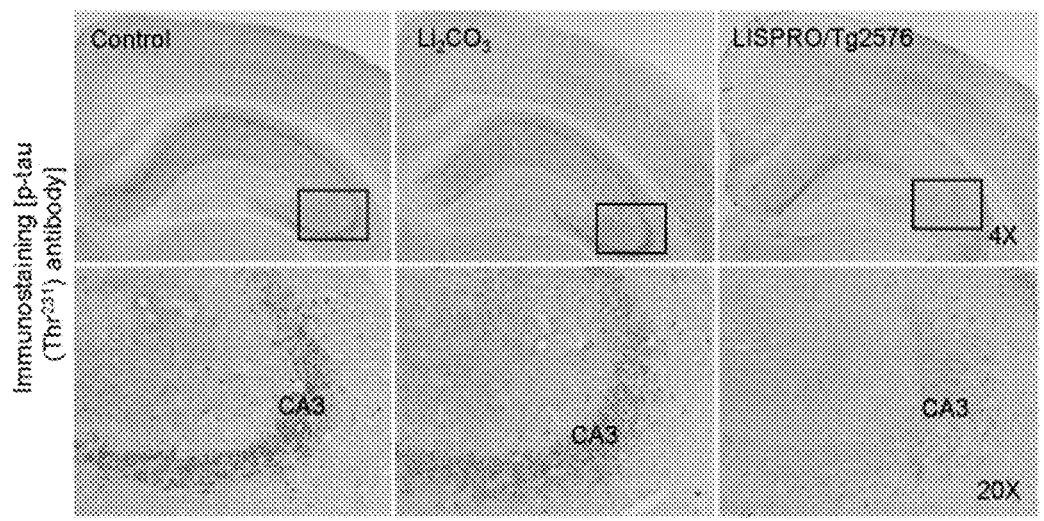
FIGS. 15A-C show that orally administered LISPRO attenuates tau hyper-phosphorylation and GSK3β activation in Tg2576 mice (described in Example 6).
Figure 15B:
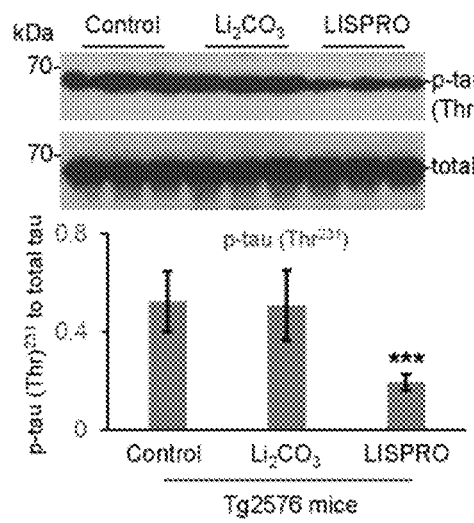
Figure 15C:
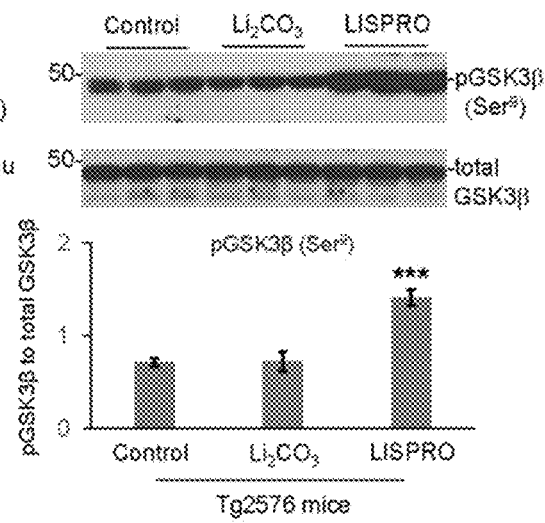

Oral LISPRO Treatment Attenuates Tau Hyper-Phosphorylation and GSK3β Activation in Tg2576 Mice Mouse brain sections from LISPRO, Li$_2$CO$_3$ and control NIH31 chow fed Tg2576 mice as described in FIGS. 14A-C above were immunohistochemistry stained with anti-phospho-tau (Thr$^{231}$) [p-tau (Thr$^{231}$)] antibody (FIG. 15A). Mouse brain homogenates were subjected to WB analysis with antibodies against p-tau (Thr$^{231}$) or total tau (FIG. 15B) or with antibodies against phospho- or total-GSK3β (FIG. 15C). Inhibitory phosphorylation status of GSK3β was detected by anti-phospho-GSK3β (Ser$^9$) [pGSK3β (Ser$^9$)] antibody. As shown below WB, densitometry analysis shows the band density ratios of p-tau (Thr$^{231}$) to total tau and pGSK3β (Ser$^9$) to total GSK3β. A t-test revealed significant decreases in the ratios of p-tau (Thr$^{231}$) to total tau and increases in pGSK3β (Ser$^9$) to total GSK3β in LISPRO-treated compared to Li$_2$CO$_2$-treated Tg2576 mice (***P<0.005). Similar results from both immunochemistry staining and WB analyses were also obtained with PHF-1 antibody (data not shown). There was no notable and significant difference in both phospho-tau and inactivated GSK3β levels in brain homogenates between Li$_2$CO$_3$— and control NIH31 diet-fed Tg2576 mice (P>0.5).

Example 7

Oral Administration of LISPRO Promotes Anti-Inflammatory/Th2 Responses and Decreases sCD40L in the CNS of Tg2576

Figure 16A:
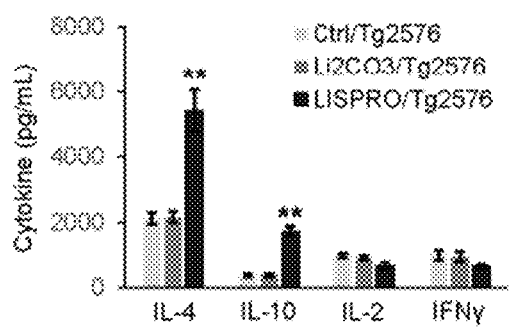
FIGS. 16A-D show that orally administered LISPRO promotes anti-inflammatory/Th2 responses and decreases sCD40L in the CNS of Tg2576 mice (described in Example 7).
Figure 16C:
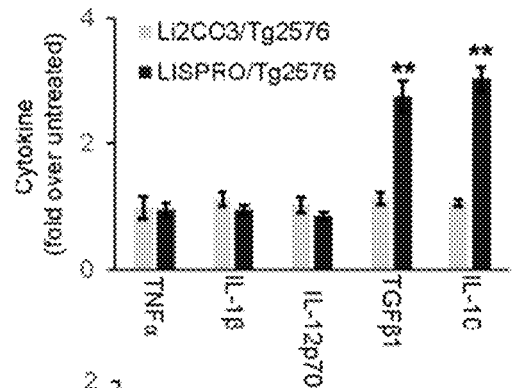
Figure 16B:
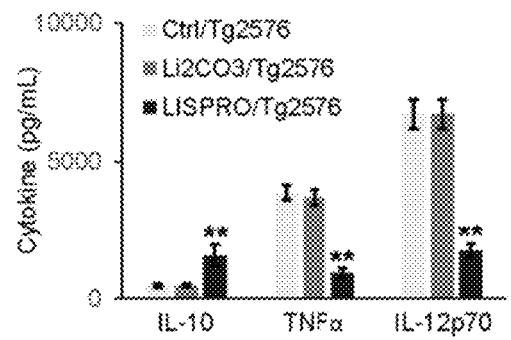
Figure 16D:
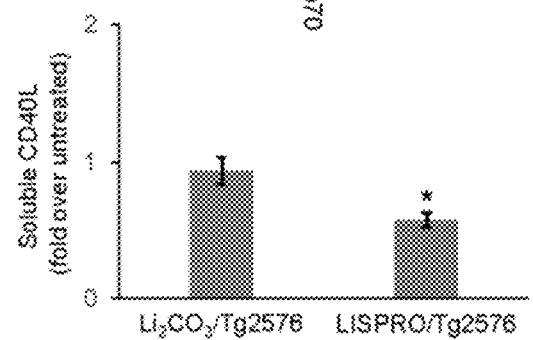

Plasma samples and brain homogenates were prepared from the LISPRO- and Li$_2$CO$_3$-treated and untreated Tg2576 (Ctrl chow) mice as described in FIGS. 14A-C above and subjected to biochemical analysis. In addition, spleens from these mice were isolated and splenocytes cultured as described previously (30). ELISA results are shown for: plasma (FIG. 16A), splenocyte cultured media (FIG. 16B), and brain tissue-derived cytokines (FIG. 16C) and sCD40L (FIG. 16D). Data are presented as mean±SD (n=9 mice in the LISPRO- and Li$_2$CO$_3$-treated groups; n=6 mice for the untreated group) values of cytokines (pg/mL plasma or medium) (FIGS. 16A and 16B) or fold increase of brain tissue-derived cytokines or sCD40L over untreated Tg2576 mice (FIGS. 16C and 16D) (*P<0.05; **P<0.01). There was no notable or significant difference in cytokine levels in plasma and splenocyte cultured media between Li$_2$CO$_3$— and control NIH31 diet-fed Tg2576 mice (P>0.05).

Example 8

LISPRO Markedly Promotes Neuronal Cell Differentiation

Murine neuroblastoma (N2a cells) were treated with LISPRO or appropriate controls (including Li$_2$CO$_3$, LiCl, and L-proline, Sigma, all at 10 mM, optimized by our pilot studies) for 24 hours. These cells were then permeabilized with 0.05% Triton X-100 for 5 min, washed, and stained with mouse anti-β-tubulin III monoclonal antibody (STEMCELL™) and rabbit anti-phospho-synapsin I (Ser$^{62}$, Ser$^{67}$) polyclonal antibody (EMD Millipore) overnight at 4° C. Alexa Fluor® 488 Goat anti-mouse IgG (green) and Alexa Fluor® 594 Donkey anti-rabbit IgG (red), Life Technologies, were used to detect β-tubulin III and phospho-synapsin I signals respectively. Confocal images were taken by Olympus Fluoview™ FV1000 laser scanning confocal microscope (Tokyo, Japan) (FIG. 5A). In parallel, additional N2a cells were treated with LISPRO, Li$_2$CO$_3$, LiCl, or L-proline at 10 mM, lysed with cell lysis buffer, and then subjected to WB analysis of β-tubulin III, phospho-synapsin I or β-actin (FIG. 5B). The band density ratios of (3-tubulin and phospho-synapsin I (p-synapsin I) to β-actin are presented as mean±S.D (FIG. 5C). These data are representative of three independent experiments with similar results (*P<0.05; **P<0.005). There was no notable or significant difference in β-tubulin III and phospho-synapsin I immunofluorescence and WB analysis between Li$_2$CO$_3$ and LiCl, or L-proline (P>0.05).

Example 9

LISPRO Enhances Murine Neuronal Stem Cell Differentiation

Murine neuronal stem cells (ATCC) were treated with LISPRO, Li$_2$CO$_3$, LiCl, or L-proline at 10 mM for 4 days, permeabilized and stained with mouse anti-MAP2 monoclonal antibody (EMD Millipore), mouse anti-total tau (tau46), or rabbit anti-phospho-synapsin I (Ser$^{62}$, Ser$^{67}$) polyclonal antibody overnight at 4° C. Alexa Fluor® 488

Goat anti-mouse IgG (green) and Alexa Fluor® 594 Donkey anti-rabbit IgG (red) were used to detect MAP2, phospho-synapsin I and total tau. DAPI staining (Life Technologies) was used to detect nuclear DNA. Confocal images were taken by Olympus Fluoview™ FV1000 laser scanning confocal microscope (FIG. 17A). In parallel, additional neuronal stem cells were treated with LISPRO, $Li_2CO_3$, LiCl or L-proline, lysed with cell lysis buffer and analyzed by WB. The band density ratios of MAP2 to β-actin, total tau to β-actin, and phospho-synapsin I to β-actin are presented as mean±S.D (FIGS. 17B-1, 17B-2, and 17B-3, respectively). These data are representative of two independent experiments with similar results (**$P<0.005$). Note that there was no significance difference in MAP2, phospho-synapsin I, and total tau immunofluorescence and WB analysis between $Li_2CO_3$ and LiCl or L-proline ($P>0.05$).

Example 10

LISPRO Enhances Human Neuronal Stem Cell Differentiation

Figure 18A:
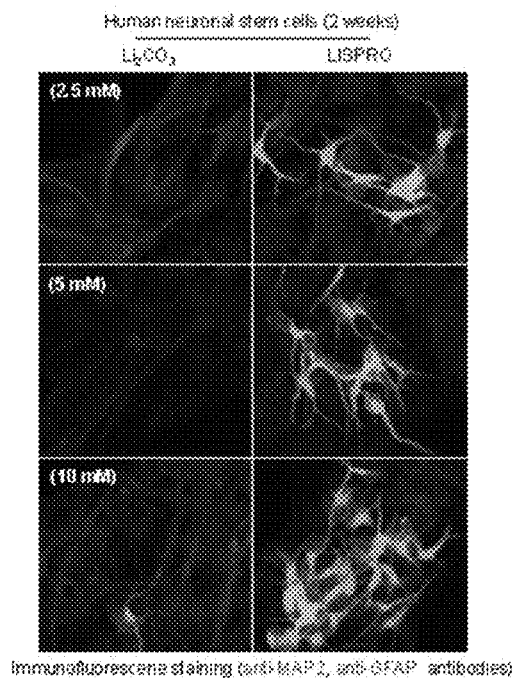
FIGS. 18A-C show that LISPRO enhances human neuronal stem cell differentiation (described in Example 10).
Figure 18B:
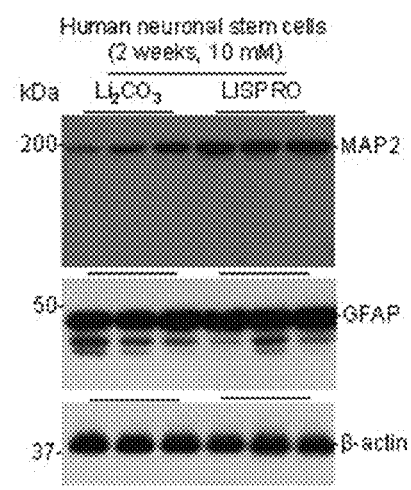
Figure 18C:
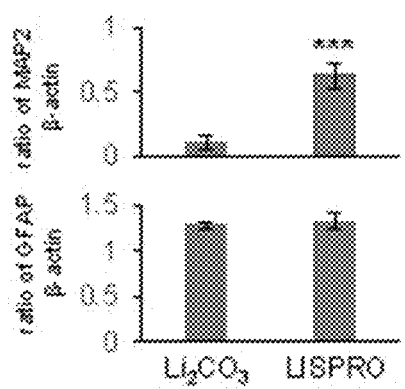

Human neural stem cells (H9-Derived) were obtained from Life technologies and cultured with StemPro® NSC SFM media. They were treated with LISPRO, $Li_2CO_3$, LiCl or L-proline at 10 mM for 14 days, permeabilized and stained with mouse anti-MAP2 monoclonal antibody or rabbit anti-GFAP polyclonal antibody overnight at 4° C. Alexa Fluor® 488 Goat anti-mouse IgG (green) and Alexa Fluor® 594 Donkey anti-rabbit IgG (red) were used to detect MAP2 and GFAP respectively. DAPI was used to detect nuclear DNA. Confocal images were taken by Olympus Fluoview™ FV1000 laser scanning confocal microscope (FIG. 18A). In parallel, additional human neuronal stem cells were treated with LISPRO, $Li_2CO_3$, LiCl, or L-proline, lysed with cell lysis buffer and analyzed by WB (FIG. 18B). The band density ratios of MAP2 to β-actin (***$P<0.001$) and GFAP to β-actin ($P>0.05$) are presented as mean±S.D (FIG. 18C). These data are representative of two independent experiments with similar results. Note that there was no significance difference in MAP2 and GFAP immunofluorescence and WB analyses between $Li_2CO_3$ and LiCl or L-proline ($P>0.05$).

Example 11

LISPRO Inhibits Microglial Activation-Induced by IFNγ and CD40 Signaling and Enhances Microglial Phagocytosis of Aβ

Figure 4A:
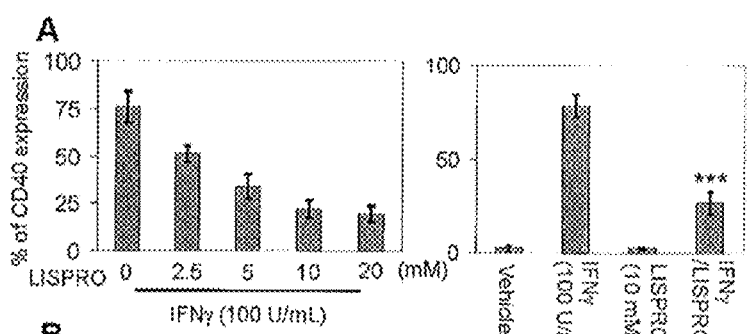
FIGS. 4A-4C. LISPRO inhibits microglial activation-induced by IFNγ and CD40 signaling and enhances microglial phagocytosis of Aβ. Primary microglial cells were treated with LISPRO in the presence of IFNγ or/and CD40 ligand (CD40L, 1 µg/mL) for 8 h and then examined pro-inflammatory microglial activation as assessed by flow cytometric (FACS) analysis and ELISA (FIG. 4A). FACS analysis showed significant dose dependent decreases in IFNγ-induced CD40 expression following 8 h of co-treatment with LISPRO. Data are represented as mean percentage of CD40 expressing cells (±SD). Results are representative of two independent experiments (FIG. 4B). Microglial cell culture supernatants were collected and subjected to cytokine ELISA as indicated. Data were represented as mean pg of TNFα or IL-12p70 per mg of total cellular protein (±SD). Results are representative of three independent experiments (FIG. 4C). Primary microglial cell were pretreated with LISPRO at 10 mM or vehicle (1% DMSO in medium) for 6 hours then incubated with 1 µM aged FITC-$A\beta_{42}$ for 1 hour. Cellular supernatants and lysates were analyzed for extracellular (top panel) and cell-associated (bottom panel) FITC-$A\beta_{42}$ using a fluorometer. Data are represented as the relative fold of mean fluorescence change (mean±SD), calculated as the mean fluorescence for each sample at 37° C. divided by mean fluorescence at 4° C. (n=4 for each condition presented) (***p<0.005). LDH assay showed no significant increase in cell toxicity induced by LISPRO up to 20 mM in both primary microglial cells and N9 microglial cells (data not shown).
Figure 4B:
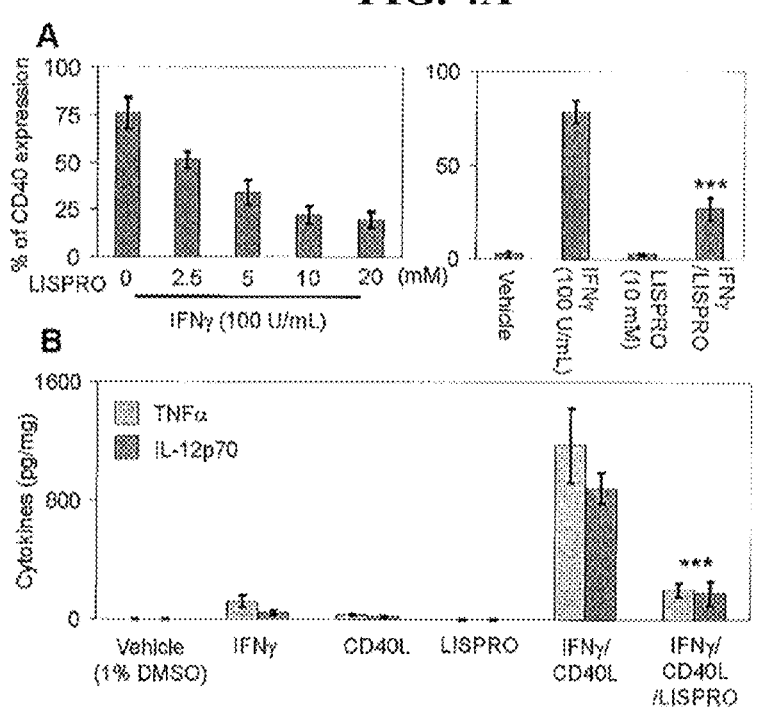
Figure 4C:
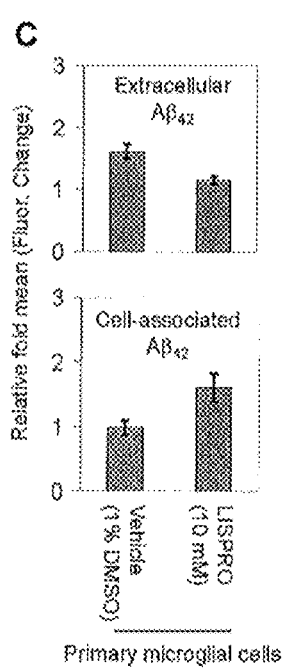
Figure 7A:
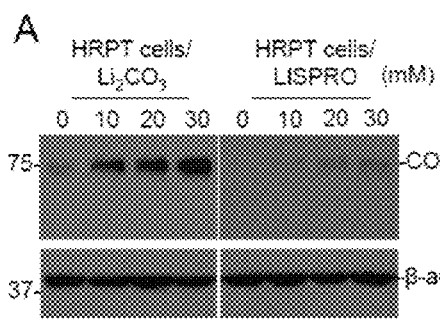
FIGS. 7A and 7B. LISPRO does not increase COX2 expression in human renal proximal tubule (HRPT) cells, but markedly reduces GSK3β activity. Human primary renal proximal tubule cells (ATCC) were cultured in InVitroGRO medium (BioreclamationIVT) and 24-well plates ($5 \times 10^5$/well), incubated overnight and treated with LISPRO, $Li_2CO_3$, LiCl or L-proline at 0 to 30 mM for 12 hours. These cells were then lysed with cell lysis buffer and analyzed by WB for COX2, total GSK3β and phospho GSK3β (Ser9 and Thr390) expression using anti-COX2 antibody (FIG. 7A, ABCAM®) and anti-phospho- and total GSK3β antibodies (FIG. 7B). Note that there were no notable differences in COX2 expression or GSK3β phosphorylation between $Li_2CO_3$ and LiCl. L-proline treatment induced no change in COX2 expression and GSK3β phosphorylation.
Figure 7B:
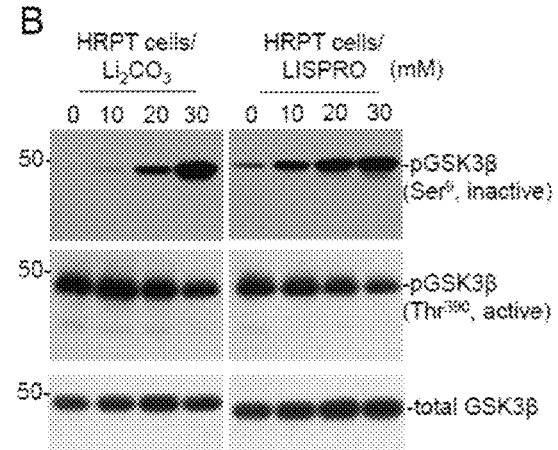
Figure 8:
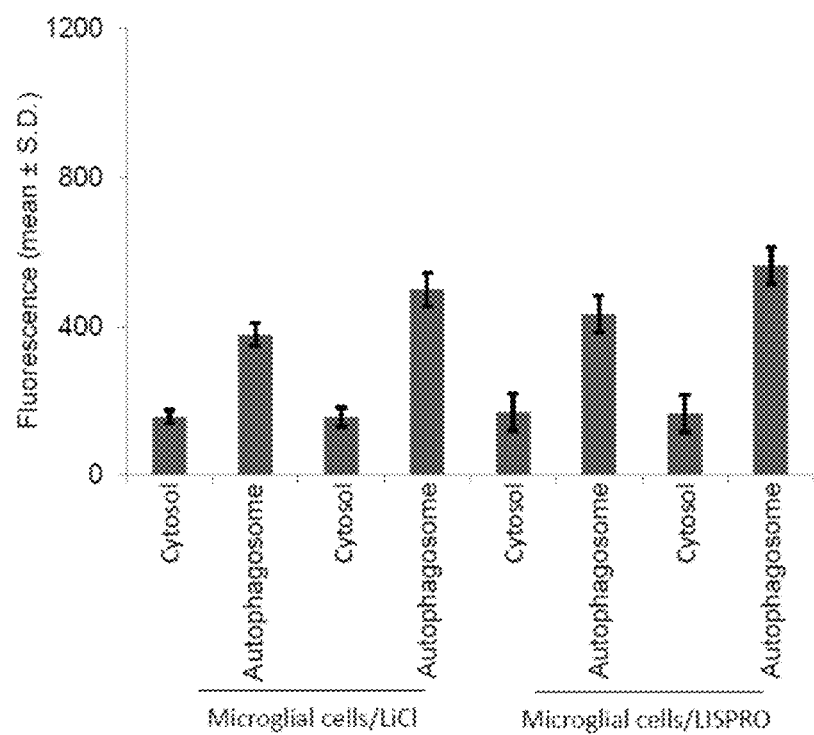
FIG. 8. LISPRO promotes autophagy in mouse primary microglial cells. Mouse primary microglial cells were plated in 8-well slide chambers ($10^6$/well), incubated overnight, and treated with LISPRO, $Li_2CO_3$, LiCl or L-proline at 10 mM for 18 hours. These cells were then permeabilized, washed, stained with LC3B rabbit polyclonal antibody and visualized with ALEXA FLUOR® 647 Goat anti-rabbit IgG (LC3B antibody kit, MOLECULAR PROBES®). The fluorescence intensity of the autophagosomes and the cytosol were quantified using SLIDEBOOK™ digital microscopy software. Note that there was no significance difference in the fluorescence intensity of the autophagosomes and the cytosol between $Li_2CO_3$ and LiCl (P>0.05). L-proline failed to promote any notable autophagy.

In order to further evaluate LISPRO's in vivo effects on reducing inflammatory immune responses and decreasing CD40 signaling, primary microglial cells were treated with LISPRO in the presence of IFNγ or/and CD40 ligand (CD40L, 1 μg/mL) for 8 hours and then examined pro-inflammatory microglial activation as assessed by flow cytometric (FACS) analysis and cytokine ELISA. FACS analysis showed significant dose-dependent decreases in IFNγ-induced CD40 expression following 8 hours of co-treatment with LISPRO. Data are represented as mean percentage of CD40-expressing cells (±SD) (FIG. 4A). Results are representative of two independent experiments. Microglial cell culture supernatants were collected and subjected to cytokine ELISA as indicated. Data are represented as mean pg of TNFα or IL-12p70 per mg of total cellular protein (±SD) (FIG. 4B). Results are representative of three independent experiments. Primary microglial cell were pre-treated with LISPRO at 10 mM or vehicle (1% DMSO in medium) for 6 hours and then incubated with 1 μM aged FITC-Aβ$_{42}$ for 1 hour. Cellular supernatants and lysates were analyzed for extracellular (top panel) and cell-associated (bottom panel) FITC-Aβ$_{42}$ using a fluorometer (FIG. 4C). Data are represented as the relative fold of mean fluorescence change (mean±SD), calculated as the mean fluorescence for each sample at 37° C. divided by mean fluorescence at 4° C. (n=4 for each condition presented) (***$P<0.005$). LDH assay showed no significant increase in cell toxicity induced by LISPRO up to 20 mM in primary microglial cells (data not shown).

Example 12

LISPRO Promotes Autophagy in Mouse Primary Microglial Cells

Figure 19:
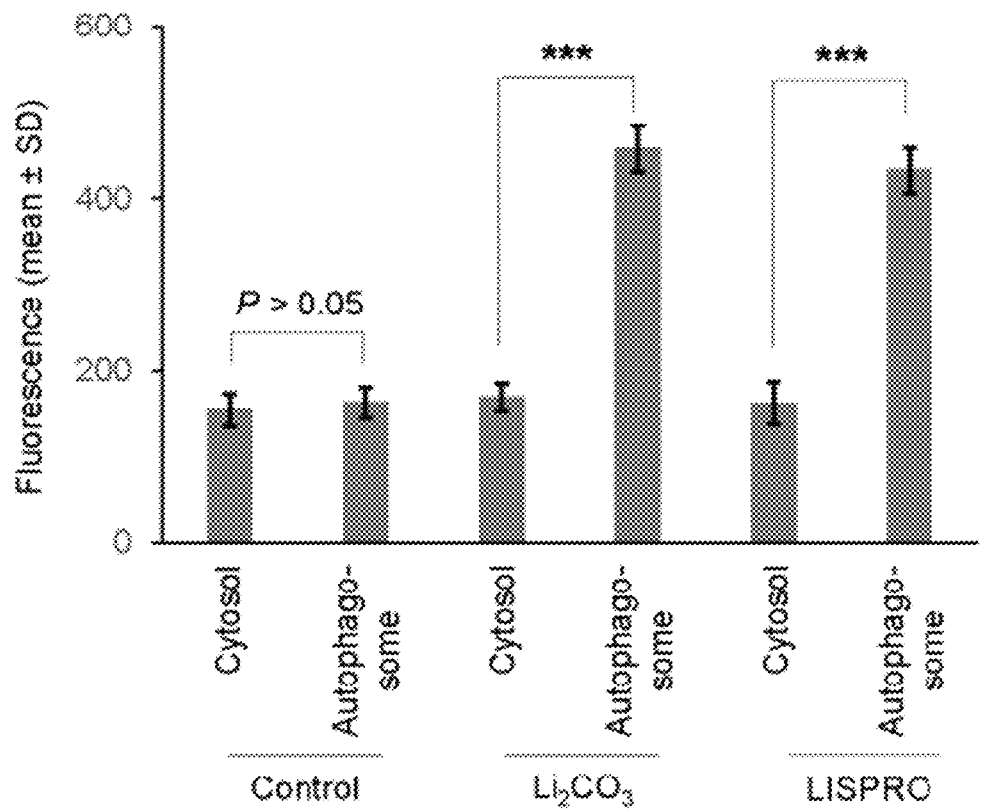
FIG. 19 shows that LISPRO promotes autophagy in murine primary microglial cells (described in Example 12).

Mouse primary microglial cells were treated with LISPRO, $Li_2CO_3$, LiCl or L-proline at 10 mM or PBS (Control) for 18 hours. These cells were then permeabilized, stained with LC3B rabbit polyclonal antibody, and visualized with Alexa Fluor® 647 Goat anti-rabbit IgG (LC3B antibody kit, Molecular Probes®). The fluorescence intensity of the autophagosomes and the cytosol were quantified using Slidebook™ digital microscopy software (mean±SD) (FIG. 19). Both LISPRO and $Li_2CO_3$ treatments showed significant enhancement of autophagy (***$P<0.001$). Note that there was no significance difference in the fluorescence intensity of the autophagosomes and the cytosol between $Li_2CO_3$ and LISPRO or LiCl ($P>0.05$). L-proline failed to promote any notable autophagy.

Example 13

Figures 20A, 20B:
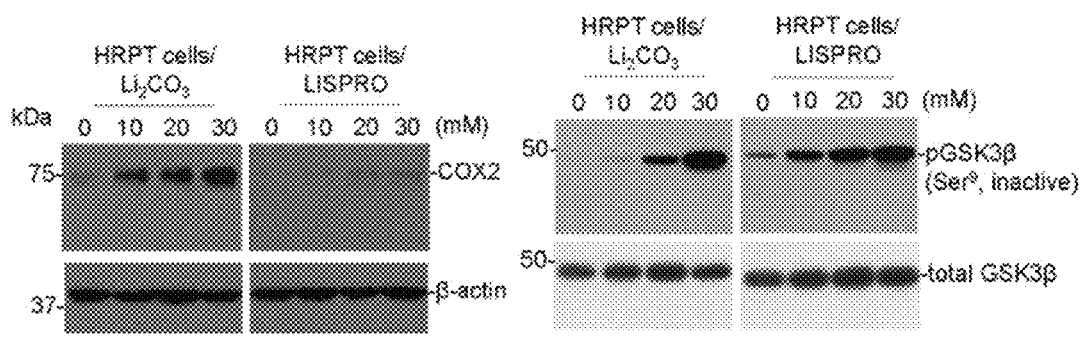
FIGS. 20A-B show that LISPRO reduces GSK3β activity in human renal proximal tubule (HRPT) cells, but does not increase COX2 expression (described in Example 13).

LISPRO Markedly Reduces GSK3β Activity in Human Renal Proximal Tubule (HRPT) Cells, but does not Increase COX2 Expression Human primary renal proximal tubule cells (ATCC® PCS-400-010™) were cultured in InVitroGRO medium (BioreclamationIVT) and treated with LISPRO, $Li_2CO_3$, LiCl or L-proline at 0 to 30 mM for 12 hours. These cells were then lysed with cell lysis buffer and analyzed by WB for COX2, total GSK3β and phospho GSK3β (Ser$^9$) expressions using anti-COX2 antibody (FIG. 20A, Abcam®) and anti-phospho- and total GSK3β antibodies (FIG. 20B). There were no notable differences in COX2 expression or GSK3β phosphorylation between $Li_2CO_3$ and LiCl. L-proline treatment induced no change in COX2 expression and GSK3β phosphorylation.

Example 14

LISPRO does not Increase COX2 Expression In Vivo

Figure 21A:
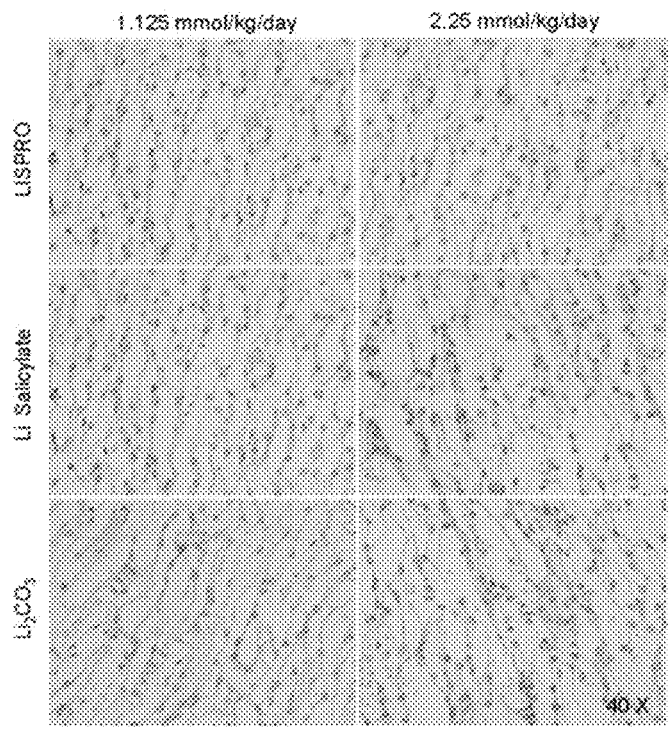
FIGS. 21A, and 21B-1 to B-3 show that LISPRO does not increase COX2 expression in vivo (described in Example 14).
Figures 1, 21B:
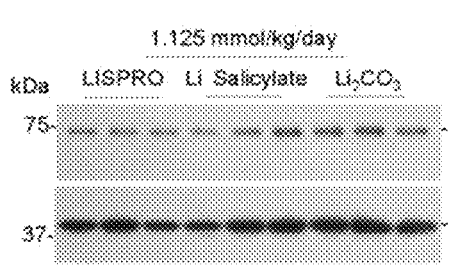
Figures 2, 21B:
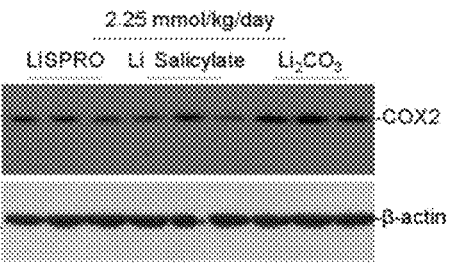
Figures 3, 21B:
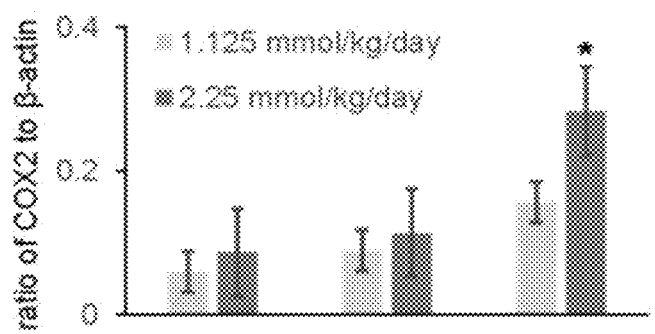

C57BL/6J male mice (6 weeks old, the Jackson Laboratory) were fed for 1 or 2 weeks with 3 diets providing lithium at 1.125 or 2.25 mmol/kg/day as indicated or control NIH31 diet. These diets consisted of a standard NIH31 chow supplemented with $Li_2CO_3$ (0.25 g/kg or 0.5 g/kg), lithium salicylate (Li Salicylate, 0.975 g/kg or 1.95 g/kg) or LISPRO (1.75 g/kg or 3.5 g/kg). All mice received normal drinking water ad libitum. Kidneys were collected after treatment and analyzed by immunohistochemistry for COX2 expression in the renal medulla (FIG. 21A). In addition, the kidney microsomal proteins were extracted to assess COX2 expression by WB (FIGS. 21B-1, 21B-2). Data are expressed as mean±SD in duplicates from six mice in each group (FIG. 21B-3). Statistical analysis was carried out using ANOVA (*P<0.05, n=6 for LISPRO, $Li_2CO_3$ or lithium salicylate, n=3 for control NIH3 diet). There was no significant difference in kidney microsomal COX2 expression levels between LISPRO-, lithium salicylate- and control NIH31 diet treated mice at 1.125 mmol/kg/day and 2.25 mmol/day (P>0.5).

Example 15

Figure 22A:
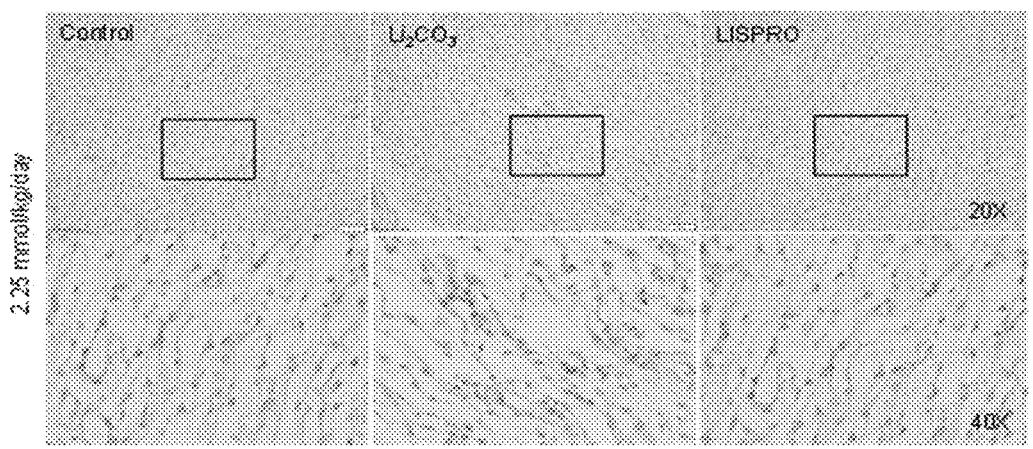
Figures 1, 2, 22B:
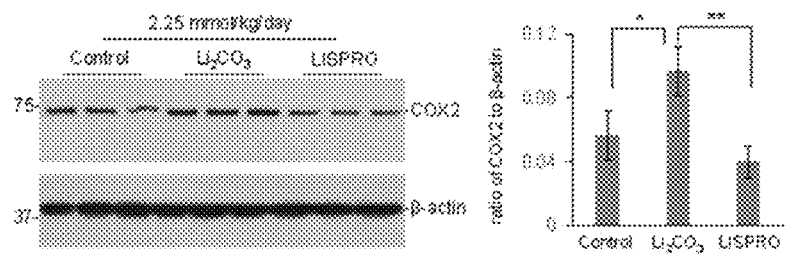

LISPRO does not Increase COX2 Expression in Tg2576 Mice Following 8-Week-Treatment Tg2576 mice (8 months old) were treated for 8 weeks with 2 diets providing lithium at 2.25 mmol/kg/day, consisting of standard NIH31 chow supplemented with $Li_2CO_3$ (0.5 g/kg) or LISPRO (3.5 g/kg), or control NIH31 chow as described in FIGS. 14A-C, above. All mice received normal drinking water ad libitum. Kidneys were collected after treatment and analyzed by immunohistochemistry for COX2 expression in the renal medulla (FIG. 22A). The kidney microsomal proteins were extracted to assess COX2 expression by WB (FIGS. 22B-1, 22B-2). Statistical analysis was carried out using ANOVA (*P<0.05, **P<0.01). There was no significant difference in kidney microsomal COX2 expression levels between LISPRO-treated and control mice (P>0.05).

Example 16

Short-Term Plasma and Brain Pharmacokinetics of LISPRO and $Li_2CO_3$

Figure 23A:
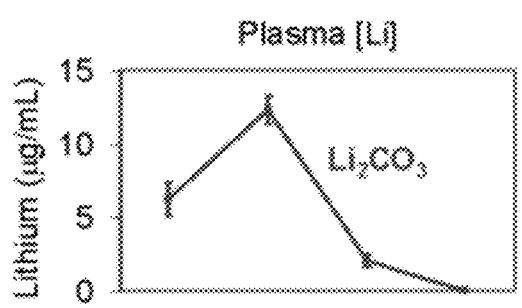
FIGS. 23A-D show short-term plasma and brain pharmacokinetics of LISPRO and $Li_2CO_3$ (described in Example 16).
Figure 23B:
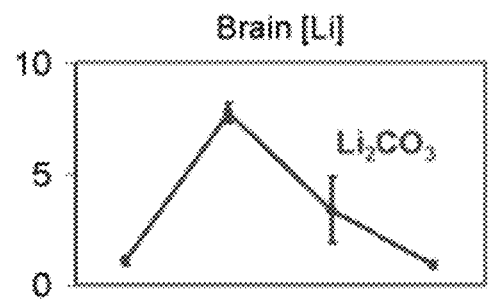
Figure 23C:
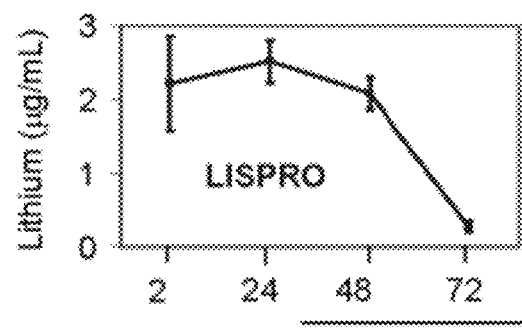
Figure 23D:
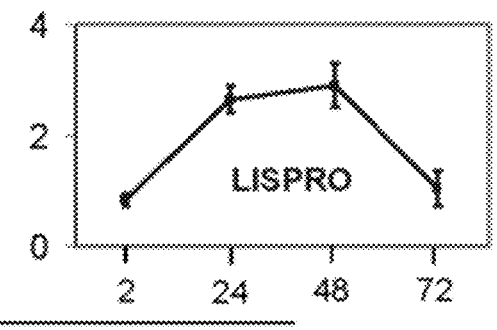

Male Sprague-Dawley rats (n=3 per formulation per time point) were dosed with 4 mEq/kg of lithium via oral gavage as LISPRO or $Li_2CO_3$. Plasma and brain lithium levels were determined at 2, 24, 48, and 72 h by AAS. $Li_2CO_3$ plasma lithium concentration versus time (mean±SD) is shown in FIG. 23A. $Li_2CO_3$ brain lithium per gram of wet weight versus time (mean±SD) is shown in FIG. 23B. LISPRO plasma lithium concentration versus time (mean±SD) is shown in FIG. 23C. LISPRO brain lithium per gram of wet weight versus time (mean±SD) is shown in FIG. 23D. The plasma pharmacokinetics of $Li_2CO_3$ produced a sharp peak and rapid elimination with nearly undetectable levels at 48 hours (FIG. 23A). This produced a concomitant spike in brain lithium levels at 24 hours (FIG. 23B). LISPRO produced elevated lithium plasma levels at the earliest time point (2 hours) (FIG. 23C). The plasma lithium levels peaked at 24 hours and remained elevated at 48 hours before becoming almost undetectable at 72 hours. LISPRO produced steady brain levels of lithium at 24 hours and 48 hours (FIG. 23D).

Example 17

Long-Term Serum and Brain Pharmacokinetics of LISPRO, Lithium Salicylate, and Lithium Carbonate C57BL/6J mice were fed for 1 or 2 weeks with 3 diets providing lithium at 1.125 or 2.25 mmol/kg/day as indicated followed by analysis of serum (FIGS. 24A-1, 24B-1) and brain lithium levels (FIGS. 24A-2, B-2) by AAS. All mice received normal drinking water ad libitum. Statistical analysis was carried out following ANOVA analysis. There was no significant difference in lithium levels in serum and brain homogenate between $Li_2CO_3$— and lithium salicylate-treated mice (P>0.5). There was no detectable lithium in serum and brain homogenates in control NIH31 diet-fed C57BL/6J mice (data not shown).

Example 18

Figure 25A:
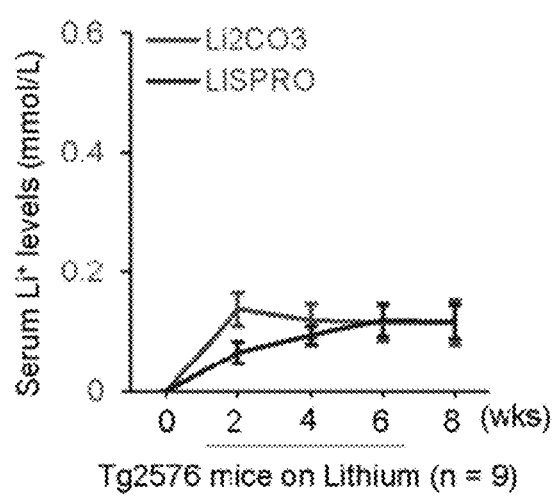
FIGS. 25A-B show long-term serum and brain pharmacokinetics of LISPRO or lithium carbonate in Tg2576 mice (described in Example 18).
Figure 25B:
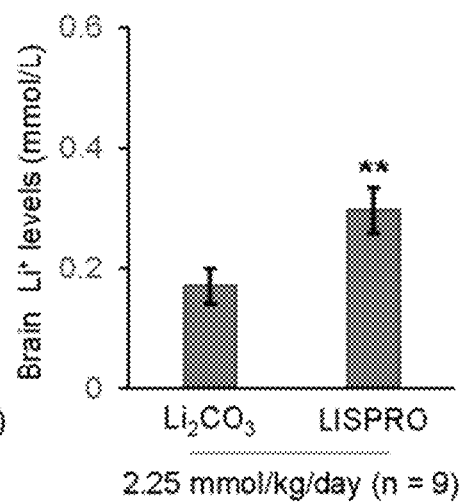

Long-Term Serum and Brain Pharmacokinetics of LISPRO or Lithium Carbonate in Tg2576 Mice As described in FIGS. 14A-C, above, Tg2576 mice were treated for 8 weeks with 2 diets providing lithium at 2.25 mmol/kg/day as indicated followed by analysis of serum (FIG. 25A) and brain (FIG. 25B) lithium levels by AAS. Statistical analysis was carried out using ANOVA analysis (**P<0.001, n=9 for LISPRO or lithium carbonate). There was no detectable lithium in serum and brain homogenates in control NIH31 diet-fed Tg2576 mice (data not shown).

Example 19

Figure 13:
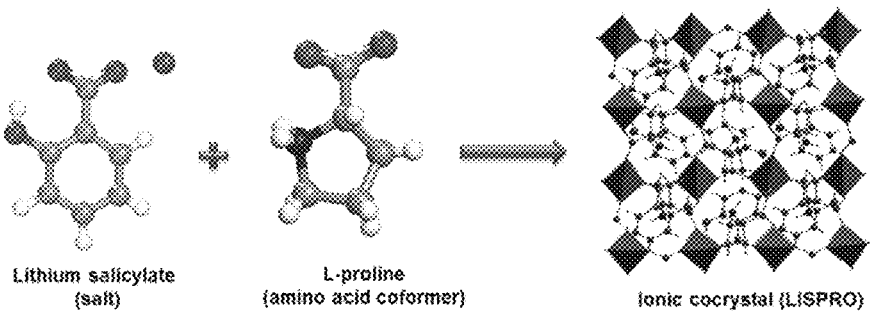
FIG. 13 shows the reaction scheme of lithium salicylate (a salt) and L-proline (an amino acid conformer) producing LISPRO (an ionic co-crystal).

Examination of Cognitive Impairment in 3XTg-AD Mice Following Oral LISPRO Treatment Despite effective medicinal uses, current FDA-approved lithium pharmaceutics (lithium carbonate) are plagued with a narrow therapeutic window that requires regular monitoring of plasma lithium levels and blood chemistry by a clinician to mitigate adverse events. This is especially troublesome in the elderly where AD is most prevalent. These patients are frequently on poly-pharmacy and have low compliance rates. Further, many patients undergoing lithium therapy find the side effects to be unbearable, which discourage physicians from utilizing this treatment. This suggests a need to develop a safer lithium formulation for treatment of AD. Thus, the inventors have employed crystal engineering techniques to create an ICC of lithium (LISPRO) which should effectively reduce AD pathologies with less frequent or lower doses than that of the most commonly used lithium compound, lithium carbonate ($Li_2CO_3$) (FIG. 13). This is in part due to LISPRO's enhanced pharmacokinetic profile relative to $Li_2CO_3$. Treatment of rats with LISPRO delivering lithium at 4 mEq/kg provided consistently elevated levels of lithium in the plasma and brain out to 48 hours (FIGS. 23C, D). Conversely, $Li_2CO_3$ was almost undetectable at 48 hours in the plasma and produced a large spike in the plasma and brain at 24 hours post dosage (FIGS. 23A, B; (20)). This type of pharmacokinetic profile can contribute to the toxicity of lithium given its narrow therapeutic window. Lippman and Evans (31) suggested that an ideal lithium preparation would attenuate high blood level peaks and exhibit gradually declining blood concentrations. This has been the driving logic behind the development and evaluation of many controlled-release formulations and suggests LISPRO may be effective with less frequent or lower dosing requirements (32-34).

The inventors have confirmed that low doses of LISPRO are safe and effective in reducing AD pathology. The inventors have shown that Tg2576 mice fed with a LISPRO supplemented diet delivering lithium at 2.25 mmol/kg/day for 8 weeks, has no effect on renal COX2 activity (FIGS. 20-22), a biomarker of renal toxicity (21, 35), while markedly reducing abnormal β-amyloid pathology, tau phosphorylation and neuroinflammation (FIGS. 14-16). In addition, LISPRO treatment did not induce tissue pathological damage in the heart, kidney, liver, and lung by a general autopsy. In contrast, equimolar doses of lithium carbonate enhanced renal COX2 expression (FIGS. 20-22) while having little or no impact on AD pathology (FIGS. 14-16). The inventors have also shown that LISPRO at the effective dose yields higher lithium levels in the brain compared with equimolar doses of lithium carbonate, while producing low nontoxic steady state levels in the periphery (0.1 mM, FIGS. 24 and 25). Indeed, the improved pharmacokinetics of LISPRO in the blood and brain explains its enhanced effectiveness and safety for treating AD compared with lithium carbonate. These results confirm and build upon recent studies indicating that low lithium doses can be effective in AD treatment (14, 27). Moreover, the salicylate group in LISPRO may underlie many of its anti-inflammatory effects which were not seen with lithium carbonate.

The inventors wish to further examine whether oral administration of LISPRO could improve neurocognition in 3XTg-AD mice. These mice were developed from single-cell embryos from mice bearing the presenilin PS1M146V knock-in mutation with co-injection of two independent mutant human transgenes, Swedish mutant amyloid precursor protein (APPswe) and microtubule-associated protein tau (tauP301L) (36). The resulting triple-transgenic AD mice show progressive development of plaques and tangles. Extracellular plaques and NFTs were originally found in the neocortex and hippocampus accompanied by significantly impaired long- and short-term memory retention as assessed by contextual fear testing at six months of age (37-39). Recent studies indicate that the development of AD pathology in these mice is somewhat delayed from that shown in earlier reports, with Aβ plaques and tau pathology becoming readily detectable around 10 months of age ((37, 39-41)). The inventors will investigate if long-term 4 month treatment of these mice with LISPRO reduces cognitive impairment observed after aging (10-14 months of old). The inventors will investigate if LISPRO-elicited cognitive improvement is correlated with reductions in AD-like pathology (Aβ levels/β-amyloid deposits, NFT formation and neuroinflammation).

As shown in FIG. 26, mouse brain tissue sections prepared from three 3XTg-AD mice at 10 months of age (n=3) were immunohistochemistry stained with anti-Aβ antibody (4G8) (FIGS. 26A-1, 26A-2) or anti-phospho-tau (Thr$^{231}$) antibody [p-tau (Thr$^{231}$)] (FIGS. 26B-1, 26B-2, 26B-3). Three 3XTg-AD mice showed similar AD-like pathology, as was expected. Thus, these mice will be fed with LISPRO-containing chow, in comparison with Li$_2$CO$_3$, prophylactically between 6 and 10 months of age and therapeutically between 10 and 14 months of age. Overall, this model should provide robust Aβ and tau/NFT pathology while also addressing their response to LISPRO prophylaxis and treatment.

Three or four month-old 3XTg-AD mice (Stock No. 034830) and their recommended controls (WT, B6129SF2/J (Stock No. 101045), a cross between B6 females and 129S males) will be purchased from Jackson laboratories through the MIVIRRC. The inventors will determine if LISPRO can protect 3XTg-AD mice from cognitive impairment (prophylactic effectiveness) or improve cognitive performance after the onset of such impairment (therapeutic effectiveness). Therefore, LISPRO oral administration will begin in the prophylactic group at 6 months of age, prior to visible histological Aβ deposit and NFTs formation, and continue until between 10 and 10.5 months of age. The effectiveness of three doses of LISPRO will be tested to determine the minimum effective dose: 1.75 (minimum), 3.5 (moderate) and 7 g/kg/chow (maximum), delivering lithium at 1.125, 2.25 and 4.5 mmol/kg/day, respectively, as detailed in Table 4. In order to reduce potential lithium toxicity in the kidney, a saline bottle will be provided in addition to water in all cages. Behavior of animals in these groups and in non-transgenic untreated wild-type mice will be evaluated after treatment, with a established behavioral battery which measures multiple cognitive domains, including open field, novel object recognition, radial arm water maze, and contextual and cued fear conditioning (42-46). For the therapeutic group, LISPRO treatment will begin at 10 months and continue through 14 months of age. During the final week of treatment, between 14 and 14.5 months of age, the animals in this group and in non-transgenic littermates will be evaluated with the same behavioral battery used for the prophylactic group.

TABLE 4

|  | Treatment Group | Mouse Strain | #Mice (♂/♀) | LISPRO (or Li$_2$CO$_3$), g/kg of NIH31 chow | Treatment Duration |
|---|---|---|---|---|---|
| 6 months old | prophylactic | 3XTg-AD | 16(8/8) | 0 | 4 months |
|  | prophylactic | 3XTg-AD | 16(8/8) | 1.75 (0.25) |  |
|  | prophylactic | 3XTg-AD | 16(8/8) | 3.5 (0.5) |  |
|  | prophylactic | 3XTg-AD | 16(8/8) | 7 (1) |  |
|  | Totals → |  | 4 × 64 (32/32) |  |  |
|  | prophylactic | WT | 8(4/4) | 0 | 4 months |
|  | prophylactic | WT | 8(4/4) | 1.75 (0.25) |  |
|  | prophylactic | WT | 8(4/4) | 3.5 (0.5) |  |
|  | prophylactic | WT | 8(4/4) | 7 (1) |  |
| 10 months old | Totals → |  | 4 × 32 (16/16) |  |  |
|  | therapeutic | 3XTg-AD | 16(8/8) | 0 | 4 months |
|  | therapeutic | 3XTg-AD | 16(8/8) | 1.75 (0.25) |  |
|  | therapeutic | 3XTg-AD | 16(8/8) | 3.5 (0.5) |  |
|  | therapeutic | 3XTg-AD | 16(8/8) | 7 (1) |  |
|  | Totals → |  | 4 × 64 (32/32) |  |  |
|  | therapeutic | WT | 8(4/4) | 0 | 4 months |
|  | therapeutic | WT | 8(4/4) | 1.75 (0.25) |  |

TABLE 4-continued

| Treatment Group | Mouse Strain | #Mice (♂/♀) | LISPRO (or Li$_2$CO$_3$), g/kg of NIH31 chow | Treatment Duration |
|---|---|---|---|---|
| therapeutic | WT | 8(4/4) | 3.5 (0.5) | |
| therapeutic | WT | 8(4/4) | 7 (1) | |
| Totals → | | 4 × 32 (16/16) | | |

The behavioral battery will include the Balance Beam Task, to evaluate vestibular and general motor function and account for any problems that may occur with the rest of the tests due to motor (and not behavioral/cognitive) impairment. The contextual and cued fear-conditioning tests have been well demonstrated to be valid correlates of β-amyloid deposition and AD-like memory deficits in various AD mouse models, including 3XTg-AD mice (37-39, 47-53). In parallel, the inventors will include the traditionally clinically used lithium (Li$_2$CO$_3$) as control for LISPRO in both prophylactic and therapeutic paradigms as detailed in Table 4.

It is expected that LISPRO treatment will reverse or abolish long-term and short-term memory impairment as assessed by the behavioral battery at 10-10.5 months of age in the prophylactic group and 14-14.5 months of age in the therapeutic group. It is also expected that LISPRO-elicited cognitive improvement to correlate with reductions in AD-like pathology (Aβ levels/β-amyloid deposits NFT formation and neuroinflammation). Specifically, minimum doses of LISPRO will inhibit APP γ-secretase proteolytic processing and modulate GSK3α/β signaling pathway in the transgenic mice, thereby improving cognitive performance. This would reflect LISPRO's ability to provide improved lithium bioavailability in the brain (FIGS. 23 and 25; (20)), even at low nontoxic levels in the periphery. In addition, it is expected that LISPRO will be more effective than equimolar doses of Li$_2$CO$_3$ on abolishing AD-like cognitive impairment in the 3XTg-AD mice.

Example 20

Determination of AD-Like Pathological Changes in 3XTg-AD Mice Following Oral LISPRO Treatment In preliminary studies using N2a, HeLa/tau and SH-SY5Y cell cultures, it was found that LISPRO inhibits abnormal Aβ generation (FIG. 1A) and tau phosphorylation (FIG. 3), while leaving Notch processing unaltered (FIG. 1B). Likewise, LISPRO treatment reduces β-amyloid (FIG. 14) and tau pathology in Tg2576 mice (FIG. 16). It was found that LISPRO potentially mediated these therapeutic effects via multiple mechanisms, including promotion of anti-inflammatory/Th2 responses (FIG. 16), neurogenesis (FIG. 5), neural stem cell differentiation (FIGS. 17 and 18), microglial phagocytosis of Aβ (FIG. 4) and microglial autophagy (FIG. 19), while inhibiting microglial activation mediated by proinflammatory IFNγ and CD40 signaling (FIG. 4) and neuronal GSK3β activity (FIGS. 2, 3, and 15).

Taken together, the above data suggest that targeting multiple signaling pathways, including inhibition of γ-secretase APP cleavage, modulation of GSK3β activation, reduction of tau hyperphosphorylation, neural stem cell differentiation, rebalance of anti-/pro-inflammatory responses to Aβ exposure and microglial autophagy may mediate mechanisms underlying LISPRO-reduced AD-like pathology. The inventors intend to fully characterize and quantify LISPRO's therapeutic potential in AD mice against multiple pathological targets, including β-amyloidosis, tau hyperphosphorylation/NFT formation and neuroinflammation, in the triple-transgenic model of AD (3XTg-AD mice) (36). Furthermore, the inventors will investigate if any cognitive improvement elicited by this treatment could be correlated with reductions in AD-like pathology.

The minimum and safe dosage of LISPRO for inhibiting Aβ/NFT pathology and neuroinflammation in 3XTg-AD mice will be determined. The three doses tested in this Example will be the same as that used for Example 19, delivering lithium at 1.125 (minimum), 2.25 (moderate), and 4.5 mmol/kg/day (maximum). The inventors will orally treat 3XTg-AD mice prophylactically and therapeutically with LISPRO in chow, using the same number and ages of mice and treatment/dose sub-grouping as in Example 19 (Table 4). In parallel, the inventors will include the traditionally clinically used Li$_2$CO$_3$ as control for LISPRO in both prophylactic and therapeutic paradigms. At sacrifice, blood will be collected, the mice will be perfused with saline, and brains will be bisected sagittally. The left half of the brain will be immersion fixed in paraformaldehyde for histological processing (54) and the right half will be dissected into various regions, including hippocampus and anterior and posterior cortex, and rapidly frozen for subsequent biochemical analyses (54, 55). For sub-dissection of the cortex, the inventors will bisect laterally at the hippocampal commissure to yield anterior and posterior portions. A concentrated macromolecular fraction will be used for ELISA (54, 55) and the remaining supernatants as well as blood samples will be further processed for AA Spectroscopy analysis of lithium in both brain tissues and plasma per our recent studies (20). This will provide insight as to LISPRO's brain anatomical penetrance by region. The primary neuropathological analyses will be Aβ formation, which will be measured by both Aβ immunohistochemistry and Congo red staining, as well as biochemically by ELISA (Aβ$_{40,42}$) and WB analysis for Aβ as well as sAPPα, β and CTF-α, β (54). Dependent analytes are summarized in Table 5.

TABLE 5

| Method | Marker | Target |
|---|---|---|
| Immunohistochemistry (left hemispheres) (Rezai- | Aβs | Diffuse and compact amyloid deposits |

TABLE 5-continued

| Method | Marker | Target |
|---|---|---|
| Zadeh et al., 2005; 2009; Zhu et al., 2011a, b) | Congo red dye | Compact amyloid deposits |
| | Iba1, CD11b, CD45, MHC | Activated microglia |
| | Alz50, MC-1, and Aβ39 | Conformational tau epitopes |
| | PHF-1 (phospho-396/404) | Phosphorylated tau epitopes |
| Western blot analysis (right hemispheres) (Rezai-Zadeh et al., 2005; 2008 2009) | hAPP | Expression of the transgene |
| | α, β-CTF, sAPPα, β | Relative α, β-secretase activity |
| | human tau-specific antibody, E1 WKS45 (antibody that recognizes mouse and human tau) | Insoluble and soluble tau |
| | phospho-GSK3α/β | Relative activity of GSK component of γ-secretase complex |
| | NFkB, MAPK, autophagy (IMPase) | Activity of this M1 promoting intracellular pro-inflammatory signaling protein complex |
| | Peroxisome proliferator-activated receptor-γ (PPARγ) | Activity of this M2 promoting intracellular anti-inflammatory signaling protein complex |
| ELISA (Rezai-Zadeh et al., 2005; 2009; Zhu et al., 2011a, b) | Brain Aβ$_{40}$ and Aβ$_{42}$ | Oligomer Aβ and full length Aβ; |
| | α, β, γ secretase | Relative α, β, γ secretase activity |
| AA Spectroscopy analysis (Smith et al., 2010; 2013) | Lithium | Total lithium levels and bioavailability in brain and plasma |

The inventors will examine hAPP levels and processing into α/β-CTFs and sAPPα/β using WB analysis (54). Furthermore, the inventors will measure α-, β- and γ-secretase cleavage activity using fluorescence/ELISA kits (R&D; (54, 55). Given that LISPRO may inhibit γ-secretase cleavage of APP through modulation of GSK3α/β activation, and thereby modulate tau phosphorylation, the inventors will determine phospho-tau levels in brain homogenates of LISPRO-treated mice by WB with anti-phospho-tau antibodies (including PHF1) (56). The inventors will measure conformational tau epitopes with Alz50, MC-1, and Aβ39 (56), since these conformational changes are critical to NFT formation caused by hyperphosphorylation. Further total soluble and insoluble tau will be measured with E1 and WKS45 antibodies as previously described via WB (57). Finally, the inventors will correlate these NFT-like structures with Aβ levels/deposition and microglia-associated inflammation (Iba1, CD11b and CD45 staining) (56, 58) in these mice. To monitor LISPRO bioavailability, tail blood will be drawn once per month over 4 months and analyzed via AA Spectroscopy analysis for levels of total lithium in plasma (20, 59). LISPRO bioavailability will be correlated with anti-amyloidogenic APP processing and phospho-tau. Many γ-secretase inhibitors described in the literature demonstrate an accumulation of APP stubs in the membrane, which may have long term effects in vivo. It will be possible to detect these α- and β-secretase-generated C-terminal APP stubs via characterization of their levels by WB in both the supernatant (non-membrane associated stubs) and cell extracts (membrane associated stubs) of the brain homogenates of the mice as performed previously laboratory (54, 55). As further mechanisms whereby LISPRO may mediate beneficial effects against AD pathology, the levels of microglial M1 and M2 inflammatory signaling mediators will be determined, including NF-kB, MAPK, and PPARγ. Since LISPRO may reduce AD pathology by inhibition of IMPase, thereby enhancing autophagy of neurotoxic substrates such as Aβ (60), these activities will be also be determined in the LISPRO-treated mice.

Recent studies indicate that LISPRO may also reduce AD pathology and cognitive impairment by enhancing neurogeneration (FIGS. 5, 17, and 18; (20, 61)). Therefore, the inventors will stain neurons with several neurogenesis markers within the neurogenic niches (dentate gyrus, suventricular zone, olfactory epithelium). BrdU will be injected for 6 consecutive days before sacrifice for determination of total proliferating cells. Neuroprogenitor cells will be detected by Ki67 and GFAP, newborn neurons will be detected by doublecortin (DCX) and PSA-NCAM, and mature neurons will be detected by NeuN and calbindin. As LISPRO may act as a pan γ-secretase inhibitor (either directly or indirectly), modulating T cell immunity and eliciting gut and other pathologies as side effects, the following further measures will be made. γ-secretase inhibitors have been shown to alter notch processing in such a way that may cause intestinal goblet cell metaplasia and induction of genes which regulate gut secretary lineage differentiation. As such, the inventors will use the methods of Milano (62) to analyze the acidic, basic, sulphomucin and sialomucin contents of goblet cells, as well as their Hemotoxylin Eosin staining characteristics. In addition, the degree to which damage is occurring in gastrointestinal tissues will be evaluated by determining wet weight and histology of the stomach, large and small intestines and intestinal goblet cells (62).

Given that lithium may have some potential toxicity in the kidney, liver, spleen, lung, and heart, these organs will also be subjected to careful microscopic, biochemical and functional examination for pathological changes. The liver will be analyzed histologically for portal cirrhosis, fat vacuoles and areas of necrosis and biochemically for alanine aminotransferase (ALT/AST) activity, using a diagnostic kit (New Zealand). Renal pathology and the presence of diabetes insipidus will be determined by analysis of glomerular and tubular fibrosis, GFR (63) as well as COX2 expression by immunoblotting and immunohistochemistry (21). Cardiovascular pathology will be assessed by measuring myocardial levels of antioxidant enzymes (64), as well as monitoring heart rate, blood pressure, plasma sodium, potassium and calcium levels, as well as vascular and myocardial levels of ATP (65). The presence of hypothyroidism will be determined by measuring plasma levels of T3, T4 and TSH (66). Affective disorders will be determined by the open field test, particularly watching for signs of hypokinesia and reduced exploratory behavior or rearing (67, 68). Motor deficits will be determined by the vertical pole test (69).

It is expected that LISPRO will reduce Aβ deposits and tau phosphorylation as well as total soluble and insoluble tau with minimum doses to a much higher degree than $Li_2CO_3$. This would reflect LISPRO's ability to provide improved lithium bioavailability in the brain compared with $Li_2CO_3$, even at low nontoxic levels in the periphery (FIGS. 23-25). Data generated from the measurement of APP processing, as examined by the analysis of AD-like tau pathology, sAPPα and β and α- and β-CTFs, will be informative as to the actions of LISPRO for modulating GSK3α/β signaling and reducing γ-secretase cleavage of APP. In addition, the results will provide information regarding the mechanism for LISPRO's beneficial effects, including reduction of neuroinflammation, enhancement of microglial autophagy and enhancement of neural stem cell differentiation. This will provide further information regarding LISPRO's therapeutic effect while utilizing minimum doses to reduce AD-like pathology. Such data will be suggestive of more safe and effective lithium treatments which would be applied to the human condition.

Example 21

Characterization of Glial Activation State Ex Vivo in Young and Aged 3XTg-AD Mice Following Oral LISPRO Treatment Recent studies have identified many important bioactivities of lithium that may contribute to its therapeutic efficacy in its current FDA-approved indications and beyond. For example, lithium exerts neuroprotective effects, in part, by increasing BDNF. Chronic lithium treatment increases expression of BDNF in rats (5) and humans (6) which can lead to reversal of learning and memory deficits through promotion of neurogenesis and long-term potentiation (LTP). In addition, lithium attenuates production of inflammatory cytokines like IL-6 and NO in activated microglia (7). As a follow up to the observation that LISPRO reduces tau and β-amyloid pathology in Tg2576 mice (FIGS. 14 and 15), the inventors further discovered that LISPRO promoted anti-inflammatory/Th2 responses and decreased levels of pro-inflammatory CD40L in the CNS of these mice (FIG. 16). In addition, using microglial cultures, the inventors found that LISPRO reduces pro-inflammatory microglial activation-induced by IFNγ and CD40 signaling and promoted microglial phagocytosis (FIG. 4). This is important as primary microglial cells exposed to LPS or IFNγ are characterized by a pronounced pro-inflammatory phenotype, which is comparable to the classical M1-like state in macrophages (70) and believed to promote Aβ-like pathology (71). Moreover, the phagocytic capacity of these cells is dramatically decreased. On the other hand, microglia treated with IL-10 or IL-4 become anti-inflammatory, called M2-deactivated or M2-alternatively activated microglia. Microglia exposed to oligomeric, fibrillary or full length Aβ present an M1-like phenotype (70), along with a diminished phagocytic capacity and enhanced expression of a pro-inflammatory gene profile. These events will not only decrease the microglial clearance of Aβ but also increase neuronal production of this peptide (28), leading to a vicious cycle which seems to fuel AD progression. Interestingly, a most recent study indicates a role for γ-secretase activity in microglial functions critical for the phagocytosis/clearance of β-amyloid deposits (72). Thus, the results suggest that LISPRO not only reduces Aβ by inhibiting γ-APP cleavage but may also support microglial function in the phagocytosis and clearance of Aβ. Thus, an objective will be to determine the relative importance of LISPRO-mediated activation of microglial Aβ phagocytosis and anti-inflammatory profile in correlation with its ability to promote non-amyloidogenic APP processing.

Given that the current data show that LISPRO induces the M2 phenotype through down-regulation of microglial CD40 signaling (FIGS. 4 and 16; (73, 74), the inventors will test the hypothesis that LISPRO treatment preserves this M2 phenotype in primary microglia from young and aged 3XTg-AD mice after the development of AD amyloid pathology and cognitive impairment. The inventors will test the hypothesis that LISPRO preserves the M2 phenotype ex vivo in primary microglia isolated from young or aged 3XTg-AD mice (10 and 14 months, respectively) treated with LISPRO as described for Example 19, in comparison with those fed control diets. The inventors will fully examine microglial pro-inflammatory MAPK, NF-kB and CD40 signaling pathways, cytokine secretion, Aβ phagocytosis capacity, markers of M1 or M2 phenotype and microglial autophagy (IMPase) ex vivo via immunohistochemistry, WB, RT-PCR and Flow analysis in primary microglia isolated from these mice. These methods and assays have been well established as previously published (56, 73, 75). The culturing of primary microglial cells from young and aged mice has been routinely conducted (28, 29, 73).

Since normal aging of the human brain is characterized by an increase in newly synthesized oligomers of Aβ and expression of pro-inflammatory cytokines (76, 77), along with a decrease of anti-inflammatory cytokines, such as IL-10 (78) and IL-4 (79, 80), it is to be expected that microglial cells isolated from older 3XTg-AD mice will be more easily skewed towards an M1-like phenotype than those isolated from young mice. However, microglia isolated from older 3XTg-AD mice treated with LISPRO at minimum dose will strongly preserve an M2 phenotype, in comparison with those treated with $Li_2CO_3$ or control diet, as shown with young mice in our preliminary results (FIGS. 4 and 16). A preserved M2 phenotype in microglia derived from LISPRO-fed 3XTg-AD mice will be evidenced by M2 phenotype markers (PPARγ activation) (81), increased microglial phagocytosis, decreased pro-inflammatory intracellular signaling (MAPK, NF-kB), and resultant decreased M1 cytokine profile. It is hypothesized that LISPRO will decrease Th1/Th2 cytokine and M1/M2 microglial ratios in primary microglial cultures, strongly enhance M2 phenotype polarization in the presence of IL-4 and dampen or abolish the M1 response to TNFα. IL-4 should decrease Notch1 expression in microglial cells since an up-regulation of Notch1 is associated with pro-inflammatory events (82). These data should be important to begin to understand how LISPRO mechanistically works at the cellular level to reduce AD pathology and cognitive impairment.

In light of one recent study (72), it is possible that LISPRO's γ-secretase inhibitor (GSI) inhibitory activity may impair microglial phagocytosis of Aβ. However, the current results showed that LISPRO promotes microglial phagocytosis of Aβ (FIG. 4). If the in vivo studies show that LISPRO reduces behavioral impairment and AD-like pathology in these mice, the conclusion could be drawn that any GSI mediated reduction in phagocytic ability by LIS- PRO is over-ridden by their GSI effect in reducing neuronal APP amyloidogenic processing. Extra aliquots of primary microglial cell samples will be stocked so that there will be enough to cover all the analysis, in the event that any of these cells are lost by attrition. Taken together, these results should clearly emphasize that microglial activity is not merely a reflection of stimulus strength or persistence. Rather, it is determined largely by the nature and context of the stimuli and the intracellular signal transduction pathways that they activate.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES FOR EXAMPLES 1-21

1. Shorter E. The history of lithium therapy. Bipolar Disord. 2009; 11 Suppl 2:4-9. Epub 2009 Jun. 23. doi: 10.1111/j.1399-5618.2009.00706.x. PubMed PMID: 19538681.
2. Forlenza O V, Diniz B S, Radanovic M, Santos F S, Talib L L, Gattaz W F. Disease-modifying properties of long-term lithium treatment for amnestic mild cognitive impairment: randomised controlled trial. The British journal of psychiatry: the journal of mental science. 2011; 198(5):351-6. doi: 10.1192/bjp.bp.110.080044. PubMed PMID: 21525519.
3. Nunes M A, Viel T A, Buck H S. Microdose lithium treatment stabilized cognitive impairment in patients with Alzheimer's disease. Current Alzheimer research. 2013; 10(1):104-7. PubMed PMID: 22746245.
4. O'Donnell K C, Gould T D. The behavioral actions of lithium in rodent models: leads to develop novel therapeutics. Neuroscience and biobehavioral reviews. 2007; 31(6):932-62. Epub 2007 May 29. doi: 10.1016/j.neubiorev.2007.04.002. PubMed PMID: 17532044; PubMed Central PMCID: PMCPMC2150568.
5. Fukumoto T, Morinobu S, Okamoto Y, Kagaya A, Yamawaki S. Chronic lithium treatment increases the expression of brain-derived neurotrophic factor in the rat brain. Psychopharmacology (Berl). 2001; 158(1):100-6. doi: 10.1007/s002130100871. PubMed PMID: 11685390.
6. Leyhe T, Eschweiler G W, Stransky E, Gasser T, Annas P, Basun H, et al. Increase of BDNF serum concentration in lithium treated patients with early Alzheimer's disease. Journal of Alzheimer's disease: JAD. 2009; 16(3):649-56. doi: 10.3233/JAD-2009-1004. PubMed PMID: 19276559.
7. Yuskaitis C J, Jope R S. Glycogen synthase kinase-3 regulates microglial migration, inflammation, and inflammation-induced neurotoxicity. Cell Signal. 2009; 21(2): 264-73. doi: 10.1016/j.cellsig.2008.10.014. PubMed PMID: 19007880; PubMed Central PMCID: PMC2630396.
8. Frick L R, Williams K, Pittenger C. Microglial dysregulation in psychiatric disease. Clinical & developmental immunology. 2013; 2013:608654. doi: 10.1155/2013/608654. PubMed PMID: 23690824; PubMed Central PMCID: PMC3652125.
9. Phiel C J, Klein P S. Molecular targets of lithium action. Annu Rev Pharmacol Toxicol. 2001; 41:789-813. Epub 2001 Mar. 27. doi: 10.1146/annurev.pharmtox.41.1.789. PubMed PMID: 11264477.
10. Klein P S, Melton D A. A molecular mechanism for the effect of lithium on development. Proc Natl Acad Sci USA. 1996; 93(16):8455-9. Epub 1996 Aug. 6. PubMed PMID: 8710892; PubMed Central PMCID: PMC38692.
11. Mines M A, Beurel E, Jope R S. Regulation of cell survival mechanisms in Alzheimer's disease by glycogen synthase kinase-3. International journal of Alzheimer's disease. 2011; 2011:861072. Epub 2011 Jun. 2. doi: 10.4061/2011/861072. PubMed PMID: 21629713; PubMed Central PMCID: PMCPMC3100684.
12. Vassar R, Bennett B D, Babu-Khan S, Kahn S, Mendiaz E A, Denis P, et al. Beta-secretase cleavage of Alzheimer's amyloid precursor protein by the transmembrane aspartic protease BACE. Science (New York, N.Y.). 1999; 286(5440):735-41. Epub 1999 Oct. 26. doi: 7936 [pii]. PubMed PMID: 10531052.
13. Phiel C J, Wilson C A, Lee V M, Klein P S. GSK-3alpha regulates production of Alzheimer's disease amyloid-beta peptides. Nature. 2003; 423(6938):435-9. Epub 2003 May 23. doi: 10.1038/nature01640. PubMed PMID: 12761548.
14. Forlenza O V, De-Paula V J, Diniz B S. Neuroprotective effects of lithium: implications for the treatment of Alzheimer's disease and related neurodegenerative disorders. ACS chemical neuroscience. 2014; 5(6):443-50. Epub 2014 Apr. 29. doi: 10.1021/cn5000309. PubMed PMID: 24766396; PubMed Central PMCID: PMCPMC4063497.
15. Hernandez F, Lucas J J, Avila J. GSK3 and tau: two convergence points in Alzheimer's disease. Journal of Alzheimer's disease: JAD. 2013; 33 Suppl 1:S141-4. Epub 2012 Jun. 20. doi: 10.3233/jad-2012-129025. PubMed PMID: 22710914.
16. Davenport V D. Distribution of parenterally administered lithium in plasma, brain and muscle of rats. Am J Physiol. 1950; 163(3):633-41. Epub 1950 Dec. 1. PubMed PMID: 14799641.
17. Ebadi M S, Simmons V J, Hendrickson M J, Lacy P S. Pharmacokinetics of lithium and its regional distribution in rat brain. Eur J Pharmacol. 1974; 27(3):324-9. Epub 1974 Aug. 1. PubMed PMID: 4422028.
18. Livingstone C, Rampes H. Lithium: a review of its metabolic adverse effects. J Psychopharmacol. 2006; 20(3):347-55. Epub 2005 Sep. 22. doi: 10.1177/0269881105057515. PubMed PMID: 16174674.
19. Schou M, Baastrup P C, Grof P, Weis P, Angst J. Pharmacological and clinical problems of lithium prophylaxis. The British journal of psychiatry: the journal of mental science. 1970; 116(535):615-9. PubMed PMID: 5452362.
20. Smith A J, Kim S H, Duggirala N K, Jin J, Wojtas L, Ehrhart J, et al. Improving lithium therapeutics by crystal engineering of novel ionic cocrystals. Molecular pharmaceutics. 2013; 10(12):4728-38. Epub 2013 Nov. 7. doi: 10.1021/mp400571a. PubMed PMID: 24191685; PubMed Central PMCID: PMCPMC3850245.
21. Rao R, Zhang M Z, Zhao M, Cai H, Harris R C, Breyer M D, et al. Lithium treatment inhibits renal GSK-3 activity and promotes cyclooxygenase 2-dependent polyuria. American journal of physiology Renal physiology. 2005; 288(4):F642-9. Epub 2004 Dec. 9. doi: 10.1152/ajprenal.00287.2004. PubMed PMID: 15585669.

22. FDA. Guidance for Industry: Regulatory Classification of Pharmaceutical Co-Crystals. In: Services UDoHaH, Administration FaD, Research CfDEa, editors. April 2013.
23. Almarsson O, Zaworotko M J. Crystal engineering of the composition of pharmaceutical phases. Do pharmaceutical co-crystals represent a new path to improved medicines? Chemical communications. 2004(17):1889-96. doi: 10.1039/b402150a. PubMed PMID: 15340589.
24. Desiraju G R. Supramolecular Synthons in Crystal Engineering-A New Organic Synthesis. Angewandte Chemie. 1995; 34(21):2311-27.
25. Moulton B, Zaworotko M J. From molecules to crystal engineering: supramolecular isomerism and polymorphism in network solids. Chemical reviews. 2001; 101 (6):1629-58. PubMed PMID: 11709994.
26. Almarsson Ö, Peterson M L, Zaworotko M. The A to Z of pharmaceutical cocrystals: a decade of fast-moving new science and patents. Pharmaceutical Patent Analyst. 2012; 1(3):313-27.
27. Aprahamian I, Santos F S, dos Santos B, Talib L, Diniz B S, Radanovic M, et al. Long-term, low-dose lithium treatment does not impair renal function in the elderly: a 2-year randomized, placebo-controlled trial followed by single-blind extension. The Journal of clinical psychiatry. 2014; 75(7):e672-8. Epub 2014 Aug. 6. doi: 10.4088/ JCP.13m08741. PubMed PMID: 25093483.
28. Zhu Y, Hou H, Rezai-Zadeh K, Giunta B, Ruscin A, Gemma C, et al. CD45 deficiency drives amyloid-beta peptide oligomers and neuronal loss in Alzheimer's disease mice. Journal of Neuroscience. 2011; 31(4):1355-65. Epub 2011 Jan. 29. doi: 31/4/1355 [pii] 10.1523/JNEUROSCI.3268-10.2011. PubMed PMID: 21273420; PubMed Central PMCID: PMC3068193.
29. Zhu Y, Obregon D, Hou H, Giunta B, Ehrhart J, Fernandez F, et al. Mutant presenilin-1 deregulated peripheral immunity exacerbates Alzheimer-like pathology. Journal of cellular and molecular medicine. 2011; 15(2):327-38. Epub 2009 Nov. 11. doi: 10.1111/j.1582-4934.2009.00962.x. PubMed PMID: 19900216; PubMed Central PMCID: PMC2891003.
30. Tan J, Crucian B E, Chang A E, Aruga E, Aruga A, Dovhey S E, et al. Interferon-gamma-inducing factor elicits antitumor immunity in association with interferon-gamma production. Journal of immunotherapy (Hagerstown, Md.: 1997). 1998; 21(1):48-55. Epub 1998 Feb. 11. PubMed PMID: 9456436.
31. Lippmann S, Evans R. A comparison of three types of lithium release preparations. Hospital & community psychiatry. 1983; 34(2):113-4. Epub 1983 Feb. 1. PubMed PMID: 6826160.
32. Cooper T B, Simpson G M, Lee J H, Bergner P E. Evaluation of a slow-release lithium carbonate formulation. The American journal of psychiatry. 1978; 135(8): 917-22. Epub 1978 Aug. 1. PubMed PMID: 665833.
33. Ciftci K, Capan Y, Ozturk O, Hincal A A. Formulation and in vitro-in vivo evaluation of sustained-release lithium carbonate tablets. Pharmaceutical research. 1990; 7(4):359-63. Epub 1990 Apr. 1. PubMed PMID: 2114020.
34. Emami J, Tavakoli N, Movahedian A. Formulation of sustained-release lithium carbonate matrix tablets: influence of hydrophilic materials on the release rate and in vitro-in vivo evaluation. Journal of pharmacy & pharmaceutical sciences: a publication of the Canadian Society for Pharmaceutical Sciences, Societe canadienne des sciences pharmaceutiques. 2004; 7(3):338-44. Epub 2004 Dec. 4. PubMed PMID: 15576014.
35. Rao R, Hao C M, Breyer M D. Hypertonic stress activates glycogen synthase kinase 3beta-mediated apoptosis of renal medullary interstitial cells, suppressing an NFkappaB-driven cyclooxygenase-2-dependent survival pathway. The Journal of biological chemistry. 2004; 279 (6):3949-55. Epub 2003 Nov. 11. doi: 10.1074/ jbc.M309325200. PubMed PMID: 14607840.
36. Oddo S, Caccamo A, Shepherd J D, Murphy M P, Golde T E, Kayed R, et al. Triple-transgenic model of Alzheimer's disease with plaques and tangles: intracellular Abeta and synaptic dysfunction. Neuron. 2003; 39(3):409-21. Epub 2003 Aug. 5. PubMed PMID: 12895417.
37. Arsenault D, Julien C, Tremblay C, Calon F. DHA improves cognition and prevents dysfunction of entorhinal cortex neurons in 3xTg-AD mice. PLoS One. 2011; 6(2):e17397. Epub 2011 Mar. 9. doi: 10.1371/journal. pone.0017397. PubMed PMID: 21383850; PubMed Central PMCID: PMC3044176.
38. Masciopinto F, Di Pietro N, Corona C, Bomba M, Pipino C, Curcio M, et al. Effects of long-term treatment with pioglitazone on cognition and glucose metabolism of PS1-KI, 3xTg-AD, and wild-type mice. Cell Death Dis. 2012; 3:e448. Epub 2012 Dec. 21. doi: 10.1038/cddis.2012.189. PubMed PMID: 23254291; PubMed Central PMCID: PMC3542623.
39. Peng J, Liang G, Inan S, Wu Z, Joseph D J, Meng Q, et al. Dantrolene ameliorates cognitive decline and neuropathology in Alzheimer triple transgenic mice. Neuroscience letters. 2012; 516(2):274-9. Epub 2012 Apr. 21. doi: 10.1016/j.neulet.2012.04.008. PubMed PMID: 22516463; PubMed Central PMCID: PMC3351794.
40. Branca C, Wisely E V, Hartman L K, Caccamo A, Oddo S. Administration of a selective beta2 adrenergic receptor antagonist exacerbates neuropathology and cognitive deficits in a mouse model of Alzheimer's disease. Neurobiology of aging. 2014; 35(12):2726-35. Epub 2014 Jul. 19. doi: 10.1016/j.neurobiolaging.2014.06.011. PubMed PMID: 25034342; PubMed Central PMCID: PMCPMC4252846.
41. Rosario E R, Carroll J, Pike C J. Testosterone regulation of Alzheimer-like neuropathology in male 3xTg-AD mice involves both estrogen and androgen pathways. Brain research. 2010; 1359:281-90. Epub 2010 Sep. 3. doi: 10.1016/j.brainres.2010.08.068. PubMed PMID: 20807511; PubMed Central PMCID: PMCPMC2965035.
42. Arendash G W, Gordon M N, Diamond D M, Austin L A, Hatcher J M, Jantzen P, et al. Behavioral assessment of Alzheimer's transgenic mice following long-term Abeta vaccination: task specificity and correlations between Abeta deposition and spatial memory. DNA and cell biology. 2001; 20(11):737-44. Epub 2002 Jan. 15. doi: 10.1089/10445490152717604. PubMed PMID: 11788052.
43. Arendash G W, Garcia M F, Costa D A, Cracchiolo J R, Wefes I M, Potter H. Environmental enrichment improves cognition in aged Alzheimer's transgenic mice despite stable beta-amyloid deposition. Neuroreport. 2004; 15(11):1751-4. Epub 2004 Jul. 17. PubMed PMID: 15257141.
44. Arendash G W, Lewis J, Leighty R E, McGowan E, Cracchiolo J R, Hutton M, et al. Multi-metric behavioral comparison of APPsw and P301L models for Alzheimer's disease: linkage of poorer cognitive performance to tau pathology in forebrain. Brain research. 2004; 1012(1-2): 29-41. Epub 2004 May. 26. doi: 10.1016/ j.brainres.2004.02.081. PubMed PMID: 15158158.

45. Jeon D, Yang Y M, Jeong M J, Philipson K D, Rhim H, Shin H S. Enhanced learning and memory in mice lacking Na+/Ca2+ exchanger 2. Neuron. 2003; 38(6):965-76. Epub 2003 Jun. 24. PubMed PMID: 12818181.

46. Jacobsen J S, Wu C C, Redwine J M, Comery T A, Arias R, Bowlby M, et al. Early-onset behavioral and synaptic deficits in a mouse model of Alzheimer's disease. Proceedings of the National Academy of Sciences of the United States of America. 2006; 103(13):5161-6. Epub 2006 Mar. 22. doi: 10.1073/pnas.0600948103. PubMed PMID: 16549764; PubMed Central PMCID: PMC1405622.

47. Banaceur S, Banasr S, Sakly M, Abdelmelek H. Whole body exposure to 2.4 GHz WIFI signals: effects on cognitive impairment in adult triple transgenic mouse models of Alzheimer's disease (3xTg-AD). Behavioural brain research. 2013; 240:197-201. Epub 2012 Dec. 1. doi: 10.1016/j.bbr.2012.11.021. PubMed PMID: 23195115.

48. Billings L M, Oddo S, Green K N, McGaugh J L, LaFerla F M. Intraneuronal Abeta causes the onset of early Alzheimer's disease-related cognitive deficits in transgenic mice. Neuron. 2005; 45(5):675-88. Epub 2005 Mar. 8. doi: 10.1016/j.neuron.2005.01.040. PubMed PMID: 15748844.

49. Cheng K K, Yeung C F, Ho S W, Chow S F, Chow A H, Baum L. Highly stabilized curcumin nanoparticles tested in an in vitro blood-brain barrier model and in Alzheimer's disease Tg2576 mice. The AAPS journal. 2013; 15(2):324-36. Epub 2012 Dec. 12. doi: 10.1208/s12248-012-9444-4. PubMed PMID: 23229335; PubMed Central PMCID: PMC3675736.

50. Dong H, Murphy K M, Meng L, Montalvo-Ortiz J, Zeng Z, Kolber B J, et al. Corticotrophin releasing factor accelerates neuropathology and cognitive decline in a mouse model of Alzheimer's disease. Journal of Alzheimer's disease: JAD. 2012; 28(3):579-92. Epub 2011 Nov. 3. doi: 10.3233/jad-2011-111328. PubMed PMID: 22045495; PubMed Central PMCID: PMC3494090.

51. Joshi Y B, Chu J, Pratico D. Stress hormone leads to memory deficits and altered tau phosphorylation in a model of Alzheimer's disease. Journal of Alzheimer's disease: JAD. 2012; 31(1):167-76. Epub 2012 Apr. 26. doi: 10.3233/jad-2012-120328. PubMed PMID: 22531419; PubMed Central PMCID: PMC3882896.

52. Lee S T, Chu K, Park J E, Jung K H, Jeon D, Lim J Y, et al. Erythropoietin improves memory function with reducing endothelial dysfunction and amyloid-beta burden in Alzheimer's disease models. Journal of neurochemistry. 2012; 120(1):115-24. Epub 2011 Oct. 19. doi: 10.1111/j.1471-4159.2011.07534.x. PubMed PMID: 22004348.

53. Todd Roach J, Volmar C H, Dwivedi S, Town T, Crescentini R, Crawford F, et al. Behavioral effects of CD40-CD40L pathway disruption in aged PSAPP mice. Brain research. 2004; 1015(1-2):161-8. Epub 2004 Jun. 30. doi: 10.1016/j.brainres.2004.05.004. PubMed PMID: 15223380.

54. Rezai-Zadeh K, Shytle D, Sun N, Mori T, Hou H, Jeanniton D, et al. Green tea epigallocatechin-3-gallate (EGCG) modulates amyloid precursor protein cleavage and reduces cerebral amyloidosis in Alzheimer transgenic mice. The Journal of neuroscience: the official journal of the Society for Neuroscience. 2005; 25(38):8807-14. Epub 2005 Sep. 24. doi: 25/38/8807 [pii] 10.1523/JNEUROSCI.1521-05.2005. PubMed PMID: 16177050.

55. Rezai-Zadeh K, Douglas S, Bai Y, Tian J, Hou H, Mori T, et al. Flavonoid-mediated presenilin-1 phosphorylation reduces Alzheimer's disease beta-amyloid production. Journal of cellular and molecular medicine. 2009; 13:574-88.

56. Tan J, Town T, Paris D, Mori T, Suo Z, Crawford F, et al. Microglial activation resulting from CD40-CD40L interaction after beta-amyloid stimulation. Science (New York, N.Y.). 1999; 286(5448):2352-5. Epub 1999 Dec. 22. PubMed PMID: 10600748.

57. Rezai-Zadeh K, Arendash G W, Hou H, Fernandez F, Jensen M, Runfeldt M, et al. Green tea epigallocatechin-3-gallate (EGCG) reduces beta-amyloid mediated cognitive impairment and modulates tau pathology in Alzheimer transgenic mice. Brain research. 2008; 1214: 177-87. Epub 2008 May 7. doi: 10.1016/j.brainres.2008.02.107. PubMed PMID: 18457818.

58. Tan J, Town T, Crawford F, Mori T, DelleDonne A, Crescentini R, et al. Role of CD40 ligand in amyloidosis in transgenic Alzheimer's mice. Nat Neurosci. 2002; 5(12):1288-93. Epub 2002 Oct. 29. doi: 10.1038/nn968 nn968 [pii]. PubMed PMID: 12402041.

59. Smith A, Giunta B, Bickford P C, Fountain M, Tan J, Shytle R D. Nanolipidic particles improve the bioavailability and alpha-secretase inducing ability of epigallocatechin-3-gallate (EGCG) for the treatment of Alzheimer's disease. International journal of pharmaceutics. 2010; 389(1-2):207-12. Epub 2010 Jan. 20. doi: 10.1016/j.ijpharm.2010.01.012. PubMed PMID: 20083179.

60. Sarkar S, Floto R A, Berger Z, Imarisio S, Cordenier A, Pasco M, et al. Lithium induces autophagy by inhibiting inositol monophosphatase. The Journal of cell biology. 2005; 170(7):1101-11. Epub 2005 Sep. 28. doi: 10.1083/jcb.200504035. PubMed PMID: 16186256; PubMed Central PMCID: PMCPMC2171537.

61. Kim J S, Chang M Y, Yu I T, Kim J H, Lee S H, Lee Y S, et al. Lithium selectively increases neuronal differentiation of hippocampal neural progenitor cells both in vitro and in vivo. Journal of neurochemistry. 2004; 89(2): 324-36. Epub 2004 Apr. 2. doi: 10.1046/j.1471-4159.2004.02329.x. PubMed PMID: 15056276.

62. Milano J, McKay J, Dagenais C, Foster-Brown L, Pognan F, Gadient R, et al. Modulation of notch processing by gamma-secretase inhibitors causes intestinal goblet cell metaplasia and induction of genes known to specify gut secretory lineage differentiation. Toxicological sciences: an official journal of the Society of Toxicology. 2004; 82(1):341-58. Epub 2004 Aug. 21. doi: 10.1093/toxsci/kfh254. PubMed PMID: 15319485.

63. Schock-Kusch D, Geraci S, Ermeling E, Shulhevich Y, Sticht C, Hesser J, et al. Reliability of transcutaneous measurement of renal function in various strains of conscious mice. PLoS One. 2013; 8(8):e71519. Epub 2013 Aug. 27. doi: 10.1371/journal.pone.0071519. PubMed PMID: 23977062; PubMed Central PMCID: PMCPMC3747225.

64. Musik I, Kocot J, Lewandowska A, Zelazowska R, Kielczykowska M. The investigation of the possible protective influence of selenium on antioxidant barrier in heart of rats exposed to lithium. Life sciences. 2015; 132:1-5. Epub 2015 Apr. 30. doi: 10.1016/j.lfs.2015.03.025. PubMed PMID: 25921764.

65. Abdel-Zaher A O, Abdel-Rahman M M. Lithium chloride-induced cardiovascular changes in rabbits are mediated by adenosine triphosphate-sensitive potassium channels. Pharmacological research. 1999; 39(4):275-82. Epub 1999 Apr. 20. doi: 10.1006/phrs.1998.0445. PubMed PMID: 10208757.
66. Sharan S, Nikhil K, Roy P. Disruption of thyroid hormone functions by low dose exposure of tributyltin: an in vitro and in vivo approach. General and comparative endocrinology. 2014; 206:155-65. Epub 2014 Aug. 8. doi: 10.1016/j.ygcen.2014.07.027. PubMed PMID: 25101840.
67. Cryns K, Shamir A, Shapiro J, Daneels G, Goris I, Van Craenendonck H, et al. Lack of lithium-like behavioral and molecular effects in IMPA2 knockout mice. Neuropsychopharmacology: official publication of the American College of Neuropsychopharmacology. 2007; 32(4):881-91. Epub 2006 Jul. 15. doi: 10.1038/sj.npp.1301154. PubMed PMID: 16841073.
68. Kofman O, Belmaker R H, Grisaru N, Alpert C, Fuchs I, Katz V, et al. Myo-inositol attenuates two specific behavioral effects of acute lithium in rats. Psychopharmacology bulletin. 1991; 27(3):185-90. Epub 1991 Jan. 1. PubMed PMID: 1775587.
69. Gomez-Sintes R, Lucas J J. NFAT/Fas signaling mediates the neuronal apoptosis and motor side effects of GSK-3 inhibition in a mouse model of lithium therapy. The Journal of clinical investigation. 2010; 120(7):2432-45. Epub 2010 Jun. 10. doi: 10.1172/jci37873. PubMed PMID: 20530871; PubMed Central PMCID: PMCPMC2898581.
70. Michelucci A, Heurtaux T, Grandbarbe L, Morga E, Heuschling P. Characterization of the microglial phenotype under specific pro-inflammatory and anti-inflammatory conditions: Effects of oligomeric and fibrillar amyloid-beta. Journal of neuroimmunology. 2009; 210(1-2):3-12. Epub 2009 Mar. 10. doi: 10.1016/j.jneuroim.2009.02.003. PubMed PMID: 19269040.
71. Varnum M M, Ikezu T. The classification of microglial activation phenotypes on neurodegeneration and regeneration in Alzheimer's disease brain. Archivum immunologiae et therapiae experimentalis. 2012; 60(4):251-66. Epub 2012 Jun. 20. doi: 10.1007/s00005-012-0181-2. PubMed PMID: 22710659; PubMed Central PMCID: PMCPMC4429536.
72. Farfara D, Trudler D, Segev-Amzaleg N, Galron R, Stein R, Frenkel D. gamma-Secretase component presenilin is important for microglia beta-amyloid clearance. Annals of neurology. 2011; 69(1):170-80. Epub 2011 Feb. 1. doi: 10.1002/ana.22191. PubMed PMID: 21280087.
73. Townsend K P, Town T, Mori T, Lue L F, Shytle D, Sanberg P R, et al. CD40 signaling regulates innate and adaptive activation of microglia in response to amyloid beta-peptide. European journal of immunology. 2005; 35(3):901-10. Epub 2005 Feb. 3. doi: 10.1002/eji.200425585. PubMed PMID: 15688347.
74. Rezai-Zadeh K, Ehrhart J, Bai Y, Sanberg P R, Bickford P, Tan J, et al. Apigenin and luteolin modulate microglial activation via inhibition of STAT1-induced CD40 expression. Journal of neuroinflammation. 2008; 5:41. Epub 2008 Sep. 27. doi: 10.1186/1742-2094-5-41. PubMed PMID: 18817573; PubMed Central PMCID: PMCPMC2569027.
75. Zhu Y, Hou H, Rezai-Zadeh K, Giunta B, Ruscin A, Gemma C, et al. CD45 deficiency drives amyloid-beta peptide oligomers and neuronal loss in Alzheimer's disease mice. The Journal of neuroscience: the official journal of the Society for Neuroscience. 2011; 31(4):1355-65. Epub 2011 Jan. 29. doi: 10.1523/jneurosci.3268-10.2011. PubMed PMID: 21273420; PubMed Central PMCID: PMC3068193.
76. Ye S M, Johnson R W. Increased interleukin-6 expression by microglia from brain of aged mice. Journal of neuroimmunology. 1999; 93(1-2):139-48. Epub 1999 Jan. 23. PubMed PMID: 10378877.
77. Giunta B, Fernandez F, Nikolic W V, Obregon D, Rrapo E, Town T, et al. Inflammaging as a prodrome to Alzheimer's disease. Journal of neuroinflammation. 2008; 5:51. Epub 2008 Nov. 19. doi: 10.1186/1742-2094-5-51. PubMed PMID: 19014446; PubMed Central PMCID: PMCPMC2615427.
78. Ye S M, Johnson R W. An age-related decline in interleukin-10 may contribute to the increased expression of interleukin-6 in brain of aged mice. Neuroimmunomodulation. 2001; 9(4):183-92. Epub 2002 Feb. 16. doi: 49025. PubMed PMID: 11847480.
79. Maher F O, Nolan Y, Lynch M A. Downregulation of IL-4-induced signalling in hippocampus contributes to deficits in LTP in the aged rat. Neurobiology of aging. 2005; 26(5):717-28. Epub 2005 Feb. 15. doi: 10.1016/j.neurobiolaging.2004.07.002. PubMed PMID: 15708447.
80. Nolan Y, Maher F O, Martin D S, Clarke R M, Brady M T, Bolton A E, et al. Role of interleukin-4 in regulation of age-related inflammatory changes in the hippocampus. The Journal of biological chemistry. 2005; 280(10):9354-62. Epub 2004 Dec. 24. doi: 10.1074/jbc.M412170200. PubMed PMID: 15615726.
81. Mandrekar-Colucci S, Karlo J C, Landreth G E. Mechanisms underlying the rapid peroxisome proliferator-activated receptor-gamma-mediated amyloid clearance and reversal of cognitive deficits in a murine model of Alzheimer's disease. The Journal of neuroscience: the official journal of the Society for Neuroscience. 2012; 32(30):10117-28. Epub 2012 Jul. 28. doi: 10.1523/jneurosci.5268-11.2012. PubMed PMID: 22836247; PubMed Central PMCID: PMCPMC3433721.
82. Grandbarbe L, Michelucci A, Heurtaux T, Hemmer K, Morga E, Heuschling P. Notch signaling modulates the activation of microglial cells. Glia. 2007; 55(15):1519-30. Epub 2007 Aug. 21. doi: 10.1002/glia.20553. PubMed PMID: 17705199.
83. Ryves W J, Harwood A J. Biochem Biophys Res Commun. 2001 Jan. 26; 280(3):720-5. Lithium inhibits glycogen synthase kinase-3 by competition for magnesium.

We claim:
1. A method for treating a neuropsychiatric disorder, comprising administering an effective amount of a co-crystal of lithium to a subject having the neuropsychiatric disorder, wherein the co-crystal comprises lithium, or a pharmaceutically acceptable salt thereof, and an amino acid; and administering an additional agent for treating the neuropsychiatric disorder before, during, or after the administration of the lithium co-crystal.
2. The method of claim 1, wherein the co-crystal comprises a pharmaceutically acceptable salt of lithium, and an amino acid.
3. The method of claim 1, wherein the pharmaceutically acceptable salt is lithium salicylate or lithium hydroxide.
4. The method of claim 1, wherein the amino acid is L-proline.
5. The method of claim 1, wherein the co-crystal comprises lithium salicylate and L-proline.
6. The method of claim 1, wherein the neuropsychiatric disorder is a neurodegenerative disorder.

7. The method of claim 6, wherein the neurodegenerative disorder is Alzheimer's disease, Parkinson's disease, or amyotrophic laterals sclerosis (ALS).

8. The method of claim 1, wherein the neuropsychiatric disorder is a mood disorder, schizoaffective disorder, tic disorder, or suicidality.

9. The method of claim 1, wherein the neuropsychiatric disorder is Alzheimer's disease or other dementia, and the additional agent is a cholinesterase inhibitor, N-methyl D-aspartate antagonist, vitamin E, or a combination of two or more of the foregoing.

10. The method of claim 9, wherein the additional agent is donepezil, rivastigmine, galantamine, memantine, or a combination of two or more of the foregoing.

11. The method of claim 1, wherein the additional agent is an anti-depressant, anti-convulsant, or mood stabilizer.

12. The method of claim 1, wherein the additional agent is a selective serotonin reuptake inhibitor (SSRI), serotonin-noroepinephrine reuptake inhibitor (SNRI), serotonin antagonist and reuptake inhibitor (SARI), monamine oxidase inhibitor (MAOI), carboxamide, fructose derivative, triazine, or a combination of two or more of the foregoing.

13. The method of claim 1, wherein the lithium co-crystal is administered to the subject in a composition comprising the lithium co-crystal and a pharmaceutically acceptable carrier.

* * * * *

UNITED STATES PATENT AND TRADEMARK OFFICE
CERTIFICATE OF CORRECTION

PATENT NO. : 9,603,869 B2
APPLICATION NO. : 15/161202
DATED : March 28, 2017
INVENTOR(S) : Jun Tan, Adam John Smith and Roland Douglas Shytle It is certified that error appears in the above-identified patent and that said Letters Patent is hereby corrected as shown below:

In the Specification

<u>Column 1,</u>
Line 4, <blank> should read
--GOVERNMENT SUPPORT
This invention was made with government support R01 AG050253 awarded by the National Institutes of Health. The Government has certain rights in the invention.--.
Line 64, "AP-mediated" should read --Aβ-mediated--.

<u>Column 3,</u>
Line 21, "AO ELISA. The AO ELISA" should read --Aβ ELISA. The Aβ ELISA--.
Line 28, "Notch-4E vector. N2a/APPwt/Notch-4E" should read --Notch-ΔE vector. N2a/APPwt/Notch-ΔE--.

<u>Column 4,</u>
Lines 12-13, "AO ELISA" should read --Aβ ELISA--.
Line 32, "cell were" should read --cells were--.

<u>Column 7,</u>
Line 27, "amino acid." should read --amino acids.--.

<u>Column 13,</u>
Lines 1-2, "comprising one or more one or more lithium" should read --comprising one or more lithium--.

<u>Column 21,</u>
Line 19, "Lithium Cocrystal Syntheses." should read --Lithium Co-Crystal Syntheses--.

<u>Column 26,</u>
Line 48, "ratios of (3-tubulin" should read --ratios of β-tubulin--.

Signed and Sealed this
First Day of January, 2019

Andrei Iancu
*Director of the United States Patent and Trademark Office*

Column 31,
Line 26, "Extracellular plaques" should read --Extracellular Aβ plaques--.